United States Patent
Reeh et al.

(10) Patent No.: US 11,071,840 B2
(45) Date of Patent: Jul. 27, 2021

(54) HYPOXIA TRAINING DEVICE

(71) Applicant: Lynntech, Inc., College Station, TX (US)

(72) Inventors: Jonathan Reeh, College Station, TX (US); Mahesh Waje, College Station, TX (US); Mehmet Kesmez, College Station, TX (US); Carlos Salinas, Bryan, TX (US); Jibi Varughese, College Station, TX (US); John Zbranek, College Station, TX (US); Seth Cocking, College Station, TX (US); Ashwin Balasubramanian, College Station, TX (US); Cory Teurman, College Station, TX (US); James Netherland, Bryan, TX (US); Geoffrey Duncan Hitchens, Allen, TX (US)

(73) Assignee: Lynntech, Inc., College Station, TX (US)

(*) Notice: Subject to any disclaimer, the term of this patent is extended or adjusted under 35 U.S.C. 154(b) by 0 days.

(21) Appl. No.: 15/584,887

(22) Filed: May 2, 2017

(65) Prior Publication Data

US 2017/0326327 A1    Nov. 16, 2017

Related U.S. Application Data

(60) Provisional application No. 62/336,426, filed on May 13, 2016.

(51) Int. Cl.
*A61M 16/10* (2006.01)
*G09B 9/16* (2006.01)
(Continued)

(52) U.S. Cl.
CPC ........ *A61M 16/10* (2013.01); *A61M 16/0045* (2013.01); *A61M 16/101* (2014.02);
(Continued)

(58) Field of Classification Search
CPC .. A61M 16/0045; A61M 16/06; A61M 16/10; A61M 16/22; A61M 2016/1025;
(Continued)

(56) References Cited

U.S. PATENT DOCUMENTS

| 3,489,670 A | 1/1970 | Maget |
| 3,579,292 A * | 5/1971 | Mullhaupt ............ C01B 13/083 252/186.38 |

(Continued)

FOREIGN PATENT DOCUMENTS

| GB | 2276458 A | 3/1994 |
| GB | 2558847 A | 7/2018 |

(Continued)

OTHER PUBLICATIONS

Owe at a. Iridium-ruthenium single phase mixed oxides for oxygen evolution: Composition dependence on electrocatalytic activity. Electrochemica Acta 70. pp. 158-164. (Year: 2012).*

(Continued)

*Primary Examiner* — Nicholas A Smith
(74) *Attorney, Agent, or Firm* — Edwin S. Flores; Chalker Flores, LLP

(57) ABSTRACT

The present invention includes a device for hypoxia training comprising: one or more electrochemical cells each comprising: a cathode and an anode separated by a proton exchange membrane, each of the anode and cathode in communication with an input and an output, wherein the input of the cathode is in fluid communication with ambient air, and wherein the input of the anode is in fluid communication with a source of liquid water; a power supply (Continued)

connected to the one or more electrochemical cells; and a mask in fluid communication with the output from the cathode of the one or more electrochemical cells, wherein oxygen is removed from the ambient air during contact with the cathode when hydrogen ions separated from liquid water by a catalyst on the anode convert oxygen in the ambient air into water.

38 Claims, 29 Drawing Sheets

(51) Int. Cl.
| | | |
|---|---|---|
| A61M 16/22 | (2006.01) | |
| A61M 16/20 | (2006.01) | |
| G09B 9/08 | (2006.01) | |
| C25B 1/04 | (2021.01) | |
| A61M 16/00 | (2006.01) | |
| A62B 7/14 | (2006.01) | |
| A63B 23/18 | (2006.01) | |
| A61M 16/12 | (2006.01) | |
| A61M 16/16 | (2006.01) | |
| A61M 16/06 | (2006.01) | |
| H01M 8/04089 | (2016.01) | |

(52) U.S. Cl.
CPC .......... *A61M 16/202* (2014.02); *A61M 16/22* (2013.01); *A62B 7/14* (2013.01); *A63B 23/18* (2013.01); *C25B 1/04* (2013.01); *G09B 9/085* (2013.01); *G09B 9/165* (2013.01); *A61M 16/06* (2013.01); *A61M 16/106* (2014.02); *A61M 16/1085* (2014.02); *A61M 16/12* (2013.01); *A61M 16/16* (2013.01); *A61M 16/209* (2014.02); *A61M 2016/003* (2013.01); *A61M 2016/0015* (2013.01); *A61M 2016/0027* (2013.01); *A61M 2016/1025* (2013.01); *A61M 2202/0208* (2013.01); *A61M 2205/13* (2013.01); *A61M 2205/3344* (2013.01); *A61M 2205/502* (2013.01); *A61M 2205/52* (2013.01); *A61M 2230/10* (2013.01); *A61M 2230/205* (2013.01); *A61M 2230/42* (2013.01); *A63B 2208/05* (2013.01); *A63B 2213/006* (2013.01); *A63B 2220/56* (2013.01); *H01M 8/04089* (2013.01)

(58) Field of Classification Search
CPC .. A61M 2202/0208; A62B 7/14; A63B 22/18; A63B 2208/05; A63B 2213/006; A63B 2220/56; H01M 8/04089; C25B 1/02; C25B 1/04
See application file for complete search history.

(56) References Cited

U.S. PATENT DOCUMENTS

| | | | |
|---|---|---|---|
| 4,086,923 A | 5/1978 | Henkin | |
| 4,539,086 A | 9/1985 | Fujita et al. | |
| 5,338,412 A | 8/1994 | Burk et al. | |
| 5,924,419 A * | 7/1999 | Kotliar | A23L 3/3418 128/200.24 |
| 5,988,161 A | 11/1999 | Kroll | |
| 6,165,105 A | 12/2000 | Boutellier et al. | |
| 6,171,368 B1 | 1/2001 | Maget et al. | |
| 6,179,986 B1 | 1/2001 | Swette et al. | |
| 6,536,429 B1 | 3/2003 | Pavlov | |
| 6,871,645 B2 * | 3/2005 | Wartman | A61M 16/0045 128/203.12 |
| 7,125,625 B2 | 10/2006 | Cisar et al. | |
| 7,632,338 B2 | 12/2009 | Cipollini | |
| 8,465,630 B2 | 6/2013 | Reed et al. | |
| 2002/0139368 A1 | 10/2002 | Bachinski | |
| 2003/0022200 A1 | 1/2003 | Vissing et al. | |
| 2003/0070678 A1 | 4/2003 | Wartman et al. | |
| 2004/0101723 A1 | 5/2004 | Kruppa et al. | |
| 2004/0134493 A1 | 7/2004 | McCombs | |
| 2004/0185325 A1 * | 9/2004 | Faguy | H01M 4/8605 429/524 |
| 2005/0058871 A1 | 3/2005 | Li et al. | |
| 2005/0136299 A1 | 6/2005 | Richey et al. | |
| 2005/0103193 A1 | 9/2005 | Lyons | |
| 2005/0202374 A1 | 9/2005 | Stepanek et al. | |
| 2005/0247311 A1 * | 11/2005 | Vacchiano | A61M 16/0045 128/203.12 |
| 2006/0225572 A1 | 10/2006 | Kutt et al. | |
| 2007/0034507 A1 | 2/2007 | Sin et al. | |
| 2007/0077200 A1 | 4/2007 | Baker | |
| 2007/0119456 A1 * | 5/2007 | Scott | A61M 16/10 128/205.27 |
| 2007/0181128 A1 | 8/2007 | Stroetz | |
| 2007/0221225 A1 * | 9/2007 | Kutt | A61M 16/0045 128/205.26 |
| 2008/0202774 A1 | 8/2008 | Kotliar | |
| 2009/0183738 A1 | 7/2009 | Kostin | |
| 2010/0065440 A1 | 3/2010 | Nishimura et al. | |
| 2012/0241315 A1 * | 9/2012 | Yoshinaga | F25D 17/042 204/262 |
| 2013/0026195 A1 * | 1/2013 | Park | C02F 1/001 222/394 |
| 2013/0053541 A1 | 2/2013 | Shankar et al. | |
| 2013/0340760 A1 | 12/2013 | Brumley et al. | |
| 2014/0069429 A1 * | 3/2014 | Lucci | A61M 16/0051 128/204.21 |
| 2014/0131217 A1 * | 5/2014 | Buschmann | C01B 7/01 205/440 |
| 2014/0322675 A1 | 10/2014 | Bassovitch | |
| 2015/0323411 A1 * | 11/2015 | Eberlein | G01M 3/3263 73/40 |
| 2016/0095994 A1 | 4/2016 | Currin | |
| 2016/0118679 A1 | 4/2016 | Joos et al. | |
| 2016/0144973 A1 * | 5/2016 | Darling | C25B 15/08 204/265 |
| 2016/0273116 A1 * | 9/2016 | Gilliam | C25B 9/00 |
| 2017/0169906 A1 * | 6/2017 | Arafat | A62B 11/00 |

FOREIGN PATENT DOCUMENTS

| | | |
|---|---|---|
| JP | S61117103 A | 6/1986 |
| WO | 1993023102 A1 | 11/1993 |
| WO | 199834683 A1 | 8/1998 |
| WO | 2003024505 A3 | 3/2003 |

OTHER PUBLICATIONS

Adams, Roger, et al., "Platinum Oxide as a Catalyst in the Reduction of Organic Compounds. III. Preparation and Properties of the Oxide of Platinum Obtained by the Fusion of Chloroplatinic Acid with Sodium Nitrate," Journal of the American Chemical Society, Sep. 1923, vol. 45, pp. 2171-2179.

Artino, R. A., et al., "Mask-On Hypoxia Training for Tactical Jet Aviators: Evaluation of an Alternate Instructional Paradigm." Aviation, Space, and Environmental Medicine, Aug. 2006, vol. 77, No. 8, pp. 857-861.

Artino, R. A., et al., "Normobaric Hypoxia Training: The Effects of Breathing-Gas Flow Rate on Symptoms." Aviation, Space, and Environmental Medicine, Jun. 2009, vol. 80, No. 6, pp. 547-552.

Carothers, Wallace, et al., "Platinum Oxide as a Catalyst in the Reduction of Organic Compounds. II. Reduction of Aldehydes. Activation of the Catalyst by the Salts of Certain Metals," Journal of the American Chemical Society, Feb. 23, 1923, vol. 45, pp. 1071-1086.

Files, D.S., et al., "Depressurization in Military Aircrafts: Rates, Rapidity, and Health Effects for 1055 incidents," Aiation, Space, and Environmental Medicine, Jun. 2005, vol. 76, No. 6, pp. 523-529.

(56) References Cited

OTHER PUBLICATIONS

Fujita, Y., et al., "An electrochemical oxygen separator using an ion-exchange membrane as the electrolyte." Journal of Applied Electrochemistry, Feb. 14, 1986, vol. 16, pp. 935-940.

Sausen, P. K., et al., "A Closed-Loop Reduced Oxygen Breathing Device for Inducing Hypoxia in Humans." Aviation, Space, and Environmental Medicine, Nov. 2003, vol. 74, No. 11, pp. 1190-1197.

Voorhees, V., et al., "Oxides of Platinum in Organic Reductions, The Use of the Oxides of Platinum for the Catalytic Reduction of Organic Compounds. I," Journal of the American Chemical Society, vol. 44, Apr. 10, 1922, pp. 1397-1405.

Westerman, A. R., "Hypoxia familiarisation training by the reduced oxygen breathing method." ADF Health, Apr. 2004, vol. 5, pp. 11-15.

International Search Report and Written Opinion for PCT/US2017/030634 dated Sep. 12, 2017.

EPO search report of EP 17796576.1 dated Jan. 3, 2019, 13 pages.

Katsounaros, I., et al., "Oxygen Electrochemistry as a Cornerstone for Sustainable Energy Conversion," Angew. Chem. Int. Ed., 2014, vol. 53, pp. 102-121.

International Search Report and Written Opinion by the Korean Intellectual Property Office for PCT/US2019/030868 dated Oct. 8, 2019, 15 pp.

\* cited by examiner

HYPOXIA TRAINING DEVICE

CROSS-REFERENCE TO RELATED APPLICATIONS

This application claims priority to U.S. Provisional Application Ser. No. 62/336,426, filed May 13, 2016, the entire contents of which are incorporated herein by reference.

STATEMENT OF FEDERALLY FUNDED RESEARCH

This invention was made with government support under contract numbers N68335-14-C-0068 and N68335-15-C-0050 awarded by the United States Navy. The government has certain rights in the invention.

TECHNICAL FIELD OF THE INVENTION

The present invention relates in general to the field of devices and methods for training at high altitude, and more particularly, to a device and method for hypoxia training.

BACKGROUND OF THE INVENTION

Without limiting the scope of the invention, its background is described in connection with hypoxia training devices.

High altitude flight presents many risks to pilots including hypoxia, which severely affects the pilot's cognitive function. In aviation, hypoxia is developed due to low air pressure and thus low oxygen partial pressure at high altitudes. If not recognized and corrected, hypoxia will cause the pilot to lose consciousness and control of the aircraft. Based on a recent USAF publication, from 1981 to 2003, over 1000 hypoxia related incidents (of which 350 cases involved adverse health effects) occurred within US military aircraft pilots. Early recognition of hypoxic conditions is paramount to implementing corrective action and avoiding catastrophe and this can only be achieved through extensive hypoxia training.

Currently, hypoxia training for pilots has been a very limited effort in the US military due to insufficient number of mobile hypoxia training devices and the difficulty of integrating these conventional training devices with flight simulator software. Historically, Low-Pressure Chamber (LPC) technology has been used to simulate high altitude environments for pilot hypoxia training. However, training in these hypobaric chambers is costly, time consuming, and exposes the trainees to risks of decompression sickness, barotraumas, and other dysbarisms. Recently, normobaric training devices, such as the Reduced-Oxygen Breathing Device (ROBD) have been successfully used for training without the risks associated with LPCs. These devices simulate high altitude atmosphere by delivering oxygen depleted air to the trainee at standard atmospheric pressure via an oxygen mask. Ideally, this training device would be implemented in conjunction with an existing full motion flight simulator to realistically mimic in-flight failures. However, these devices are currently too bulky for integration with full motion flight simulators and impose heavy logistical burdens on the training facilities including the replacement of large compressed gas cylinders and the need for $CO_2$ absorption canisters. Additionally, most current reduced oxygen breathing devices provide fixed gas flow rates resulting in air starvation of the trainees. A mobile, low maintenance hypoxia training device with pressure demand delivery is needed for integration into existing full-motion flight simulators to increase training quality and efficiency.

SUMMARY OF THE INVENTION

In one embodiment the present invention includes a device for hypoxia training comprising: one or more electrochemical cells each comprising: a cathode and an anode separated by a proton exchange membrane, each of the anode and cathode in communication with an input and an output, wherein the input of the cathode is in fluid communication with ambient air, and wherein the input of the anode is in fluid communication with a source of liquid water; a power supply connected to the one or more electrochemical cells; and a mask in fluid communication with the output from the cathode of the one or more electrochemical cells, wherein oxygen is removed from the ambient air during contact with the cathode when hydrogen ions separated from liquid water by a catalyst on the anode convert oxygen in the ambient air into water. In one aspect, the anode catalyst is an electrocatalyst and wherein water molecules that contact the electrocatalyst are dissociated into hydrogen protons and oxygen by electrolysis, wherein the protons traverse the proton exchange membrane to the cathode, and oxygen in the ambient air is reacted with protons at the cathode into water. In another aspect, the device further comprises an oxygen sensor in fluid communication with the output from the cathode and connected to a processor that determines the amount of oxygen in the output, wherein the processor controls the power to the electrochemical cell based on the amount of oxygen detected and one or more settings for hypoxia training. In another aspect, the device further comprises one or more pumps and valves in fluid communication with the anode and cathode, wherein the one or more pumps and valves control air flow to and from the cathode, and water flow into the anode, wherein the pumps and valves regulate the reduction in oxygen from ambient air and the air flow to the mask and the conversion of water into oxygen. In another aspect, the device further comprises a temperature regulator for the electrochemical cell, wherein the temperature is reduce by contacting the electrochemical cell with a coolant. In another aspect, the device is defined further as a pressure-on-demand device, wherein a reduction in the amount of oxygen removed from the ambient air by the electrochemical cell is controlled based on air intake at the mask, wherein air intake is determined by one or more sensors that monitor breath rate, wherein the one or more sensors are connected to a control logic that adjusts the current to the electrochemical stack in real time. In another aspect, the logic determines how much air is inhaled at the mask, a peak amplitude of the air and a breath rate, and a mass flow controller adjusts the air intake at the mask available to a user. In another aspect, the electrochemical cell comprises a stack of anodes and cathodes. In another aspect, the power supply is defined further as a hybrid power distribution system that limits current draw from an external power source. In another aspect, the device further comprises a water recovery system in fluid communication with the cathode, wherein the water in the water recovery system can be at least one of: delivered to the anode, stored, or disposed. In another aspect, the e anode catalyst is an Ir—Ru-Ox catalyst with at least one of Au or Pt nanoparticles. In another aspect, the anode catalyst is an Ir—Ru-Ox catalyst with a 5 to 95 mol % Ir to Ru ratio. In another aspect, the anode catalyst is an Ir—Ru-Ox catalyst that further comprises at least one of an Au loading range of 0, 1, 5, 10, 15, 20, 25, 30, 35, 40 wt %, or a Pt loading of from 0, 5, 10, 15, 20 wt %. In another aspect, the cathode further comprises a cathode electrochemical catalyst that reduces oxygen in the ambient air. In another aspect, the cathode has a first and a second side, and the first side is in contact with the proton exchange membrane and the second side is in contact with an air diffusion layer, wherein the air diffusion layer is in contact with the cathode input and output. In another aspect, the anode has a first and a second side, and the first side is in contact with the proton exchange membrane and the second side is in contact with a water flow layer, wherein the water flow layer is in contact with the anode input and output. In another aspect, the electrocatalyst demonstrates a greater than 65%, 70%, 75%, 80%, or 85% water electrolysis efficiency. In another aspect, an ion exchange resin is positioned between the source of water and the anode.

In another embodiment the present invention includes a method of controlling the level of oxygen is an air stream during pilot hypoxia training comprising: providing a device to a pilot during hypoxia training that comprises: one or more electrochemical cells each comprising: a cathode and an anode separated by a proton exchange membrane, each of the anode and cathode in communication with an input and an output, wherein the input of the cathode is in fluid communication with ambient air, and wherein the input of the anode is in fluid communication with a source of liquid water; a power supply connected to the one or more electrochemical cells; and a mask in fluid communication with the output from the cathode of the one or more electrochemical cells, wherein oxygen is removed from the ambient air during contact with the cathode when hydrogen ions are separated from liquid water by a catalyst on the anode; and measuring one or more parameters of oxygen use at the mask, wherein the parameters are processed by a logic that controls the current to the one or more electrochemical cells; and modulating the amount of oxygen output from the device during operation. In one aspect, the anode catalyst is an electrocatalyst and further comprising contacting water molecules with the electrocatalyst, wherein the water molecules are dissociated into hydrogen protons and oxygen by electrolysis, wherein the protons traverse the proton exchange membrane to the cathode and oxygen at the cathode is converted into water by catalysis of the hydrogen and oxygen. In another aspect, the method further comprises using an oxygen sensor in fluid communication with the output from the cathode and connected to a processor that determines the amount of oxygen in the output, wherein the processor controls the power to the electrochemical cell based on the amount of oxygen detected and one or more settings for hypoxia training. In another aspect, the method further comprises controlling one or more pumps and valves in fluid communication with the anode and cathode with a processor, wherein the one or more pumps and valves control air flow to and from the cathode, and water flow into the anode, wherein the pumps and valves regulate the reduction in oxygen from ambient air and the air flow to the mask and the conversion of water into oxygen. In another aspect, the method further comprises regulating the temperature of the electrochemical cell by contacting the electrochemical cell with a coolant. In another aspect, the method further comprises regulating oxygen pressure-on-demand, wherein the amount of oxygen removed from the ambient air is reduced by the electrochemical cell based on air intake at the mask, wherein air intake is determined by one or more sensors that monitor breath rate, wherein the one or more sensors are connected to that logic, which logic adjusts the current to the electrochemical stack in real time.

In another aspect, the method further comprises determining how much air is inhaled at the mask with the logic, wherein the logic provides a peak amplitude based on the breath rate, and adjusts a mass flow controller for ambient air intake at the mask. In another aspect, the electrochemical cell comprises a stack of anodes and cathodes. In another aspect, the power supply is defined further as a hybrid power distribution system that limits current draw from an external power source. In another aspect, the method further comprises recovering water with a water recovery system in fluid communication with the cathode, wherein the water in the water recovery system can be at least one of: delivered to the anode, stored, or disposed. In another aspect, the anode catalyst is an Ir—Ru-Ox catalyst with at least one of Au or Pt nanoparticles. In another aspect, the anode catalyst is an Ir—Ru-Ox catalyst with a 5 to 95 mol % Ir to Ru ratio. In another aspect, the anode catalyst is an Ir—Ru-Ox catalyst that further comprises at least one of an Au loading range of 0, 1, 5, 10, 15, 20, 25, 30, 35, 40 wt %, or a Pt loading of from 0, 5, 10, 15, 20 wt %. In another aspect, the cathode further comprises a cathode electrochemical catalyst that reduces oxygen in the ambient air. In another aspect, the cathode has a first and a second side, and the first side is in contact with the proton exchange membrane and the second side is in contact with an air diffusion layer, wherein the air diffusion layer is in contact with the cathode input and output. In another aspect, the anode has a first and a second side, and the first side is in contact with the proton exchange membrane and the second side is in contact with a water flow layer, wherein the water flow layer is in contact with the anode input and output. In another aspect, the electrocatalyst demonstrates a greater than 65%, 70%, 75%, 80%, or 85% water electrolysis efficiency. In another aspect, the method further contacting comprises water with an ion exchange resin prior to contacting with the anode.

In yet another embodiment the present invention includes a system for training a pilot for hypoxia, the system comprising: providing a device to a pilot during hypoxia training that comprises: one or more electrochemical cells each comprising: a cathode and an anode separated by a proton exchange membrane, each of the anode and cathode in communication with an input and an output, wherein the input of the cathode is in fluid communication with ambient air, and wherein the input of the anode is in fluid communication with a source of liquid water; a power supply connected to the one or more electrochemical cells; and a mask in fluid communication with the output from the cathode of the one or more electrochemical cells, wherein oxygen is removed from the ambient air during contact with the cathode when hydrogen ions are separated from liquid water by a catalyst on the anode; and measuring one or more parameters of oxygen use at the mask with one or more sensors connected to a processor, wherein an output from the sensors is processed by a logic in the processor, wherein the processor that controls a current to the one or more electrochemical cells; modulating the amount of oxygen output from the device during operation; and a display connected to the processor, wherein the display provides instructions to the pilot to change one or more parameters selected from at least one of breathing depth, breathing frequency, breathing cadence, muscle tension, suit pressure, or from of oxygen from a non-ambient source.

Another embodiment the present invention includes a device for reducing the amount of oxygen in ambient air comprising: one or more electrochemical stacks comprising: a cathode electrocatalyst, a proton exchange membrane, and an anode electrocatalyst, wherein when power is provided to the one or more electrochemical stacks, the anode electrocatalyst electrolyzes water into protons and oxygen, the protons traverse the hydrogen exchange membrane, and the cathode electrocatalyst reacts the protons with oxygen in ambient air to form water, thereby reducing the amount of oxygen in the ambient air.

The present invention also includes a method for reducing the amount of oxygen in ambient air comprising: electrically powering one or more electrochemical stacks that comprise: a cathode electrocatalyst, a proton exchange membrane, and an anode electrocatalyst; electrolyzing water at the anode electrocatalyst into protons and oxygen, wherein the protons traverse the hydrogen exchange membrane by attraction to the cathode, and reacting oxygen in ambient air with the protons at the cathode electrocatalyst to form water, thereby reducing the amount of oxygen in the ambient air.

In yet another embodiment the present invention includes a gas generator comprising: electrically powering one or more electrochemical stacks that comprise: a cathode electrocatalyst, a proton exchange membrane, and an anode electrocatalyst; electrolyzing water at the anode electrocatalyst into protons and oxygen, wherein the protons are eliminated by traversing the hydrogen exchange membrane by attraction to the cathode and pure oxygen is generated. In another aspect, the generator is connected to a compressor that compresses the oxygen to 0 to 400 psi, 400 to 2200 psi, or 2200 to 3600. In another aspect, the oxygen is concentrated by reacting the protons and electrons transferred to the cathode and reacted with oxygen in the air feed to generate a nitrogen enriched air stream at the cathode side. In another aspect, the nitrogen enriched air is applied to render materials inert. In another aspect, the protons generated are recombined at the cathode into hydrogen gas. In another aspect, the protons generated are recombined at the cathode into compressed hydrogen gas and the oxygen is vented out at ambient pressures. In another aspect, the one or more of the following gases can be detected at the electrocatalyst by measuring changes in pH: nitrous oxides, ammonia, carbon monoxide, or carbon dioxide.

Yet another embodiment of the present invention is a device for hypoxia training comprising: an accumulator in fluid communication with a gas inlet and a back pressure regulator at a first output and a forward pressure regulator at a second output; a conduit connected to an output of the forward pressure regulator that connects to an inlet of a unidirectional valve at a mask, the mask being further connected to a unidirectional output valve; and a pressure sensor in communication with an interior of the conduit, wherein the pressure sensor is connected to and controls the forward pressure regulator to control the flow of gas from the accumulator to the mask.

Another embodiment of the present invention is a method for hypoxia training comprising: providing an accumulator in fluid communication with a gas inlet and a back pressure regulator at a first output and a forward pressure regulator at a second output; connecting a conduit to an output of the forward pressure regulator that connects to an inlet of a unidirectional valve at a mask, the mask being further connected to a unidirectional output valve; and providing a pressure sensor in communication with an interior of the conduit, wherein the pressure sensor is connected to and controls the forward pressure regulator to control the flow of gas from the accumulator to the mask.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention is an electrochemical oxygen separation (EOS) device that is based on liquid water fed electrochemical cells that utilize an advanced and highly efficient oxygen evolution reaction (OER) electrocatalyst. A membrane electrode assembly (MEA), which is one of the components of the electrochemical cell, is used to separate the oxygen from the nitrogen present in the ambient air via a series of electrochemical reactions. Liquid water is fed to the anode compartment of the electrochemical cell, while air is fed to the cathode compartment. At the cathode, oxygen is removed from the air stream resulting in an oxygen depleted stream which is transferred to the pilot trainee via an oxygen mask. At the anode, pure oxygen is formed which is stored in a Douglas bag for subsequent use.

The electrochemical mechanism used to separate oxygen from the air is very accurate and efficient. Therefore, the oxygen concentration may be accurately controlled resulting in simulated altitude from 0 to 30,000 ft. Additionally, the device required no compressed gases, eliminated the logistics chain associated with current devices. The EOS device only required electrical power and a water source to replace water vapor lost to the ambient surroundings.

Figure 1:
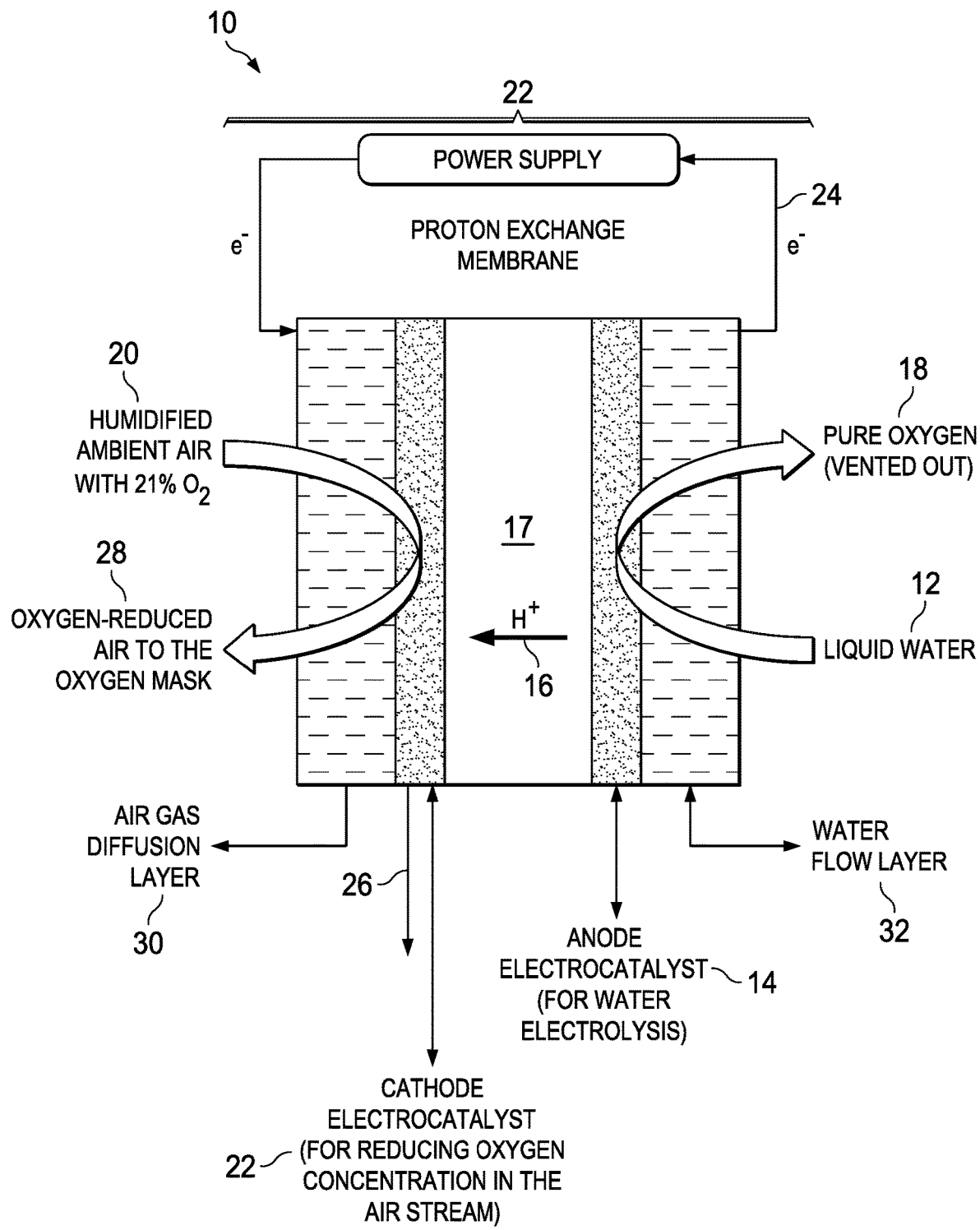
FIG. 1 shows a basic electrochemical operation schematic for the electrochemical oxygen separation of the present invention that generates an oxygen-reduced air for, e.g., hypoxia training for naval pilot trainees.

The basic operation principles of the electrochemical oxygen separator device 10 are shown in FIG. 1 and the corresponding electrochemical reactions are described in Table 1. Liquid water 12 is fed to the anode compartment 14 and water molecules are dissociated into hydrogen protons 16 and oxygen 18 via electrolysis reaction over the anode electrocatalyst (see anode half cell reaction in Table 1). Atmospheric air 20 is fed into the cathode compartment 22 of the electrochemical cell 22. Protons 16 generated at the anode 14 are transported to the cathode side 22 due to the electrical field gradient 24 across a proton exchange membrane 17 and react with the oxygen in the air 20 to generate both water 26 and reduced-oxygen air 28 (this reaction is also known as electrochemical cathode depolarization). The electrochemical cathode 22 depolarization phenomenon lowers the electrochemical device's electrical potential and hence, reduces its power consumption. The reduced-oxygen air stream 28 at the cathode outlet is then transferred to the pilot trainee via an oxygen mask. The pure oxygen 18 generated at the anode is stored in a storage container (e.g., a Douglas bag) during normal operation. However, the pure oxygen anode stream can be made available for mask delivery in the event of a medical emergency. Also depicted in FIG. 1 are an air gas diffusion layer 30 and a water flow layer 32.

TABLE 1

Electrochemical half cell reactions for the electrochemical oxygen separator technology.

Cathode  $4 H^+ + 4 e^- +$ Ambient air with 21% $O_2 \rightarrow 2 H_2O +$ Reduced-oxygen air stream TABLE 1-continued Electrochemical half cell reactions for the electrochemical oxygen separator technology.

| | |
|---|---|
| Anode | $2 H_2O \rightarrow$ Pure $O_2 + 4 H^+ + 4 e^-$ |
| Overall | Reduced-oxygen air stream (cathode outlet to oxygen mask) $\rightarrow$ Pure $O_2$ (anode outlet stored) |

An electrochemical oxygen separator device uses an advanced oxygen evolution reaction (OER) electrocatalyst and feeding the water to the anode side. The efficiency and power consumption of the proposed electrochemical oxygen separator device are mainly governed by the anode electrocatalyst and how the liquid water is fed. The present invention includes the development of an advanced OER electrocatalyst. Since the anode side of the electrochemical oxygen separator uses a water electrolysis reaction, a novel OER electrocatalyst was optimized to provide high efficiencies. The OER electrocatalyst of the present invention demonstrated over 85% efficiency for water electrolysis. In addition, to further improve the efficiency of the electrochemical oxygen separator device, liquid water can be fed directly to the anode side. Flowing the water directly onto the anode electrocatalyst eliminates the reactant mass transfer issues and allows the device to operate at high current densities, which will drastically reduce the mass and volume of the final system.

Figure 2A:
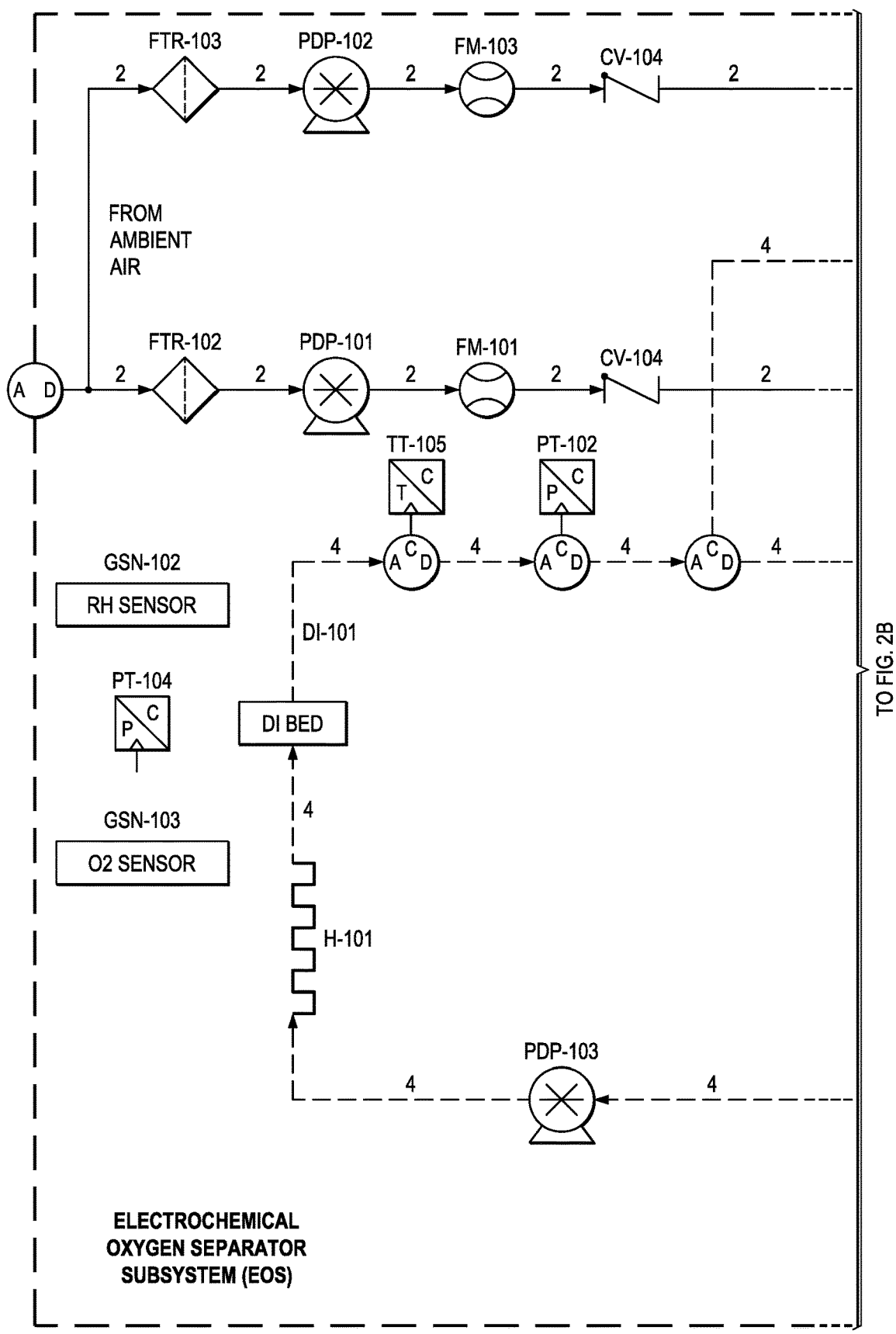
FIGS. 2A to 2E show a basic piping and instrumentation diagram (P&ID) for an electrochemical oxygen separation (EOS) EOS system of the present invention.
Figure 2B:
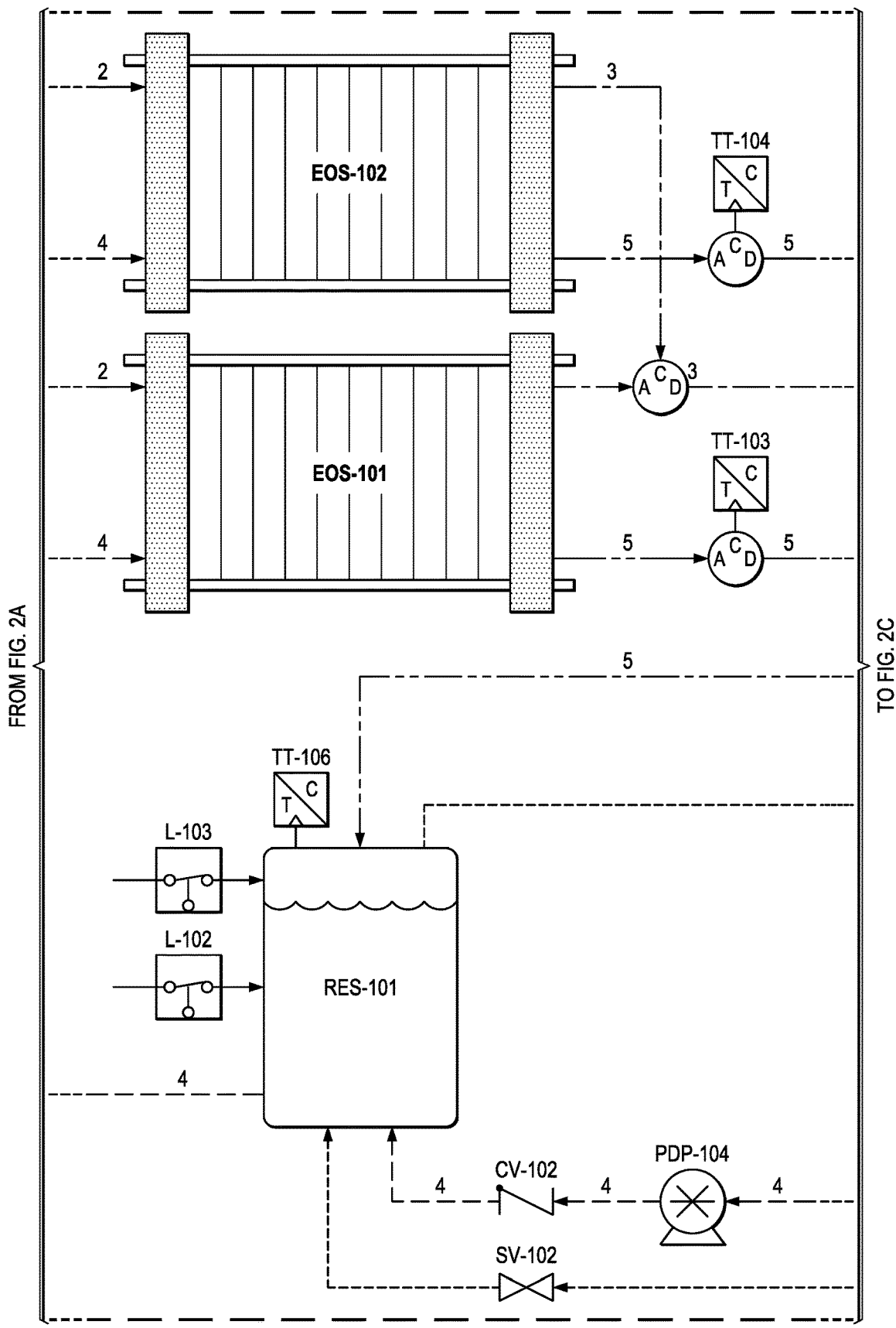

Supporting system for the EOS technology. The electrochemical stack requires supporting Balance of Plant (BOP) components to function. Two basic piping and instrumentation diagrams for use with the present invention are shown in FIGS. 2A to 2E and 3A to 3H. These diagrams show tubing sizes (1-4 denoting ¼", 5/16", ⅜", and ½", respectively) and media type (solid: air; solid/dashed: reduced oxygen air; large dash: water). FIGS. 2A to 2E show a basic piping and instrumentation diagram (P&ID) for an electrochemical oxygen separation (EOS) EOS system of the present invention. For remote operations, air pumps may be needed to pressurize and force the air through the system. Generally, the pressure generated by these air pumps (~10-15 psig) also enables the pressure demand operation discussed in a later section. In FIG. 2A, air can be filtered via particulate filters (FTR-102 & 103 (see FIG. 2E)) before entering the system. Inline check valves (CV-104) ensure that the system remains pressurized in the event of a pump failure. In FIG. 2B, the flow rate from the air pumps is metered via two flow meters (FM-101 & 103). Measuring the amount of air entering the system is important as it defines the amount of oxygen that will need to be removed by the electrochemical stacks (EOS-101 & 102). Likewise, measuring the relative humidity sensor (GSN-102), an ambient air pressure sensor (PT-104), and oxygen sensor (GSN-103) is necessary for accurate production of gases. As previously discussed, the electrochemical stacks are responsible for separating the oxygen from the cathode to the anode. The molar quantity of oxygen separated is directly proportional to the electrical current applied to the stacks. Therefore, accurate control of the applied current results in an accurate control of the oxygen concentration and thus simulated altitude.

Figure 2C:
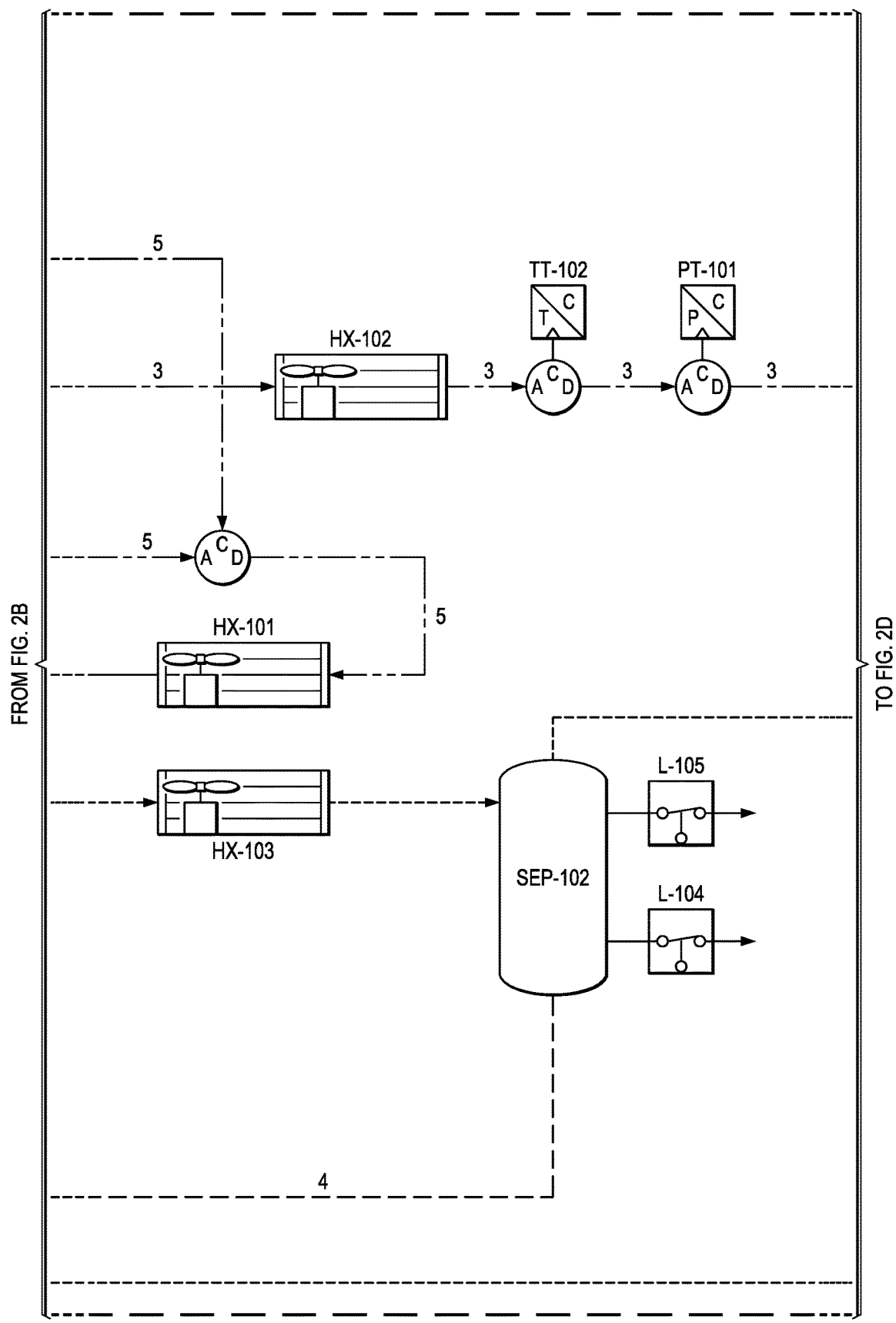
Figure 2D:
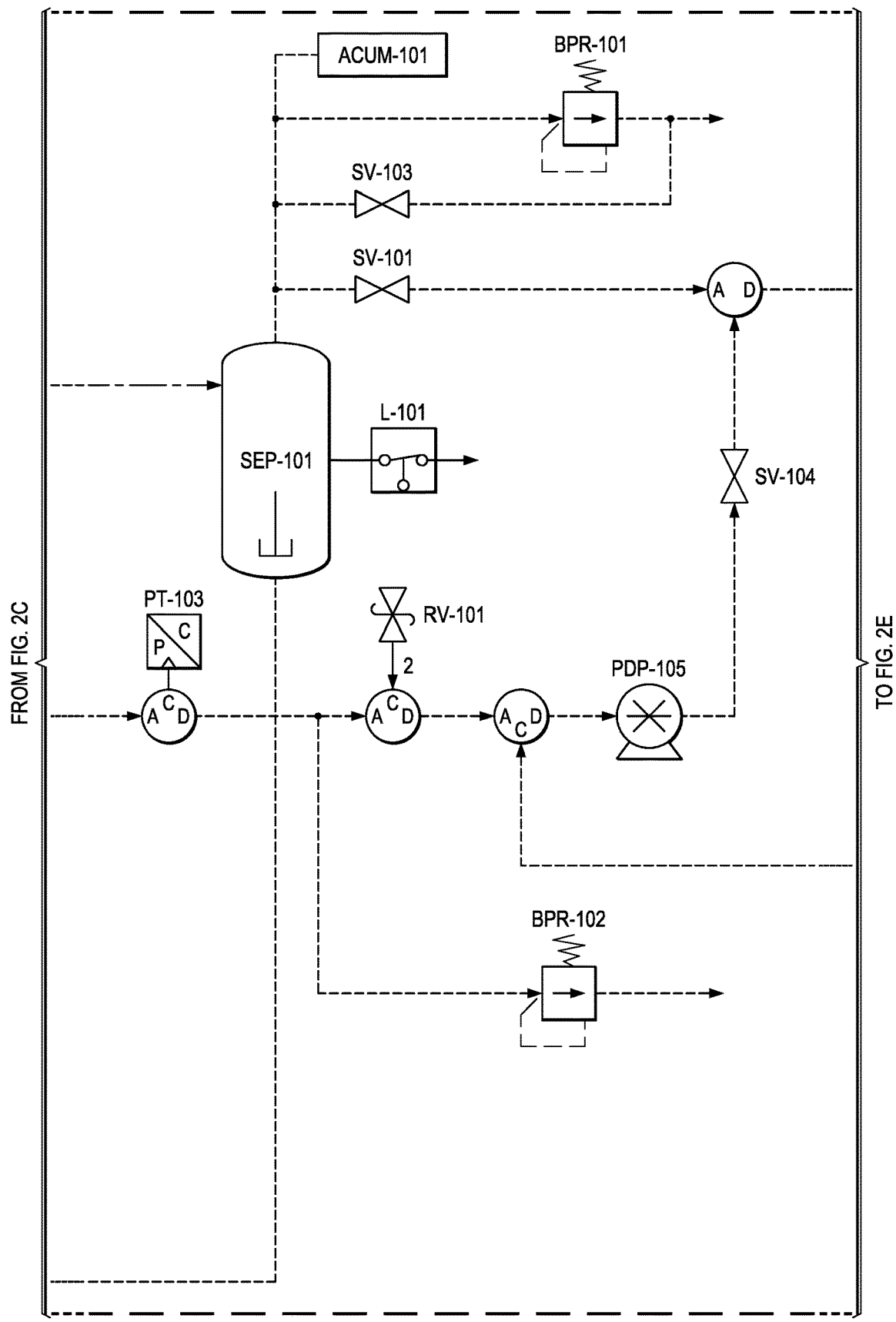

FIGS. 2B and 2C show that, in this version, after the stack, the oxygen depleted cathode stream is cooled back down to room temperature via HX-102 where excess water vapor is condensed. In FIG. 2D, this condensed water is then separated out via SEP-101, which is drained via SV-102 when the collected water volume triggers level sensor L-101. This water is delivered back to the water reservoir (RES-101) in an effort to conserve water. The water level and temperature is monitored by level sensors L-102, L-103, and temperature sensor TT-106. The resulting oxygen depleted cathode air is then collected in an accumulator (ACUM-101) where it is subsequently vented through a back pressure regulator (excess production) (BPR-101), or delivered to the pilot. System pressure can be monitored by pressure transducers (PT-101, PT-103) operated separately or together mounted between the EOS system and accumulator (ACUM-101). Likewise, pilot airstream temperature is monitored by temperature sensor TT-102.

Figure 2E:
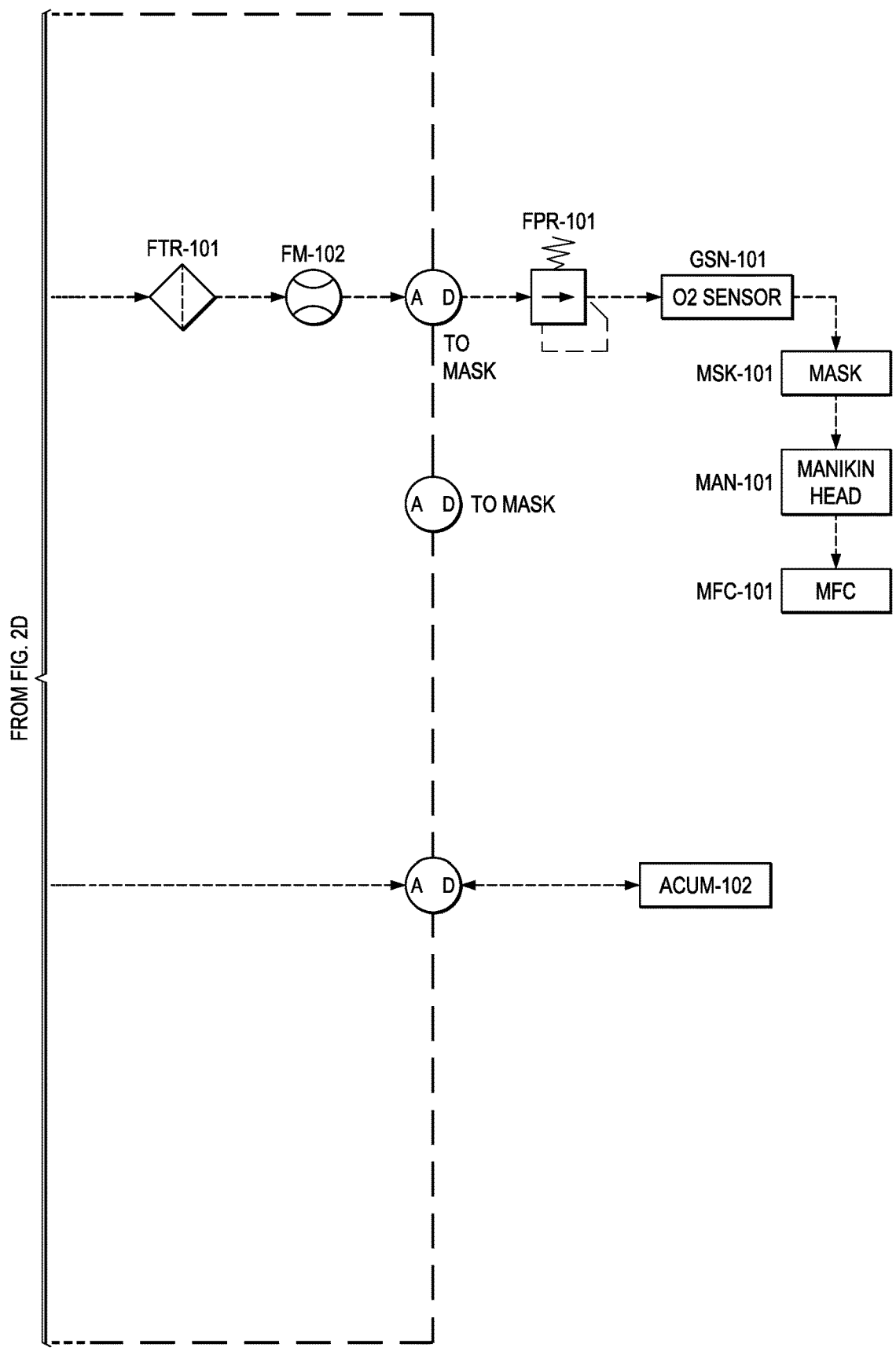

In FIG. 2E, before delivery to the user (e.g., a pilot), the cathode air is first filtered via a particulate filter (FTR-101) and metered with a flow meter (FM-102). The metered flow is used to calculate the pilots breathing rate (slpm), tidal volume and BPM (breaths per minute), which may be data logged for further analysis and/or display. The EOS system of the present invention has the capability to interchange regulators (FPR-101). The regulator is responsible for enabling the mask breathing response. This can be configured for pressure on demand (positive pressure mask which forces air into lungs) or dilution demand (negative pressure mask which required the pilot to pull air into the lungs) functionality. A pilot's mask (MSK-101) is secured to a manikin (MAN-101) which is connected fluidically to a vacuum air line. The breathing profile of a pilot is simulated using MFC-101.

The electrochemical stack can also incorporate a thermal control. This may be accomplished through a re-circulated liquid coolant loop, which is incorporated into the anode of the stack. A water reservoir (RES-101) is filled with de-ionized water (see FIG. 2B). Water is circulated via PDP-103 (see FIG. 2A) through a water heater (H-101, which heats the coolant during startup) and a de-ionization bed (DI-101) before being delivered to the electrochemical stacks. Stack inlet water temperature is monitored by temperature sensor TT-105 which feeds into the control algorithm for the heater, and liquid flow is ensured by positive pressure readings in PT-102. Stack outlet temperature is monitored by temperature sensors TT-104 and TT-103. In addition to a coolant, the water can also humidify the stack, supplying the water needed at the anode for electrolysis. As the electrochemical reactions take place, oxygen is evolved and exits the anode along with the water. The two-phase mixture then passed through an air cooled heat exchanger (HX-101) before dumping back in the water reservoir.

The coolant reservoir also acts as a phase separator, which allows the produced oxygen to escape through a vent at the top. This product oxygen stream then passes through an air-cooled condenser (similar to the cathode stream), which condenses any excess water. The product oxygen stream then flows into a secondary phase separator (SEP-102). The amount of collected water is monitored by level sensors L-104 and L-105, which triggers liquid pump PDP-104 to drain into the water reservoir. CV-102 ensures no backflow of water when the pump is not operational.

In FIG. 2E, the product oxygen stream then vents into an optional storage container (e.g., a Douglas bag (ACUM-102)) where it is stored at 10" $H_2O$ for subsequent use. If the storage container is not installed, or if the storage container has filled to capacity, the product oxygen vents through the pack pressure regulator BPR-102. When the pilot becomes hypoxic, an oxygen dump feature may be enabled which will deliver pure oxygen to the pilot (if the Douglas bag is present) or 50% concentrated oxygen to the pilot by mixing ambient air pulled through relief valve RV-101 (if the storage container is not installed).

When the oxygen dump mode is enabled, the cathode stream is closed (by closing SV-101, FIG. 2D), while the anode stream is opened (by opening SV-104, FIG. 2D). This allows oxygen to be pulled from the anode (or the storage container if installed) and delivered to the pilot via the oxygen delivery pump (PDP-105, FIG. 2D).

Figure 3A:
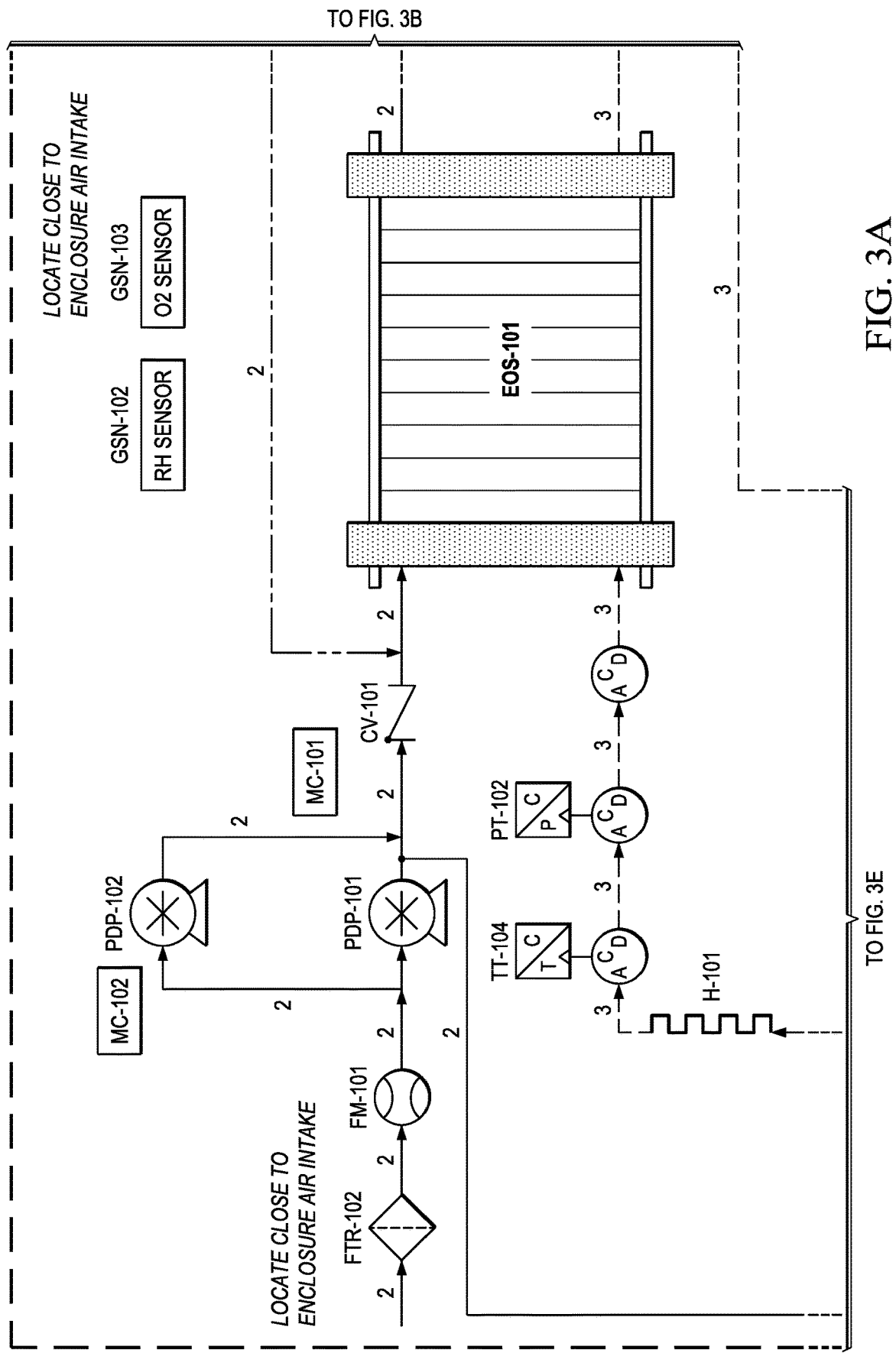
FIGS. 3A to 3H show another basic piping and instrumentation diagram (P&ID) for another EOS system P&ID of EOS system of the present invention.

FIG. 3A to 3H shows another basic piping and instrumentation diagram (P&ID) of EOS system P&ID of EOS system. In FIG. 3A, for remote operations, an air pump may be needed to pressurize and force the air through the system via PDP-101. Generally, the pressure generated by this air pump (~10-15 psig) enables the pressure demand operation discussed in a later section. Pressure in the range ~20-40 psig is also generally used. Piston Air Pumps (such as Thomas by Gardner Denver 22201230INTLSCX pumps) can be used for PDP-101 and PDP-102, their associated motor controllers (MC-101 and MC-102) regulate the speed based on desired outlet flow rate. Air can be filtered via particulate filters (FTR-102) before entering the system. The flow rate from the air pumps is metered via flow meters (FM-101), e.g., using a MEMS flow sensor FS4000 mass flow sensor. Measuring the amount of air entering the system is important as it defines the amount of oxygen that will need to be removed by the electrochemical stack (EOS-101). Likewise, measuring the relative humidity and ambient air pressure (GSN-102 and GSN-103) is necessary for accurate production of gases. A single electrochemical stack is preferred in this embodiment, with the single air pump (PDP-101) forcing air through the system. A check valve (CV-101) on the inlet of the stack ensures stack pressure is maintained in the event of a pump failure.

As previously discussed, the electrochemical stack is responsible for separating the oxygen from the cathode to the anode. The molar quantity of oxygen separated is directly proportional to the electrical current applied. Therefore, accurate control of the applied current results in an accurate control of the oxygen concentration and thus simulated altitude.

Figure 3B:
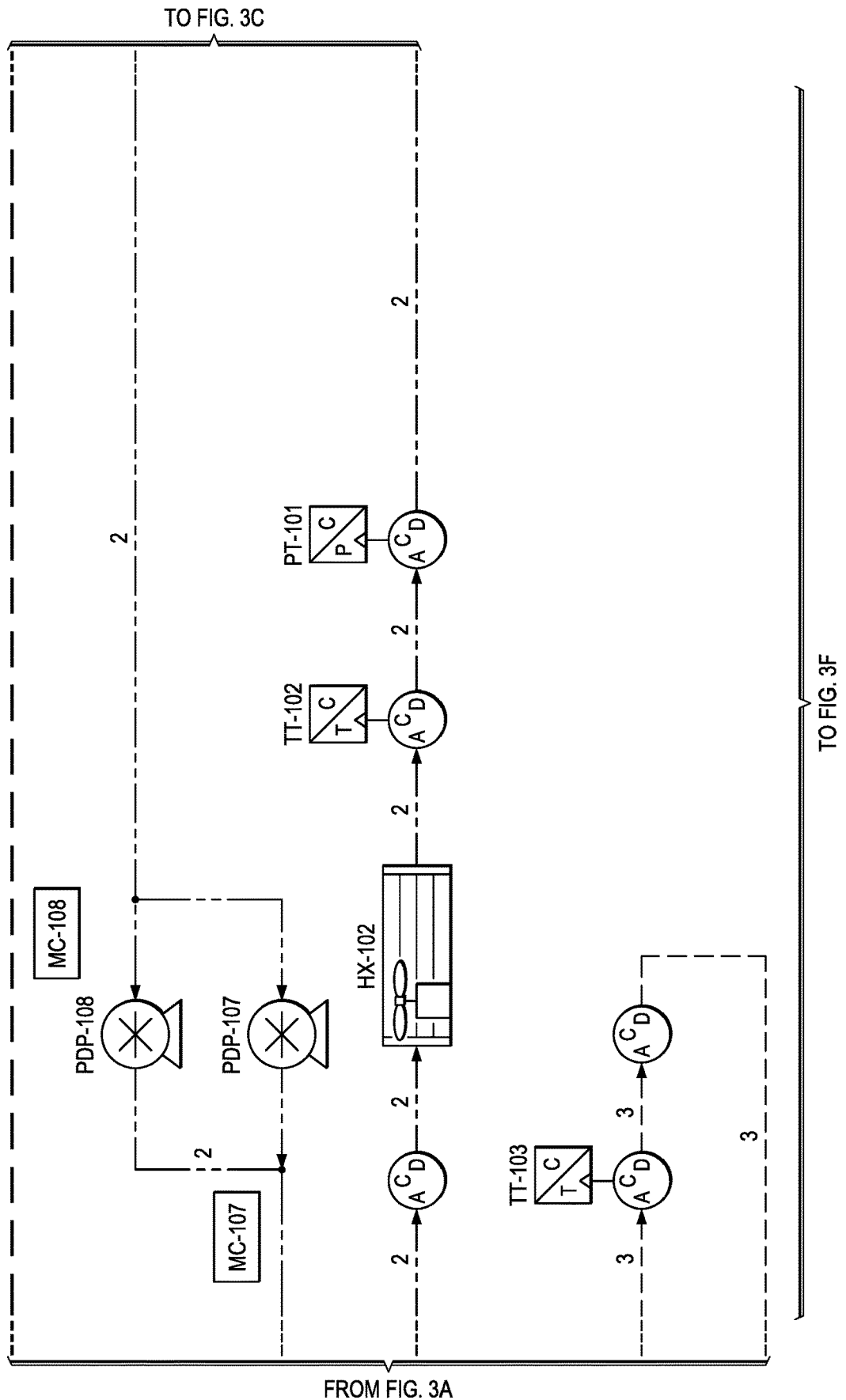

In FIG. 3B, in this version, after the stack, the oxygen depleted cathode stream is cooled via HX-102 where excess water vapor is condensed. This embodiment allows for some of the oxygen depleted air from electrochemical stack (EOS-101) outlet on the cathode side, to be returned back to the stack's air inlet. Return of oxygen depleted air is via ACUM-101 (FIG. 3C) and recirculation pumps PDP-108 and PDP-107. These pumps are under variable control motor controllers (MC-107 and MC-108) so to allow the amount of gas returning to the inlet to be varied. The pumps may also be operated at a fixed pumping rate. Suitable pumps include Servoflo's D10K micro diaphragm pump, 1420VDP Thomas diaphragm pumps, also Air Squared scroll compressor can be used. The return air loop is implemented for the purposes of reducing water build up in the cathode compartments of the stack. Thereby excess air enters the cathode compartments to remove excess water, controlling "flooding" of the cathode electrode structure. This maintains electrochemical efficiency of the stack and reduces oxygen separation, and hence altitude fluctuations over time.

Figure 3C:
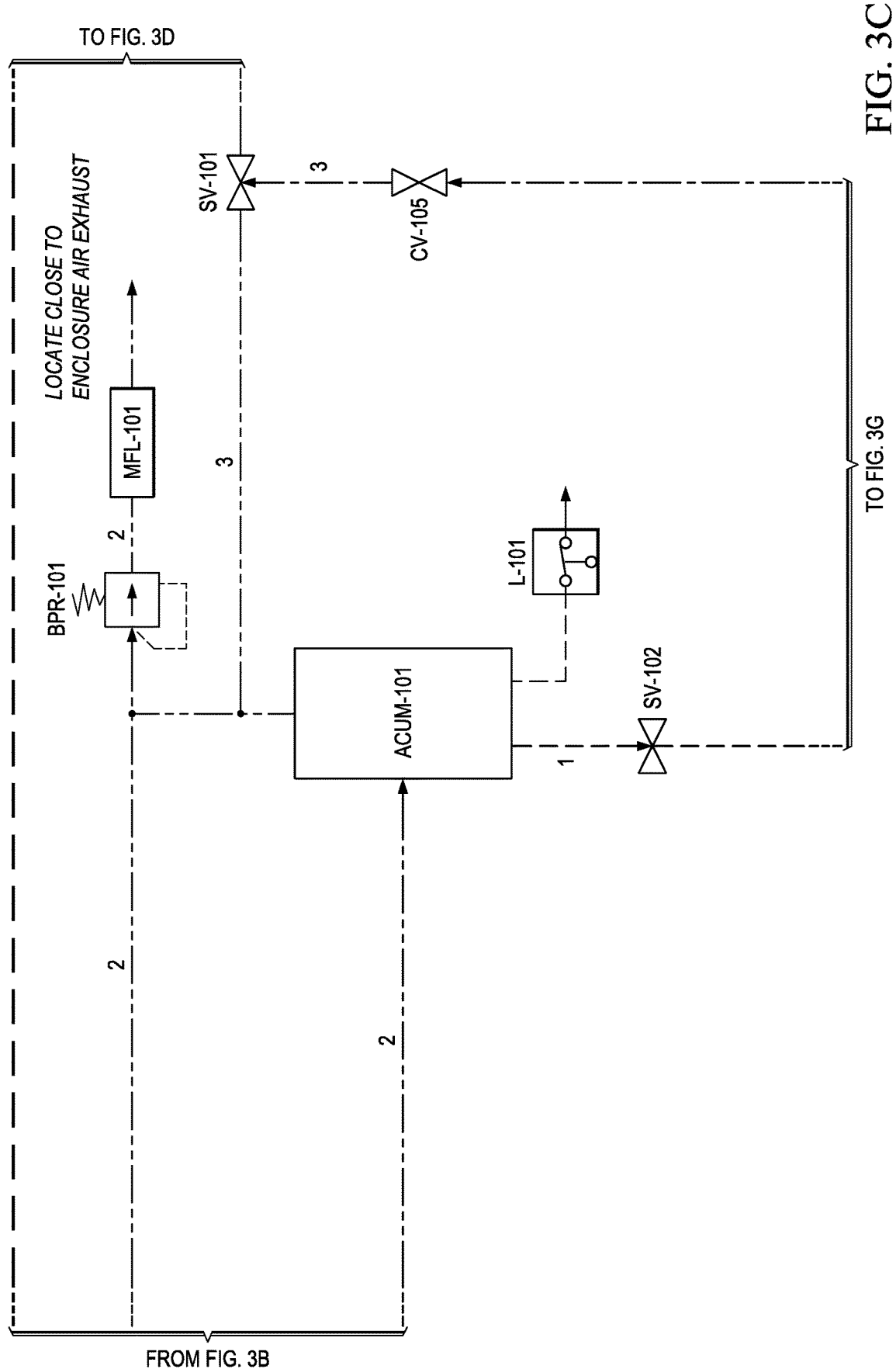
Figure 3D:
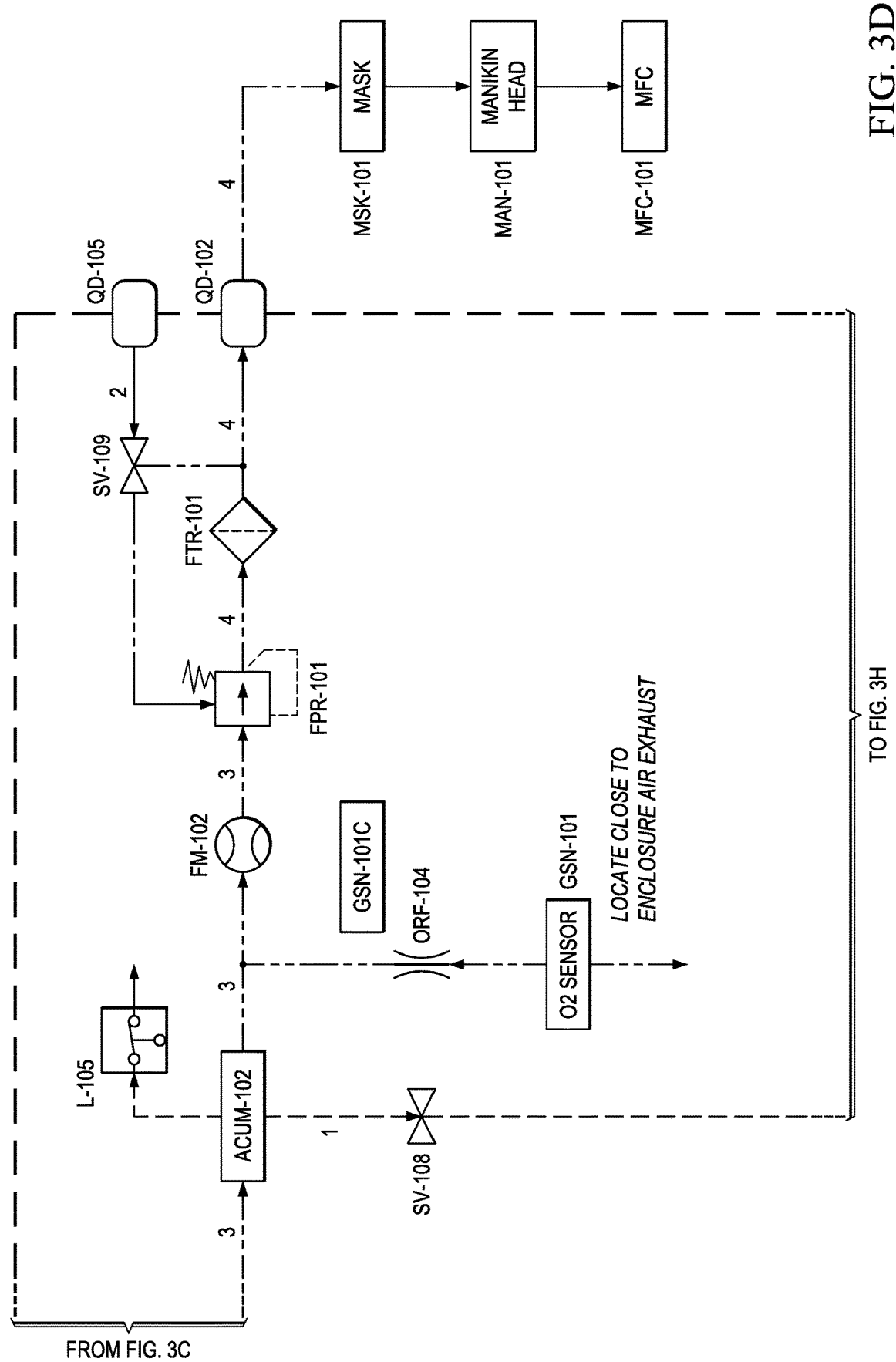
Figure 3E:
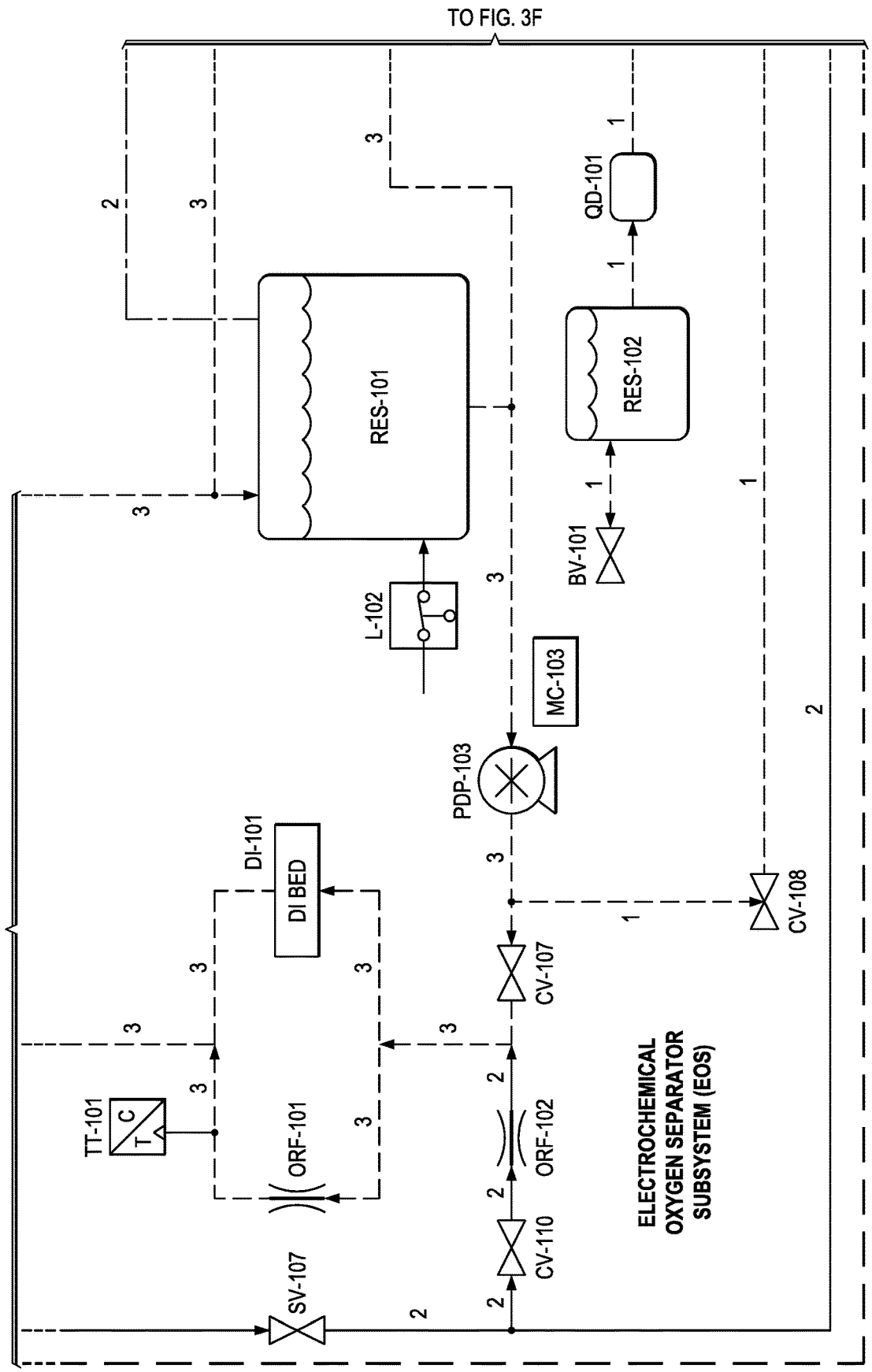

As shown in FIGS. 3C and 3E, this condensed water is then separated out via ACUM-101. The collected liquid water is captured and delivered back to the electrochemical stack via RES-101 in an effort to conserve water. Water is determined via a level sensor (L-101). Water is recovered via PDP-104, then via HX-101 and into container (RES-101). The water is monitored by level sensor L-102 then fed from container RES-101 into the electrochemical stack via PDP-103.

The resulting oxygen depleted cathode air is then collected in an accumulator (ACUM-101) where excess production is subsequently vented through a back pressure regulator (BPR-101) and inline muffler (MFL-101), or delivered to the pilot. A suitable back pressure regulator is the Airtrol RV-5300 Miniature Relief Valve. A pressure relief valve or a back pressure regulator could be used for this purpose. System pressure and temperature can be monitored by pressure transducer (PT-101) and thermocouple TT-102 mounted in the conduit between the EOS-101 system and accumulator (ACUM-101).

BPR-101 is used to set the system pressure, or to be more exact it sets the system upper pressure limit. System pressure is here defined as the pressure in the system (conduits and fixtures) that are positioned between and pressure pump (PDP-101) and the pressure regulator (FPR-101). The internal cathode compartments of the stack EOS-101 are included in this zone. The pump PDP-101 pushes against the pressure set by BPR-101.

As shown in FIG. 3D, cathode air is delivered to the pilot via accumulator (ACUM-102). Water in the accumulator is determined by a level sensor (L-105). Water is recovered for conservation purposes via PDP-104, then via HX-101 and into container (RES-101), involving valve SV-108. Before delivery to the user (e.g., a pilot), the cathode air is first filtered via a particulate filter (FTR-101) and metered with a flow meter (FM-102). Suitable flow meters include MEMS flow sensor FS1015 CL Mass Flow Sensors. The metered flow is used to calculate the pilots breathing rate (slpm), tidal volume and BPM (breaths per minute), which may be data logged for further analysis and/or display. Prior to being delivered to the pilot, the oxygen content of the air is diverted (ORF-104) and measured using an oxygen sensor (GSN-101) and its associated sensor control board GSN-101C.

In FIG. 3D, the EOS system of the present invention has the capability to interchange regulators (FPR-101). The forward pressure regulator (FPR-101) is responsible for enabling the delivery of oxygen-depleted air according to the user's breathing actions. This can be configured for pressure on demand (positive pressure mask which forces air into lungs) or dilution demand (negative pressure mask which required the pilot to pull air into the lungs) functionality. FPR-101 responds to changes in pressure in the conduit between ACUM-102 and the pilot mask, in response to the users breathing activity. It can do this by referencing internal pressure measurements near FTR-101 or external measurements near MSK-101 using SV-109 and QD-105.

As shown in FIG. 3E, the electrochemical stack can also incorporate a thermal control. This may be accomplished through a re-circulated liquid coolant loop, which is incorporated into the anode of the stack. A water reservoir (RES-101) is filled with de-ionized water. The water in this loop is circulated via PDP-103 and fed through a one-way check valve (CV-107), then a de-ionization bed (DI-101) and flow control orifice (ORF-101) that are in parallel. This maintains the water conductivity at levels that protect the stack from ionic corrosion. Heater H-101 heats the coolant during startup and maintains temperature throughout operation using feedback from TT-101, TT-104, and TT-103. Liquid flow is ensured by positive pressure readings in PT-102. A separate loop exists for thermal management in which water is pushed through an air-cooled heat exchanger (HX-101) by liquid pump and pump speed controller PDP- 106 and MC-106, respectively. CV-109 ensures no backflow when the pump is intermittently off. The system must manage a drain and refill cycle. To accomplish this, a small liquid pump (PDP-104) and a series of solenoid valves (SV-104, SV-105 and SV-107) function to add or remove water from the liquid loops as necessary. Pressure supplied by PDP-101, regulated by ORF-102 & ORF-103, helps push water through drain lines. These loops are drained into a removable bottle (RES-102) which interfaces with a double shutoff quick disconnect (QD-101). RES-102 is equipped with a bi-directional valve (BV-101) that allows air passage in an out of the bottle as the water level changes. Finally, check valves CV-110 and CV-111 supply one-way pressure to the drain loop to perform these functions. In addition to a coolant, the water can also humidify the stack, supplying the water needed at the anode for electrolysis. As the electrochemical reactions take place, oxygen is evolved and exits the anode along with the water. The two-phase mixture then passed through an air cooled heat exchanger (HX-102) before dumping back in the water reservoir (RES-101).

Figure 3F:
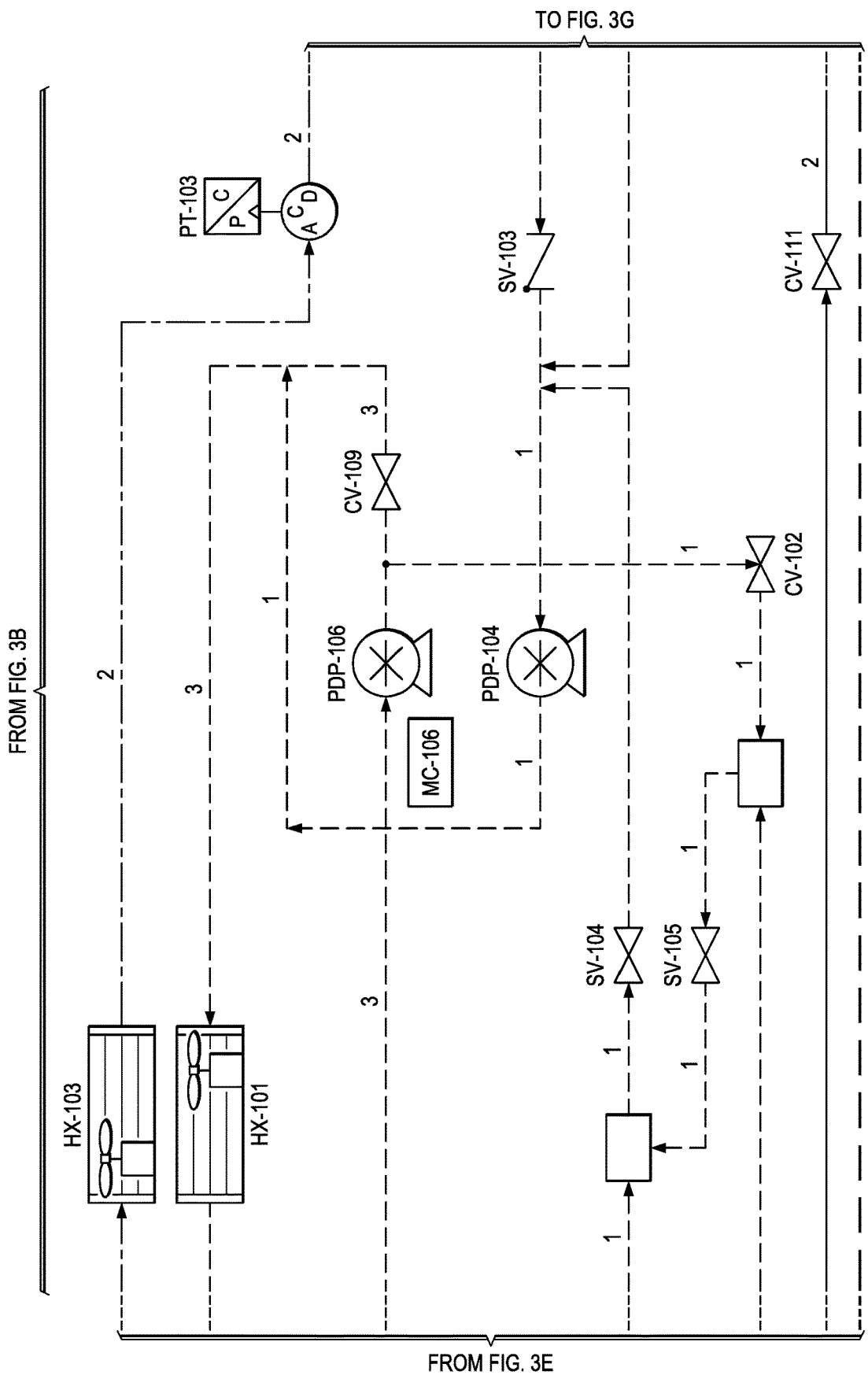
Figure 3G:
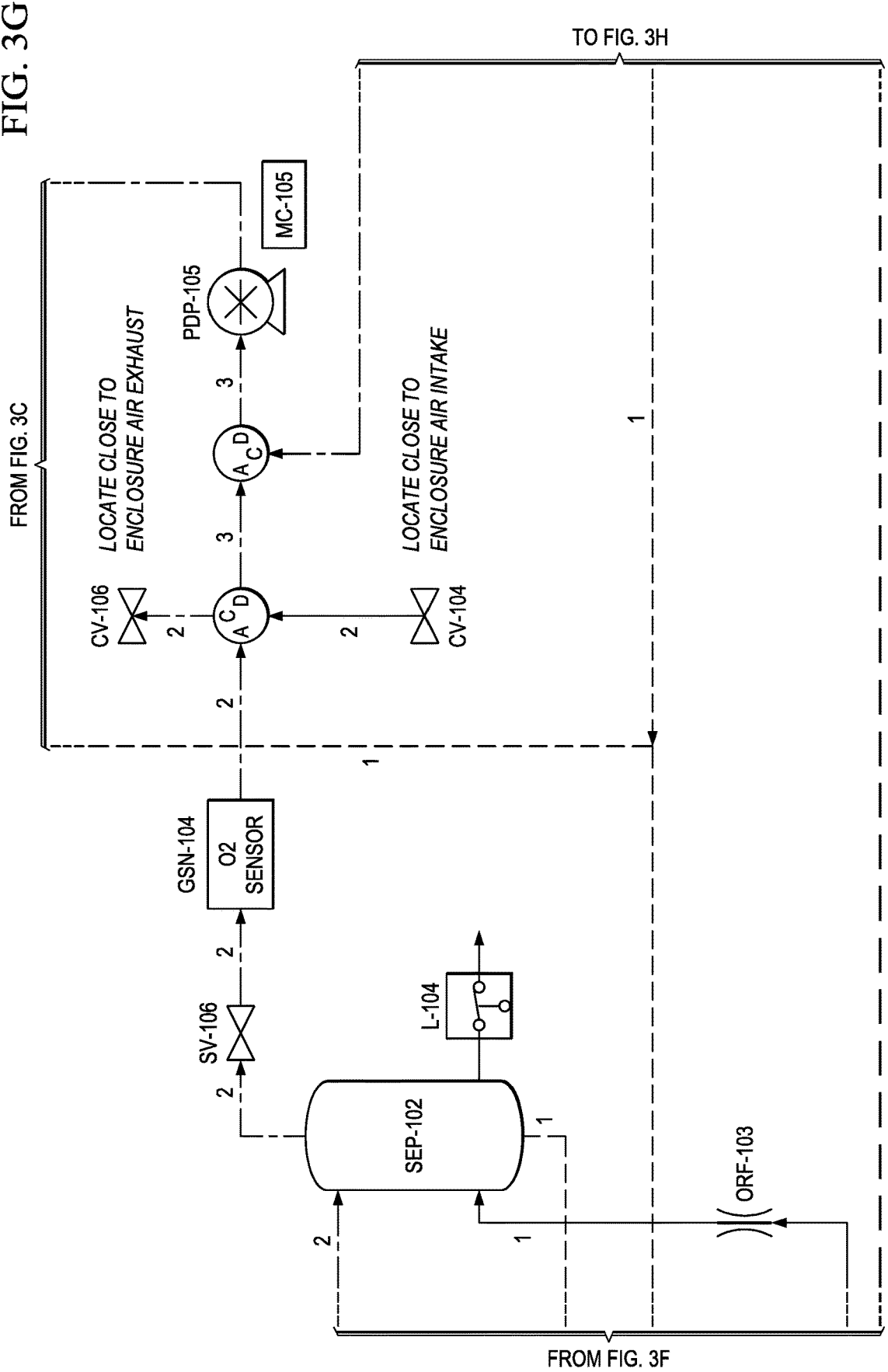

As shown in FIGS. 3F and 3G, the coolant reservoir also acts as a phase separator, which allows the produced oxygen to escape through a vent at the top. This product oxygen stream then pass through an air-cooled condenser (similar to the cathode stream), which condenses any excess water (HX-103). The product oxygen stream then flows into a secondary phase separator, which recycles the water (SEP-102), which is delivered back to the coolant reservoir.

Figure 3H:
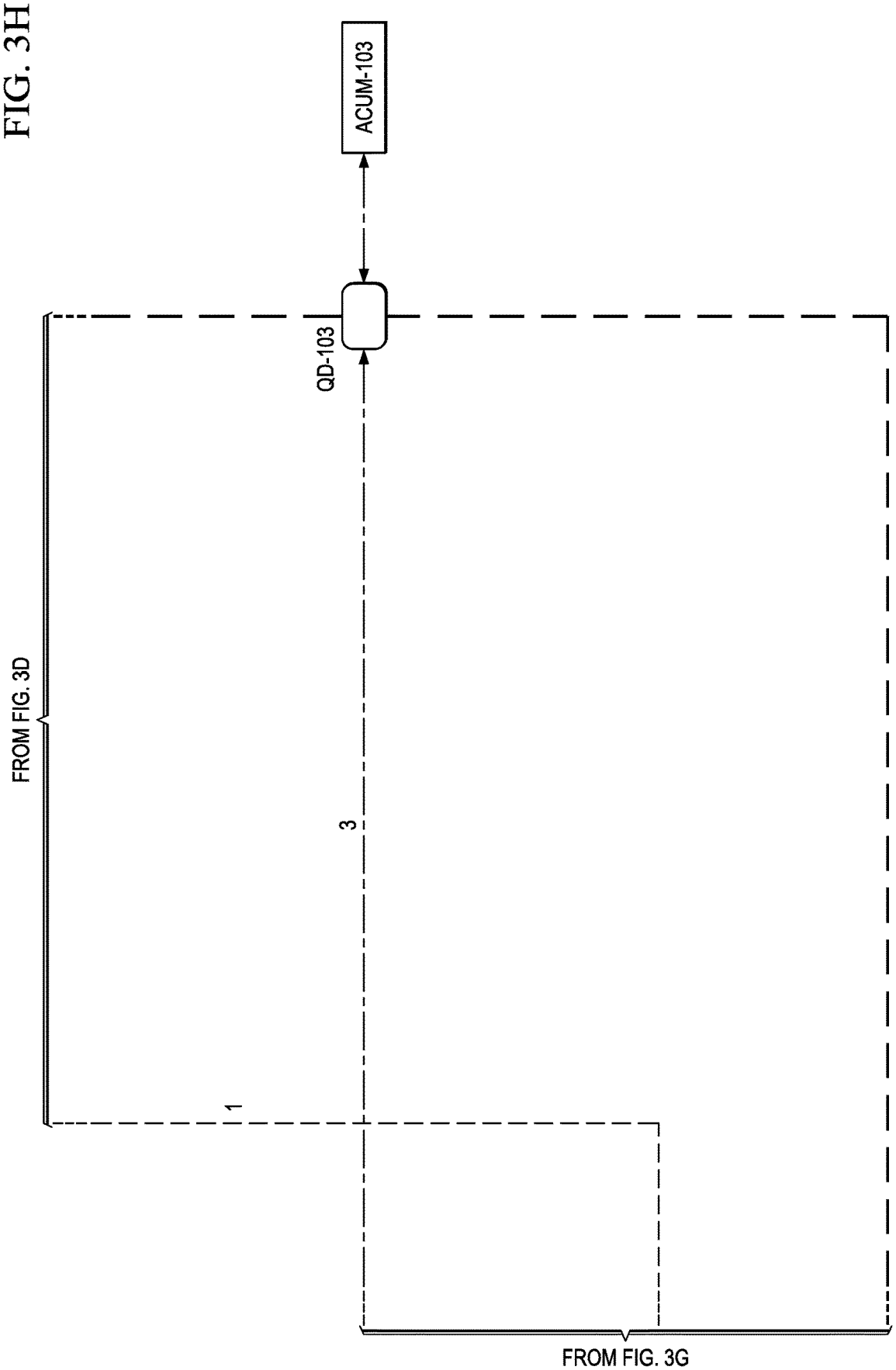

As shown in FIG. 3H, the product oxygen stream then vents into an optional storage container (e.g., a Douglas bag (ACUM-103)) where it is stored at ~10" $H_2O$ for subsequent use. If the storage container is not installed, or if the storage container has filled to capacity, the product oxygen vents through a pressure relief valve (CV-106). When the pilot becomes hypoxic, an oxygen dump feature may be enabled which will deliver pure oxygen to the pilot (if the Douglas bag is present) or ~50% concentrated oxygen to the pilot (if the storage container is not installed) by mixing ambient air pulled through relief valve CV-104.

When the oxygen dump mode is enabled, the cathode stream is closed (by closing SV-101, FIG. 3C), while the anode stream is opened (by opening SV-104, FIG. 3F). This allows oxygen to be pulled from the anode (or the storage container if installed) and delivered to the pilot via the oxygen delivery pump (PDP-105 and MC-105, FIG. 3F).

Figure 4:
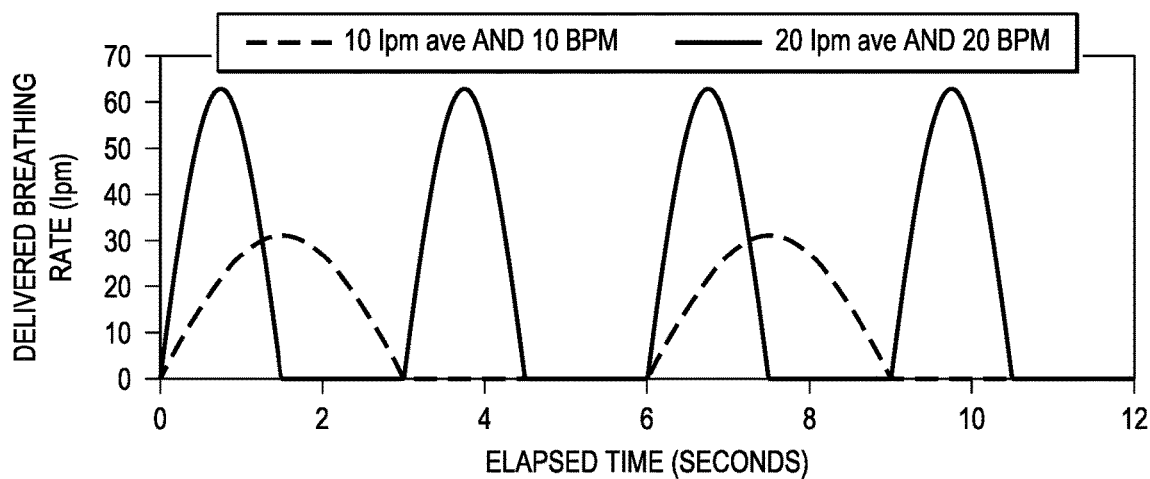
FIG. 4 shows an example of approximated clipped sine wave breathing profiles as delivered to the pilot. For an average flow rate of 10 and 20 liters per minute (lpm), the peak instantaneous flow rate is 31.4 and 62.8 lpm respectively (Average flow rate times Pi).

Using an electrochemical separation approach to produce reduced oxygen air for hypoxia training. Pressure on demand generation feature within the hypoxia device. Human breathing can be approximated by a sine wave at a frequency of 10 to 20 BPM (Breaths per Minute) and an average flow rate of ~10-20 lpm. For example, the aviation masks currently used by the military have exhaust valves resulting in a unidirectional flow of gas going to the pilot. This results in an apparent clipped sine wave being delivered to the pilot with peak instantaneous flow rates up to 62.8 lpm (FIG. 4). Additionally, it is not uncommon for larger individuals to breathe significantly more than this.

However, the EOS stacks of the present invention perform better while producing a constant flow rate of simulated altitude breathing gas. In order to avoid grossly over sizing the system for maximum instantaneous flow rates, the EOS system can be designed with a pressurized accumulator sized to dampen the breathing waveform.

Figure 5:
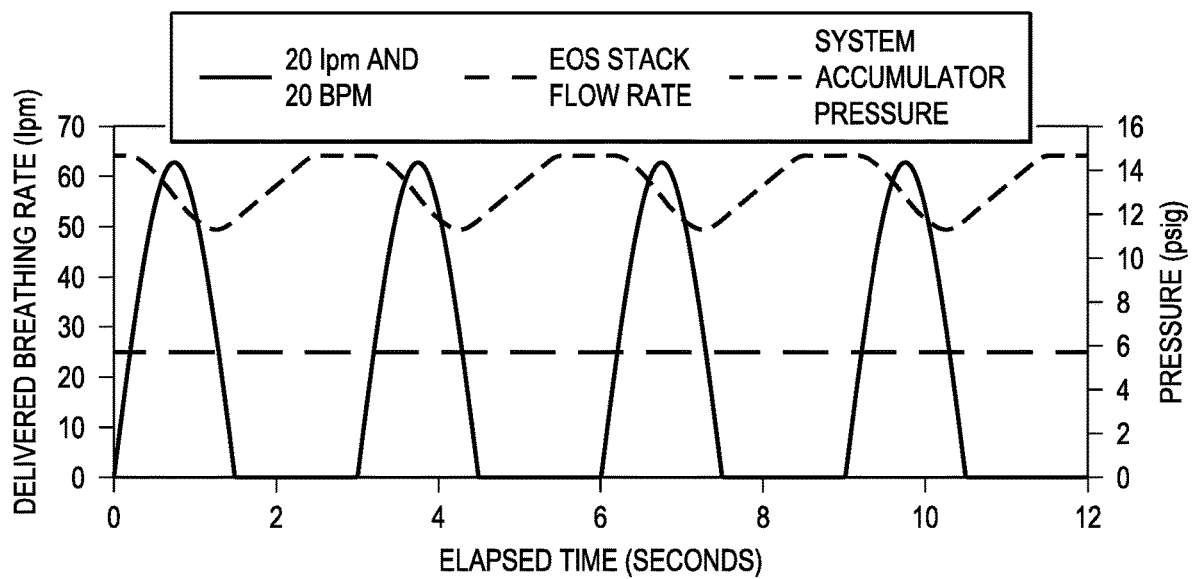
FIG. 5 shows a simulated breathing waveform of 20 lpm & 20 breaths per minute (BPM) delivered by the EOS system of the present invention. Based on an accumulator size of 2 Liters and a constant gas production rate of 25 lpm, the system accumulated pressure oscillated by only 4 psid while maintaining a minimum system pressure of 10 psig at all times.

FIG. 5 demonstrates the performance of EOS system of the present invention while operating at a maximum system pressure of 15 psig and accumulator volume of 2 Liters. An average breathing rate of 20 liters per minute (lpm) with peak instantaneous rate of over 60 lpm are delivered to the pilot with a constant production rate of 25 lpm from the EOS stacks. System accumulator pressure is maintained within 4 psid and never falls below a threshold of 10 psig, insuring that air starvation will not be an issue.

The electrical power consumed by the EOS system of the present invention is primarily related to the air production rate. Therefore, at average flow rates of 30,000 ft simulated air the device power can exceed what a typical 120 vac/15 amp receptacle can provide. Since breathing rates vary from pilot to pilot, a pressure demand based production algorithm was developed that enables the EOS system of the present invention to only produce the flow rate required based on the demand of the pilot.

The flow rate required based on the demand of the pilot is enabled by the use of intelligent pressure and flow rate feed back to the EOS stack and air pumps. Average accumulator pressure and delivered flow rates are monitored to detect increases in pilot demand. The two air pumps are then ramped up in proportion to meet this demand (maintaining flow rate and accumulated pressure). As the air pumps ramp up, additional flow is detected by the inlet flow meters, which trigger a rise in the electrochemical stack current. These relations effectively ramp the production up or down to meet the demand of the pilot while maintain accurate simulated altitude control and preventing air starvation.

Advanced OER (Oxygen Evolution Reaction) Electrocatalyst. The Need for Advanced Anode Electrocatalyst for Electrochemical Hypoxia Device.

Table 1 (above) describes the anode and cathode electrochemical reactions occurring in the electrochemical hypoxia device. While from a thermodynamic perspective, electrolysis of water at anode and reduction of oxygen at cathode side of EOS should be occurring at the same electrical voltage, but due to use of two completely different medium (liquid medium at anode and gaseous medium at cathode), different surface reactions generate different polarizations (change in the equilibrium potential of an electrochemical reaction) and hence observation of different polarization overpotentials. In the electrochemical hypoxia device, oxygen evolution reaction is more sluggish compared to oxygen reduction reaction due to its higher activation overpotential values. Higher overpotential values mean that system is experiencing inefficiencies. The most promising route to reduce the inefficiencies is to lower the activation overpotentials and electrocatalyst component plays the most critical part in achieving lower overpotentials.

Microstructure and chemical composition of the electrocatalyst usually govern the experimentally observed overpotential values (i.e., inefficiencies). How strongly the reaction intermediates bound to the electrocatalyst's surface and how fast the reaction kinetics would be usually governed by the microstructure and chemical composition of the electrocatalyst. The present invention includes a nanoparticle surface modification process for anode electrocatalyst that reduced the binding energies of reaction intermediates to the anode electrocatalyst surface and hence increased reaction kinetics. Enhancing how fast the reactions occurring at the anode significantly improved the electrical efficiencies.

Mechanistic Investigation of OER and Potential Electrocatalysts. OER in aqueous solutions in the water electrolysis reaction, represented by anode reaction of hypoxia device, proceeds always at metal oxide $Me_xO_y$ covered metal electrodes, the anodic overpotential usually exceeding 0.2 V. The OER is supposed to proceed according to the so-called Krasilch'shikov mechanism, in which unstable, overoxidized metal oxide sites are self stabilizing by mutual redox or disproportionation reactions by release of molecular oxygen (schematically described by Equation 1 thru 3) with regeneration of the lower valent metal oxide:

$$Me_xO_y + H_2O \rightarrow Me_xO_yOH + H^+ + e^- \quad (1)$$

$$Me_xO_yOH \rightarrow Me_xO_{y+1} + H^+ + e^- \quad (2)$$

$$2Me_xO_{y+1} \rightarrow 2Me_xO_y + O_2 \quad (3)$$

This mechanistic interpretation is based on the observation, that searching for a volcano-like correlation for activities of OER catalysts, the activity for OER is simply based on the free enthalpy of formation of the overoxidized metal oxide catalyst sites—namely the free enthalpy of formation of the higher oxide from the stable metal oxide. The maximum activity, the tip of the volcano, is observed, where the equilibrium potential for the lower valent and higher valent metal oxides (which can be calculated from the Gibbs-enthalpy of the oxidation reaction of the metal oxide) matches that of the equilibrium potential of the oxygen electrode (+1.23 V vs. RHE). On this basis, $IrO_2$ and $RuO_2$ electrocatalysts were found to be the best metal oxides for OER, sitting at the top of the volcano plot (overpotential vs. enthalpy of oxidation), while PtO exhibits slightly higher overpotentials. Literature supports high catalytic activity of $IrO_2$ for OER, while there have been number of studies based on physically mixed $IrO_2$ and $RuO_2$ as OER catalysts. Surface decoration of nanoparticles is a well-known process in the industry, but most of the time application of the wrong materials does not provide the expected results. It is important that optimal decoration materials are identified and loaded on the base material with the appropriate composition in order to observe the synergetic effects between different elements. In order to demonstrate the efficiencies that can be gained with hypoxia device, the present inventors investigated a series of materials in a very systematic approach and identified the right microstructure with the optimal chemical composition that was needed for anode electrocatalyst. Details of these electrocatalysts and their electrochemical performance in the hypoxia device are provided in the following sections.

Advanced OER Catalyst Manufacturing and Characterization Protocols. A high temperature (450° C.) method was used to prepare these mixed Ir—Ru oxides (Adams 1923). The method is based on oxidation of metal oxide precursors (generally metal halides) in a molten salt (sodium nitrate) environment. The weight ratio of molten salt component to mixed oxide precursor in the method was set to 20 (i.e., X20 protocol). When the weight ratio of molten salt to oxide precursors was 40, it was named as X40 protocol and if the ratio was 10, then it was called X10 protocol. To optimize the Ir and Ru molar ratio, following compositions were prepared:

TABLE 2

Ir to Ru Molar Ratios that were Investigated in Phase I.

| Catalyst ID | Iridium mole fraction | Ruthenium mole fraction |
| --- | --- | --- |
| $IrO_x$ | 100% | 0% |
| $Ir_3RuO_x$ | 75% | 25% |
| $IrRuO_x$ | 50% | 50% |
| $IrRu_3O_x$ | 25% | 75% |
| $Ir_{15}Ru_{85}O_x$ | 15% | 85% |

TABLE 2-continued

Ir to Ru Molar Ratios that were Investigated in Phase I.

| Catalyst ID | Iridium mole fraction | Ruthenium mole fraction |
| --- | --- | --- |
| $Ir_{10}Ru_{90}O_x$ | 10% | 90% |
| $Ir_5Ru_{95}O_x$ | 5% | 95% |
| $RuO_x$ | 0% | 100% |

Electrochemical characterization of the electrocatalyst samples included collecting OER potentiodynamic curves and EIS spectra in 0.5 M $H_2SO_4$ electrolyte with a VMC VersaStat potentiostat from PAR. Synthesized catalysts were also evaluated for the anodic oxygen evolution reaction in a single cell anode liquid water fed electrolyzer having a 25 $cm^2$ active area using a Fideris Hydrogen Test Station modified for electrolyzer use. The electrolyzer membrane electrode assembly (MEA) had 4 $mg/cm^2$ Pt black as cathode catalyst and 4 $mg/cm^2$ of the corresponding mixed Ir—Ru oxide as the anode catalyst. Nafion ionomer was used on both the anode (45 vol % loading) and cathode (70 vol % loading). Performance of the single cell was tested at 75° C. with no backpressure. Electrolyzer i-V curves were taken for each catalyst and the performances was compared to determine optimum Ir to Ru molar ratio.

After optimizing the chemical composition of Ir—Ru mixed oxide, the effects of synthesis temperature and synthesis protocol parameters were investigated. Some of the mixed Ir—Ru oxides with different molar ratios from Table 2 were synthesized at 550 and 450° C. In addition, the effect of chemical components' weight ratio in the Adam's synthesis protocol was explored. Currently, the weight ratio of molten salt to Ir—Ru oxide precursors was set to 20. Molten salt to Ir—Ru precursors' weight ratios of 40 and 10 were investigated.

Next, an Ir—Ru oxide catalyst was selected for Pt and Au loading optimization. Au loadings of 1, 5, 10, 20, 30, and 40 wt % were investigated. Pt loadings of 1, 5, 10, and 20 wt % were investigated. Initially, optimal loadings of Au and Pt were determined individually. After identification of the optimal loading for each surface modifier, combined Pt—Au binary surface modification was examined. For the binary nanoparticles, the following synthesis route was explored: the gold was reduced on the mixed oxide first, then, platinum a reduction was conducted. Then, the effect of Nafion loading in the anode catalyst layer on the electrolyzer performance was studied with the optimized catalyst. Currently, 45 vol % Nafion ionomer is used for the anode catalyst layer. Loadings of 33, 40, 47, and 61 vol % Nafion ionomer were investigated to optimize the anode ionic conductivity without increasing overall electrical resistance.

Figure 6:
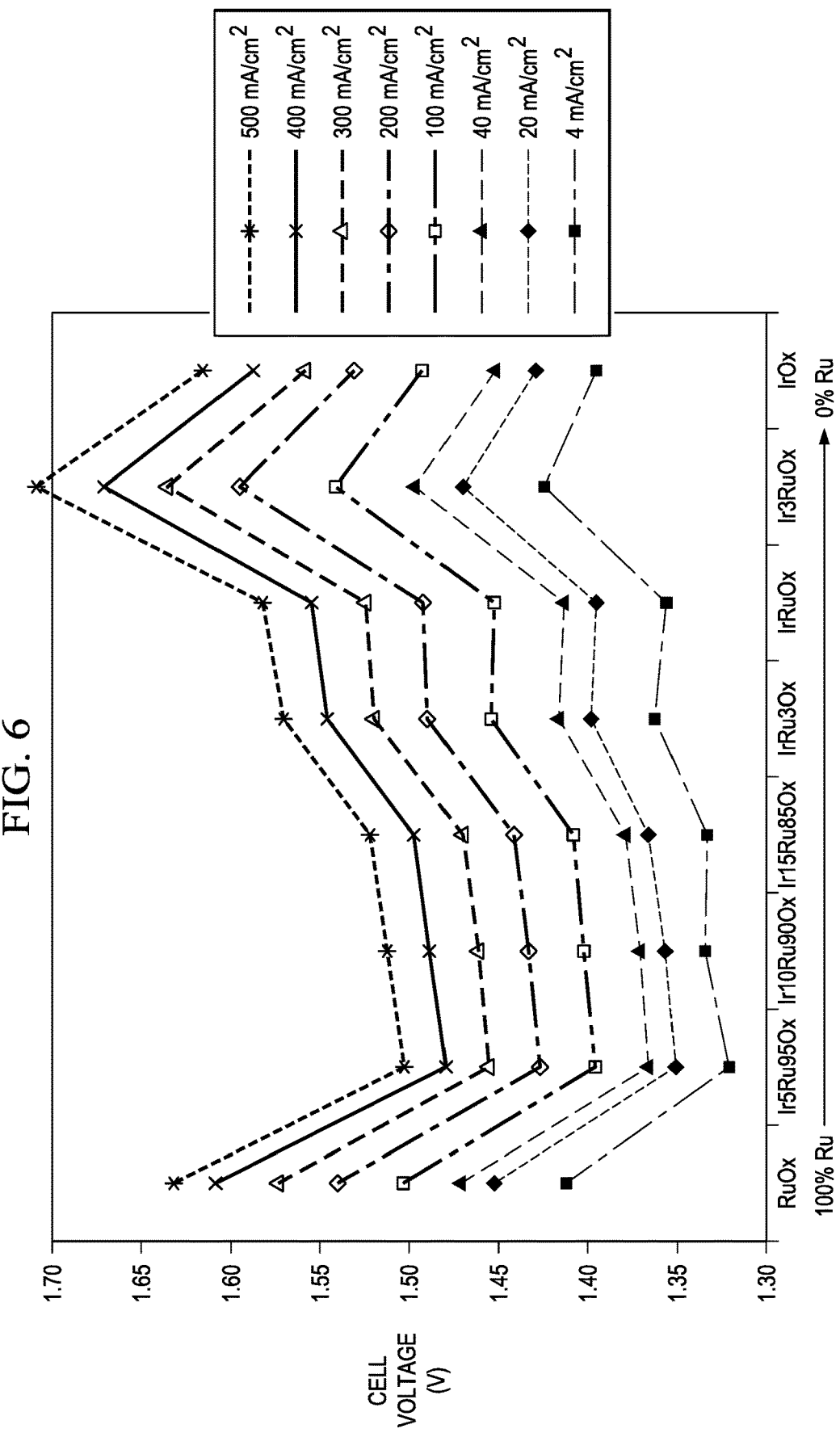
FIG. 6 shows the cell potential as a function of the chemical composition at specific current densities for catalysts synthesized at 550° C., X20 protocol (for Ir to Ru molar ratio optimization). $Ir_5Ru_{95}O_x$ (5 to 95 mol % of Ir to Ru ratio) catalyst demonstrated the best performance. $Ir_5Ru_{95}O_x$ catalyst provided a cell voltage of 1.428 V at 200 mA/cm$^2$ was obtained with five-mil thick Nafion membrane (86.13% efficiency) at a 75° C. cell temperature in the anode-fed mode. No backpressure.
Figure 7:
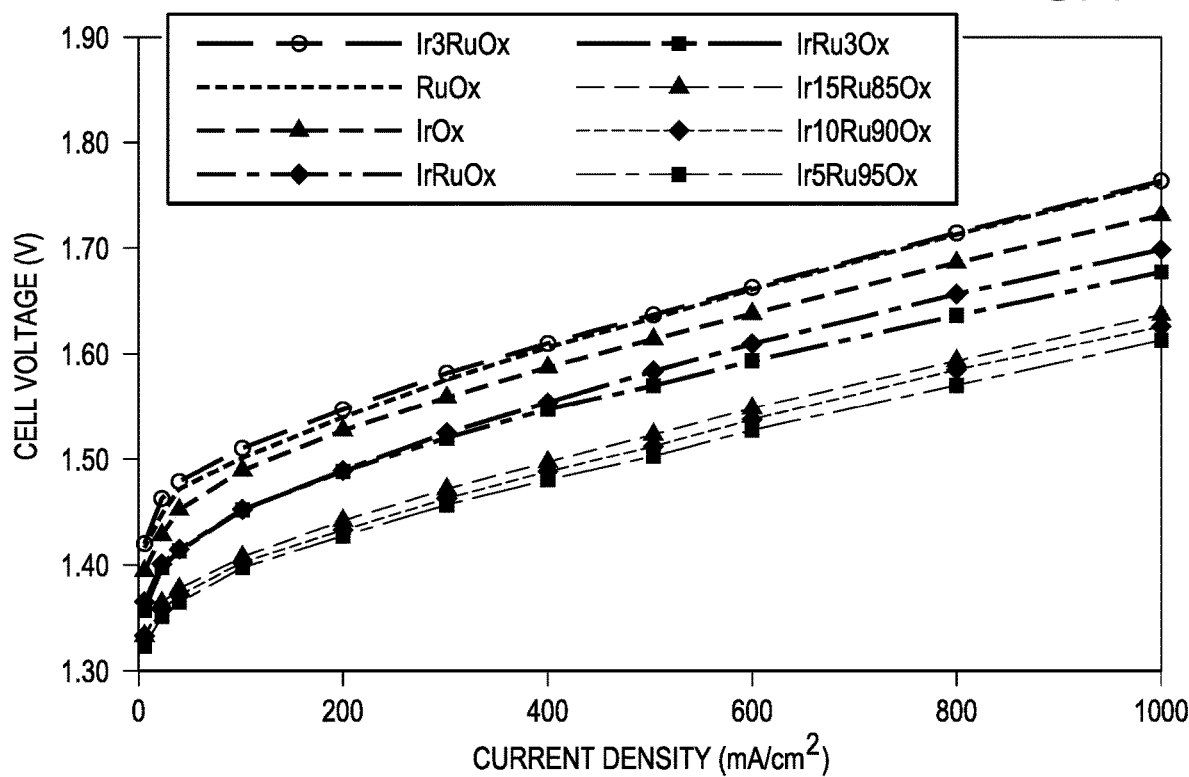
FIG. 7 shows results from a single cell for catalysts synthesized at 550° C., X20 protocol (for Ir to Ru molar ratio optimization). $Ir_5Ru_{95}O_x$ (5 to 95 mol % of Ir to Ru ratio) catalyst demonstrated the best performance; a cell voltage of 1.398 V at 200 mA/cm$^2$ was obtained with five-mil thick Nafion membrane at a 75° C. cell temperature in the anode-fed mode. No backpressure.

Optimization of the iridium to ruthenium molar ratio. To identify the optimal Ir to Ru molar ratio for the mixed oxide, catalyst samples listed in Table 2 were synthesized at 550° C. using the X20 protocol. Synthesized catalysts were electrochemically characterized in a single cell with five-mil thick Nafion membrane (from DuPont) at 75° C. and zero backpressure. The single cell results are given in FIGS. 6 and 7. $Ir_5Ru_{95}O_x$ (5:95 mol % of Ir to Ru ratio) catalyst demonstrated the best electrolysis performance. $Ir_5Ru_{95}O_x$ catalyst provided a cell voltage of 1.428 V at 200 mA/$cm^2$, which corresponds to an efficiency of 86.13%.

While there are several electrocatalysts that can be used for anode side of hypoxia device, the most efficient ones would be based on the mixtures of $IrO_2$ and $RuO_2$ materials. While $IrO_2$ has excellent corrosion resilience for hypoxia device, it has higher overpotential compared to $RuO_2$. On the other hand, $RuO_2$ is highly active as a electrocatalyst, it does not possess the electrochemical stability for hypoxia device. While this patent is not limited to the following compositions, but it is preferred to have 0 to 95 mol % of $RuO_2$ (with the balance being $IrO_2$) in order to have both excellent electrocatalytic activity and good electrochemical stability in an electrochemical hypoxia device. More preferably, 50 to 95 mol % of $RuO_2$ (with the balance being $IrO_2$) in order to further improve the electrochemical stability and good catalytic activity, even more preferably, 75 to 95% mol % of $RuO_2$ (with the balance being $IrO_2$) for the best electrochemical activity and satisfactory corrosion resistance.

Figure 8:
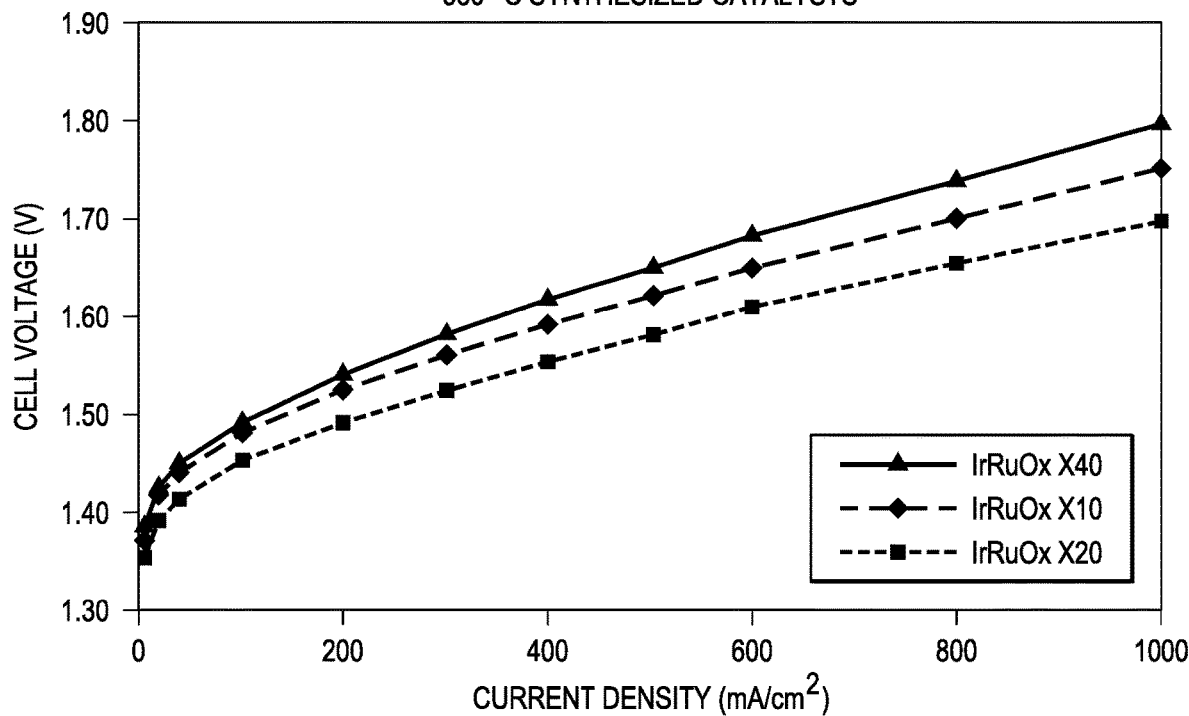
FIG. 8 shows results from a single cell for IrRuOx catalysts synthesized at 550° C. with X10, X20, and X40 protocols (synthesis protocol optimization). IrRuOx catalyst that was synthesized with X20 protocol demonstrated the best performance with five-mil thick Nafion membrane at a 75° C. cell temperature in the anode-fed mode. No backpressure.

Effect of synthesis protocol and synthesis temperature and optimization of these parameters. The synthesis protocol effect was investigated with IrRuOx catalyst (1:1 molar ratio of Ir to Ru) as a baseline. IrRuOx catalysts were synthesized at 550° C. with three different synthesis protocols, namely X10, X20, and X40 protocols. Single cell results are given in FIG. 8. The catalyst sample that was synthesized with X20 protocol demonstrated the best performance.

While this patent is not limited to the following weight ratio of oxidizer salt to metal oxides for the synthesis, in certain embodiments it may be preferred to have 5 to 40 fold in excess of oxidizer salt (compared to the weight of the metal oxide), in other embodiments 10 to 35 fold in excess of oxidizer salt (compared to the weight of the metal oxide), and in other embodiments a 20 to 30 fold in excess of oxidizer salt (compared to the weight of the metal oxide).

Figure 9:
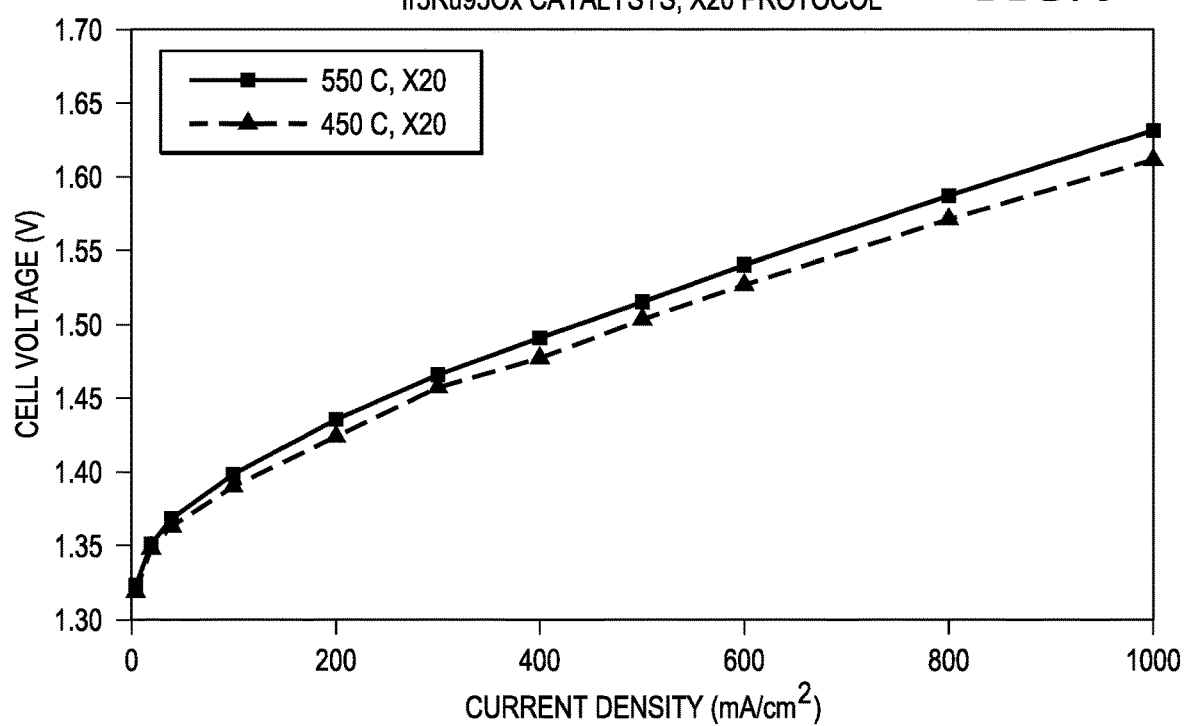
FIG. 9 shows results from a single cell for $Ir_5Ru_{95}O_x$ catalysts synthesized with X20 protocol at 450 and 550° C. temperatures (synthesis temperature optimization). $Ir_5Ru_{95}O_x$ catalyst that was synthesized at 450° C. temperature demonstrated the best performance with five-mil thick Nafion membrane at a 75° C. cell temperature in the anode-fed mode. No backpressure.

After the optimal molar ratio and optimal synthesis protocol parameters were identified, the effects of synthesis temperature were investigated. $Ir_5Ru_{95}O_x$ catalyst samples were synthesized via X20 protocol at 450 and 550° C. temperatures and the single cell results are given in FIG. 9. $Ir_5Ru_{95}O_x$ catalyst that was synthesized at 450° C. demonstrated higher performance than the 550° C. synthesized catalyst sample.

In terms of synthesis temperature, while this patent is not limited to the following temperature ranges, it is preferred to have 300 to 550 C, more preferably 400 to 500 C, even more preferably, 440 to 460 C in order to get the best electrocatalytic activity for mixed metal oxide material.

Optimization of the platinum and gold loading (surface decoration of mixed metal oxide material). After identifying the optimal molar ratio, synthesis protocol and synthesis temperature parameters, Pt and Au loading optimization was carried out. Platinum decoration of metal oxides generates a downshift of the d-band center of Pt atoms and this prevents strong adsorption of surface species to the electrocatalyst surface. A more weakly bound surface species may be more reactive to form $O_2$ than a more strongly bound one, resulting in a rate enhancement for $O_2$ evolution. Obviously, a weak binding of surface adsorpbed reactive oxygen species and a weak adsorption of $O_2$ on Pt surfaces of the deposited Pt/metal oxide electrode can decrease the coverage of the surface species and increase available active sites for water dissociation, leading to higher catalytic activity for OER on the deposited catalyst than on pure Pt or on the physically mixed Pt/metal oxide catalyst. Au was used to stabilize the Pt particles for the high potential application for anodic OER.

Pt and Au nanoparticle surface modification was investigated with individual species first to identify the optimal loading value for each platinum and gold alone. Then, the combined optimal platinum-gold loading on $Ir_5Ru_{95}O_x$ was verified. The Au loading range was from 0 wt % to 40 wt % with the Pt loading range from 0 wt % to 20 wt %. All $Ir_5Ru_{95}O_x$ catalyst samples were synthesized at 450° C. using the X20 protocol.

Figure 10:
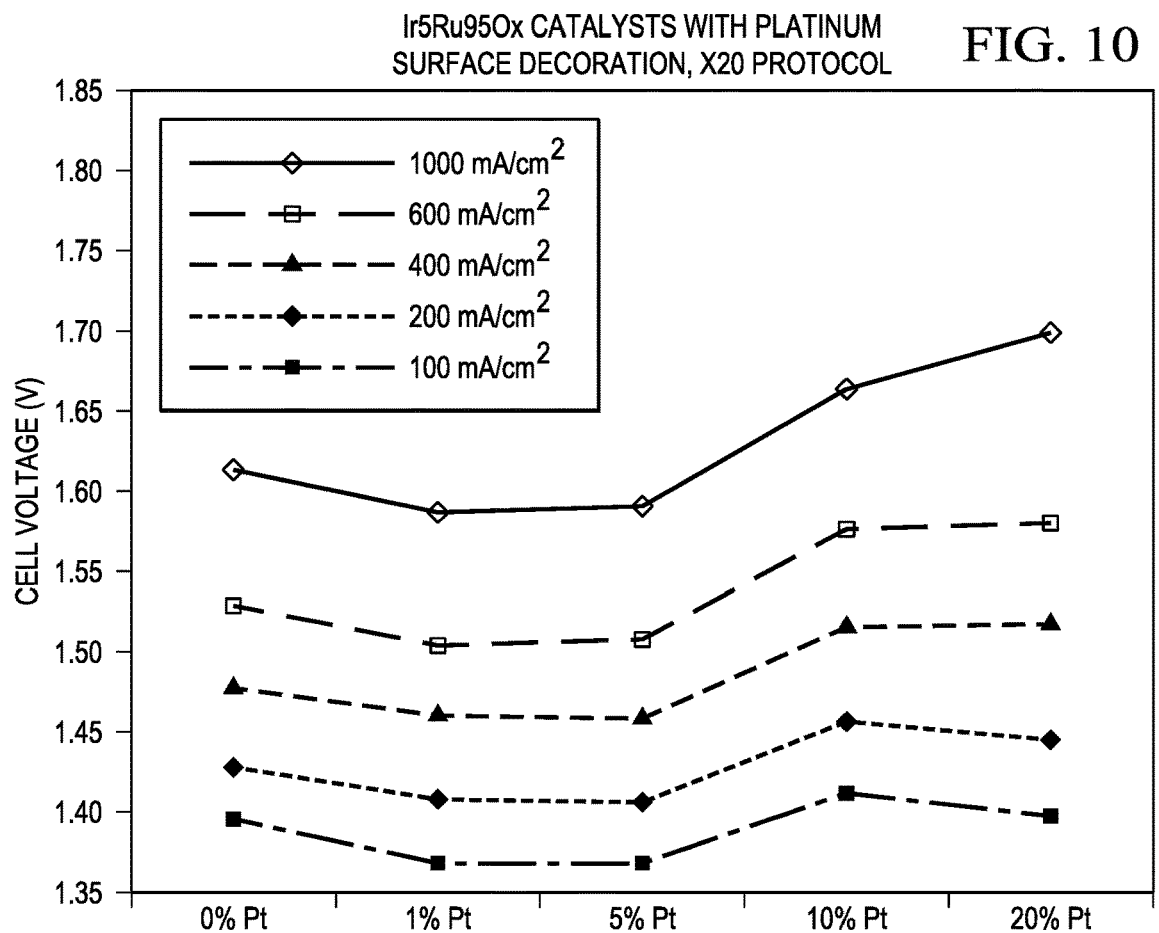
FIG. 10 shows the cell potential as a function of the Pt loading on $Ir_5Ru_{95}O_x$ catalyst at specific current densities (for Pt loading optimization). The Pt loading range tested was from 0 wt % to 20 wt %. Pt nanoparticles were decorated on the surface of the $Ir_5Ru_{95}O_x$. $Ir_5Ru_{95}O_x$ catalysts synthesized with X20 protocol at 450° C. temperature. $Ir_5Ru_{95}O_x$ catalyst with 1 wt % Pt surface modification demonstrated the best performance with five-mil thick Nafion membrane. A 1 wt % Pt nanoparticle surface modification provided a cell voltage of 1.406 V at 200 mA/cm$^2$ (87.48% efficiency) at a 75° C. cell temperature in the anode-fed mode. No backpressure.
Figure 11:
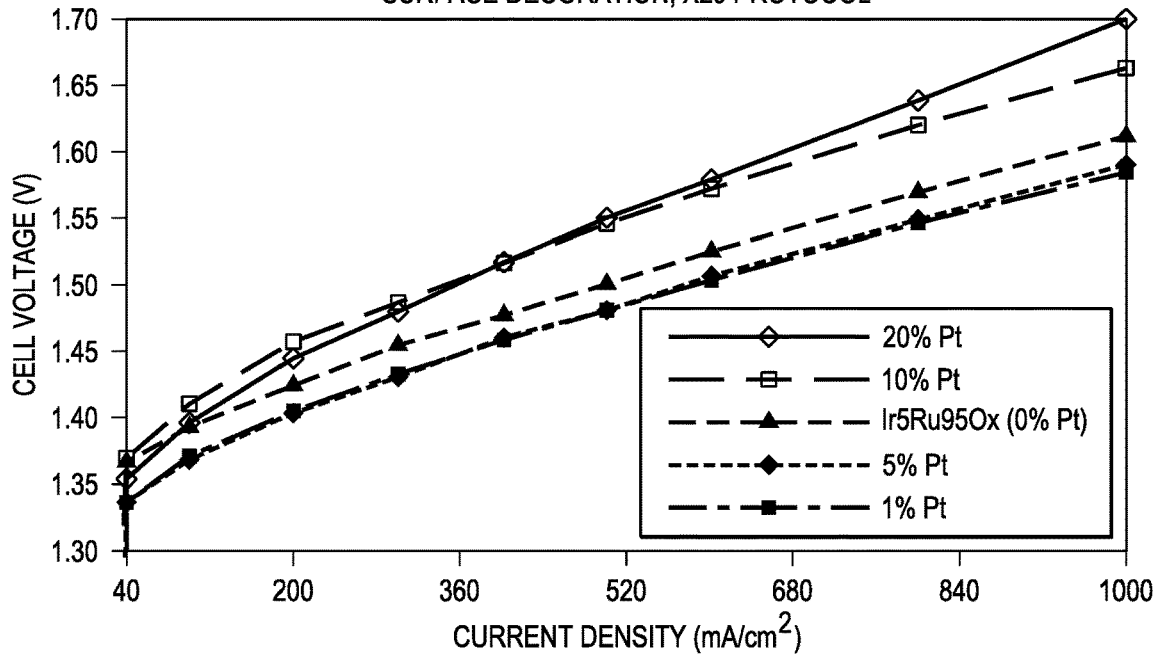
FIG. 11 shows results from a single cell for platinum loading optimization. $Ir_5Ru_{95}Ox$ catalyst with 1 wt % Pt surface modification demonstrated the best performance with five-mil thick Nafion membrane at a 75° C. cell temperature in the anode-fed mode. No backpressure.

Platinum loading optimization single cell results are given in FIGS. 10 and 11. $Ir_5Ru_{95}O_x$ catalyst with 1 wt % Pt nanoparticle surface modification demonstrated the best performance.

Figure 12:
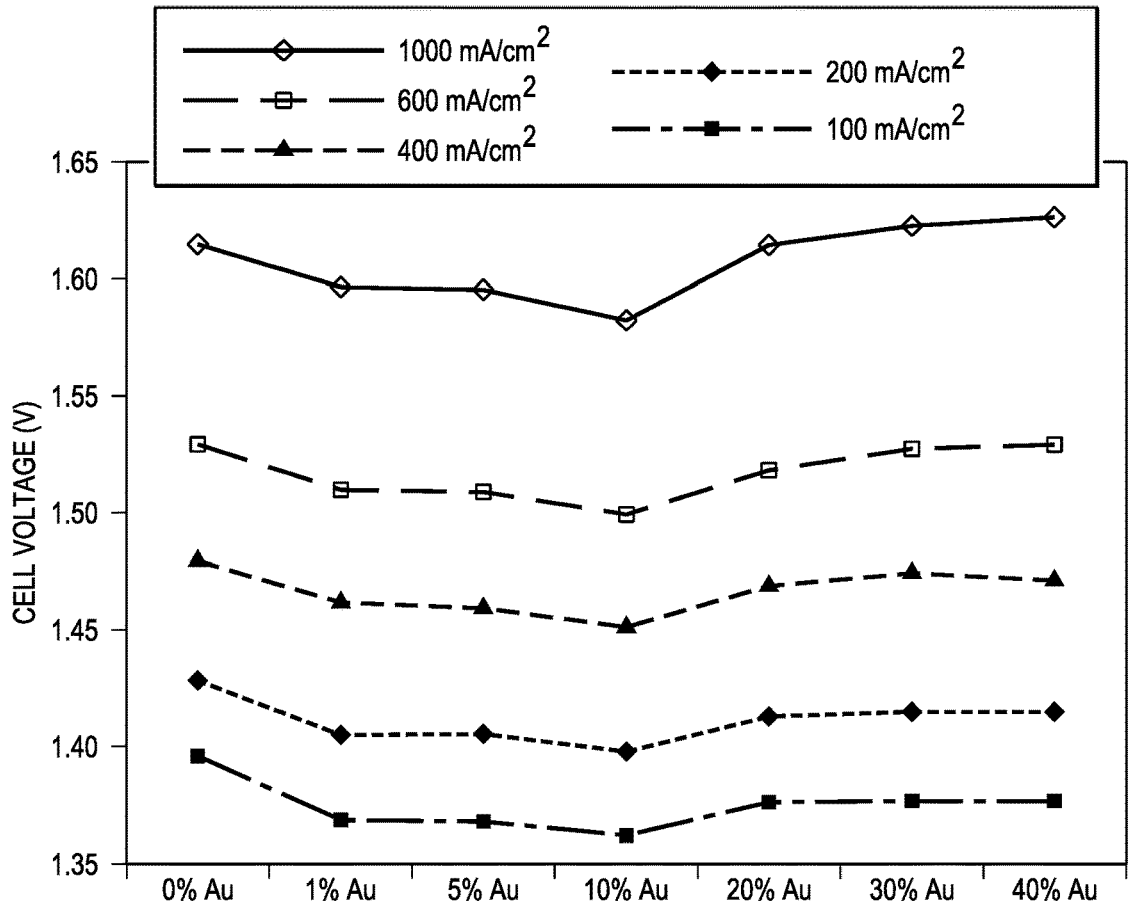
FIG. 12 shows the cell potential as a function of the Au loading on $Ir_5Ru_{95}O_x$ catalyst at specific current densities (for Au loading optimization). The Au loading range was from 0 wt % to 40 wt %. Au nanoparticles were decorated on the surface of the $Ir_5Ru_{95}O_x$. $Ir_5Ru_{95}O_x$ catalysts were synthesized with the X20 protocol at 450° C. The $Ir_5Ru_{95}Ox$ catalyst with 10 wt % Au surface modification demonstrated the best performance with five-mil thick Nafion membrane. The 10 wt % Au nanoparticle surface modification provided a cell voltage of 1.398 V at 200 mA/cm$^2$ (87.98% efficiency) at a 75° C. cell temperature in the anode-fed mode. No backpressure.
Figure 13:
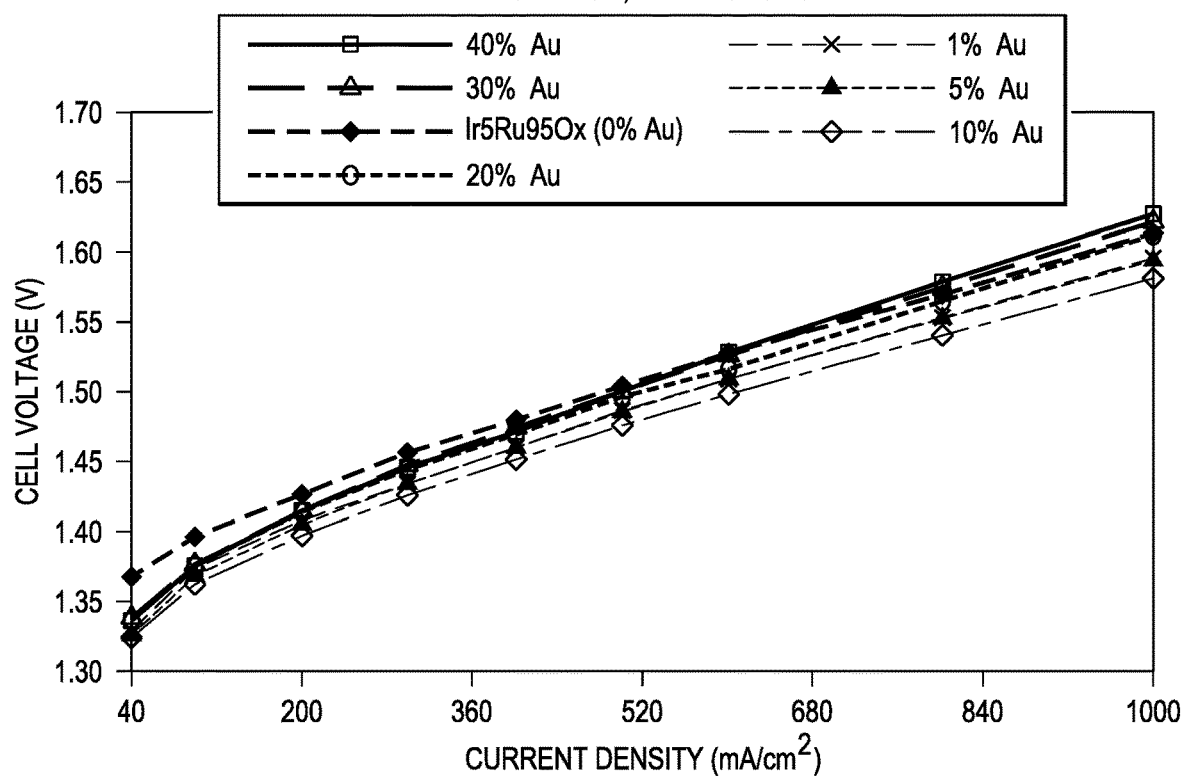
FIG. 13 shows results from a single cell for gold loading optimization. The $Ir_5Ru_{95}Ox$ catalyst with 10 wt % Au surface modification demonstrated the best performance with five-mil thick Nafion membrane at a 75° C. cell temperature in the anode-fed mode. No backpressure.

Gold loading optimization single cell results are given in FIGS. 12 and 13. $Ir_5Ru_{95}O_x$ catalyst with 10 wt % Au nanoparticle surface modification demonstrated the best performance.

In one non-limiting example, platinum loading is 0 to 20 wt %, preferably 1 to 10 wt %, or preferably 1 to 5 wt %. The skilled artisan will understand that this patent is not limited to these values, though to get the best electrocatalytic activity and corrosion resilience, 1 to 5 wt % of platinum decoration was found to be optimal.

One preferred gold loading is 0 to 40 wt %, more preferably 1 to 30 wt %, even more preferably 1 to 10 wt %. Again, the skilled artisan will recognize that the amount may be varied to optimize performance, as such, this patent is not limited to these values, though to get the best electrocatalytic activity and corrosion resilience, 1 to 10 wt % of gold decoration was found to be optimal.

One preferred combined platinum-gold loading is 1% Pt with 10% Au in order to achieve the highest efficiency for hypoxia device. Again, the skilled artisan will recognize that the amount may be varied to optimize performance, as such, this patent is not limited to these values, though to get the best electrocatalytic activity, highest efficiency, and corrosion resilience, 1% Pt with 10% Au were found to be optimal.

Figure 14:
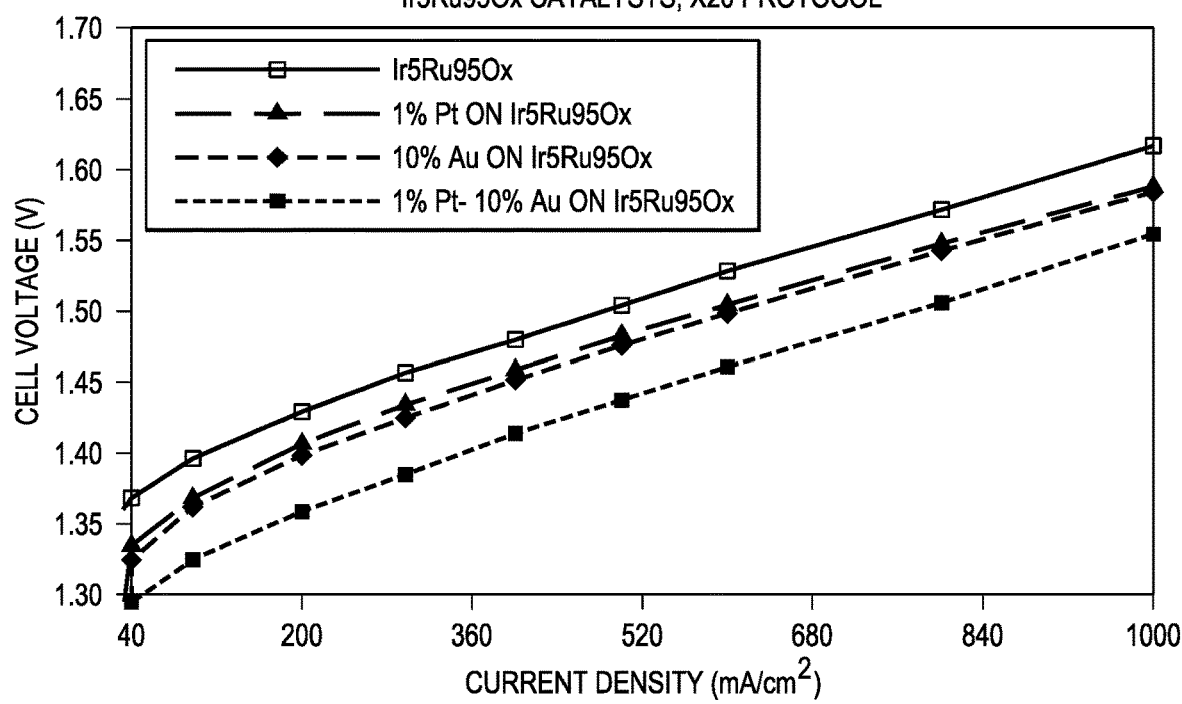
FIG. 14 shows results from a single cell for verification of combined optimal platinum-gold loading optimization. $Ir_5Ru_{95}Ox$ catalyst with 1 wt % Pt-10 wt % Au surface modification demonstrated the best performance with five-mil thick Nafion membrane. The 1 wt % Pt-10 wt % Au surface modified catalyst demonstrated a cell voltage of 1.358 V at 200 mA/cm$^2$ (90.5% efficiency) at a 75° C. cell temperature in the anode-fed mode. No backpressure.

For the combined optimal platinum-gold loading performance verification, 1 wt % Pt-10 wt % Au nanoparticles were decorated on the $Ir_5Ru_{95}O_x$ catalyst surface. The $Ir_5Ru_{95}O_x$ catalyst was synthesized at 450° C. using the X20 protocol. Single cell results for the verification of the combined optimal platinum and gold loading with $Ir_5Ru_{95}O_x$ catalyst was given in FIG. 14. A cell voltage of 1.358 V at 200 mA/cm$^2$ was obtained with 1 wt % Pt-10 wt % Au nanoparticles surface modified $Ir_5Ru_{95}O_x$ (with a five-mil thick Nafion membrane) and this corresponds to 90.5% MEA efficiency.

Interestingly, the optimal Pt and Au decorations procedure produce similar improvements in performance over the basic oxide. When combined, they produce an improvement about equal to the sum of the two individual contributions. It was expected the combination of Pt and Au to be better than the individual elements, but the magnitude is surprisingly very high.

Figure 15:
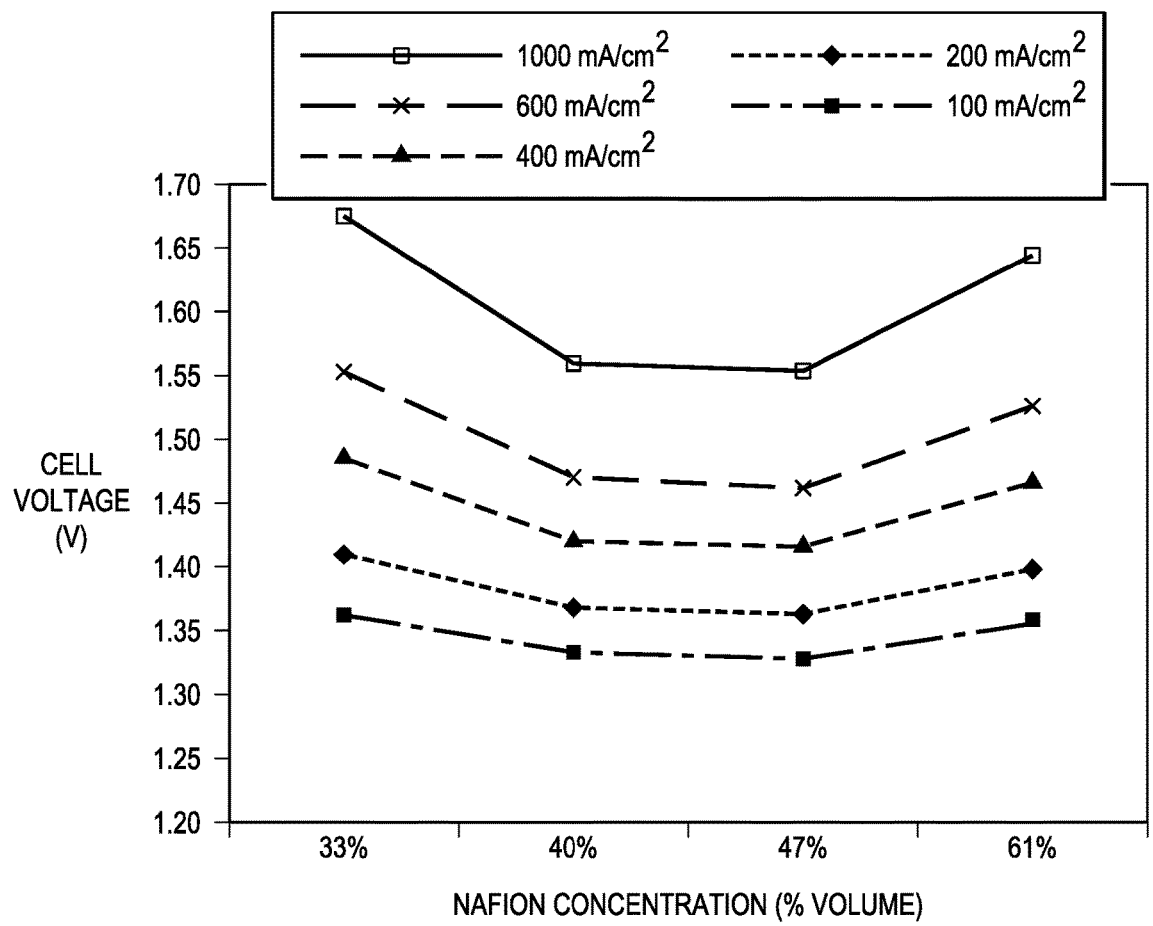
FIG. 15 shows cell potential as a function of the Nafion ionomer concentration in the anode catalyst layer. Optimized anode catalyst with 47 vol % Nafion ionomer in the catalyst layer demonstrated the best performance with five-mil thick Nafion membrane at a 75° C. cell temperature in the anode-fed mode. No backpressure.

Effect of Nafion loading in the anode catalyst layer. The content of Nafion material in the anode electrocatalyst determines the ionic conductivity and electrical conductivity. It is critical to have good ionic conductivity and satisfactory electrical conductivity. The optimal Nafion ionomer concentration for the optimized anode catalyst was investigated in the range of 33 vol % to 61 vol %. Single cell results are provided in FIG. 15. The anode catalyst layer with 47 vol % demonstrated the best performance. This confirms the Nafion content we have been using.

The preferred Nafion volume percent in the hypoxia anode is 33 to 61%, more preferably 40 to 55 volume %, even more preferably 45 to 50 volume %. Again, the skilled artisan will recognize that the amount may be varied to optimize performance, as such, this patent is not limited to these values, though to get the best ionic conductivity and electrochemical performance, a range of 45 to 50 volume % of Nafion is needed at the hypoxia anode side.

Atmospheric air is composed of ~21% oxygen. Additionally, it has been shown that this percentage is closely maintained even up to 30,000 ft altitude. However, the atmospheric pressure changes significantly with altitude. This change in total pressure directly corresponds to the partial pressure of oxygen and is the reason humans struggle breathing at elevated altitudes (FIG. 16).

Figure 16:
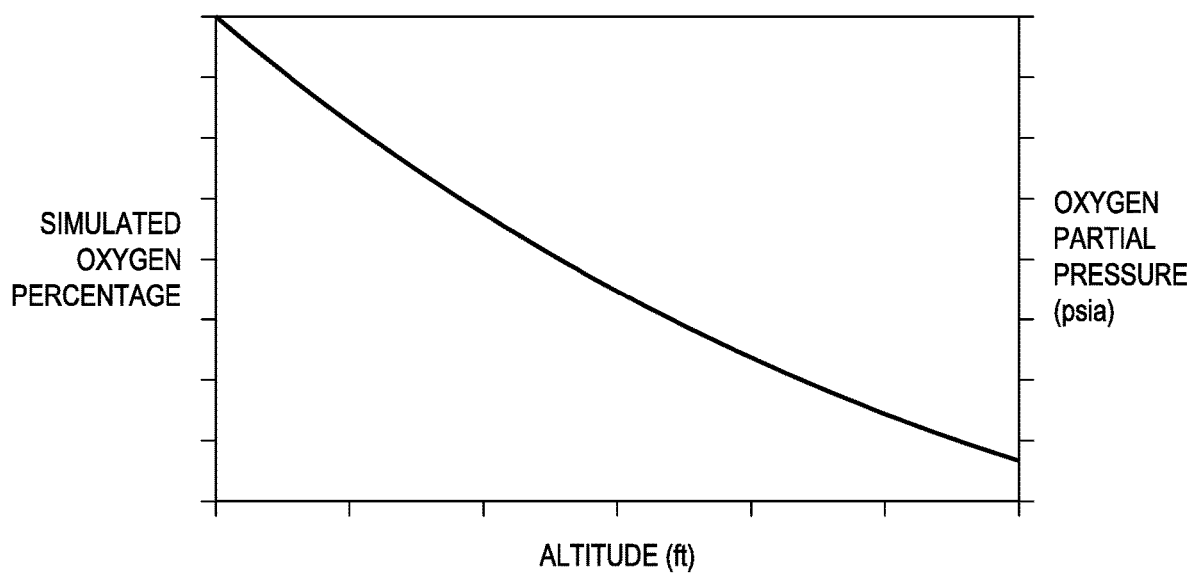
FIG. 16 shows simulated oxygen percentage and oxygen partial pressure as a function of altitude.

Therefore, in order to simulate an elevated altitude under normobaric conditions, the partial pressure of oxygen (simulated oxygen percentage) must be reduced to match the values shown in FIG. 16. The present invention was used in the hypoxia simulation device as a curve fit to FIG. 16, which was used to determine the required oxygen partial pressure for a given target altitude based on the following equations:

$$y=-4.364E-14x^3+7.452E-09x^2-5.281E-04x+1.469E+01$$

$y$=simulated atmospheric pressure (psia), $x$=altitude (feet)

Removing oxygen from an air stream was accomplished utilizing an electrochemical oxygen separation device and technique of the present invention. This technology directly and selectively removes oxygen from the air. Due to the reliability of the electrochemical reactions, the amount (mass) of oxygen removed is directly proportional to the electrical current passed through the electrochemical cells. This correlation results in approximately 3.5 std ml/min of oxygen removal per amp of current. The derived electrochemical reactions, combined with the previously discuss altitude/pressure relations are used, along with the measured inlet air flow rate, are used to determine the required electrical current to achieve a given simulated altitude. These relations are presented below in expanded form for clarity.

Inlet Oxygen rate (slpm)=Total inlet rate (slpm)*20.945% O2

Oxygen Partial Pressure (psia)=Simulated Atmospheric Pressure (psia)*20.945% O2

Simulated oxygen percentage=Oxygen Partial Pressure (psia)/14.668 (psia)

Nitrogen rate (slpm)=Total inlet rate (slpm)*(100%−20.945% O2)

Total outlet rate (slpm)=Nitrogen rate (slpm)/(100%−simulated oxygen percentage)

Outlet Oxygen Rate (slpm)=Total outlet rate (slpm)*simulated oxygen percentage

Oxygen removal (slpm)=Inlet Oxygen rate (slpm)−Outlet Oxygen Rate (slpm)

Total Current (amps)=Oxygen removal (slpm)/0.0035 (A/slpm)

Stack Current (amps)=Total Current (amps)/# of cells in series

The controls work by first measuring the Total inlet air rate (slpm) via the sum of FM-101 & 103. The air flow set point is controlled by the pressure on demand algorithm described hereinabove. The measured flow is multiplied by the assumed oxygen concentration of air to determine the actual amount of oxygen entering the electrochemical stacks. As a first order approximation, 20.945% is used. Although this is a good average for most conditions, several factors can influence the actual percent oxygen in the ambient air. Most notably a combination of relative humidity, temperature and atmospheric pressure can significantly affect the inlet oxygen percentage.

The present invention increases the accuracy of the simulated altitude in part by measuring and accounting for the relative humidity, temperature and atmospheric pressure to calculate the actual oxygen percentage of the air. As a secondary measure, an oxygen sensor is also used to verify the actual ambient oxygen partial pressure. This redundant measure enables the device to self-verify the oxygen concentration and notify the user if the accuracy of the delivered simulated altitude air is in question. As a tertiary measure, an oxygen sensor is also used to measure the oxygen concentration of the outlet stream.

As mentioned previously, the target outlet oxygen partial pressure is determined via the altitude set point. This measure is used to determine the required amount of oxygen needed in the outlet stream to achieve the target-simulated altitude. From here the required amount of oxygen that needs to be removed is used to determine the electrical current required. These relations are calculated real time via the onboard microprocessor to actively control the delivered simulated altitude flow accurately.

Hypoxia training involves exposing personnel to profiles of oxygen concentrations that vary as a function of time. The oxygen concentration is varied as a function of time to simulate changes in altitude above sea level. Various profiles may be created to represent changes of altitude at various rates as well as various altitude extremes and hold times at intermediate altitudes. In order to allow for the electrochemical system to remove oxygen from the air, a significant amount of electrical power is needed. The electrical power required is a function of the altitude that is being simulated and the required flow rate. As the simulated altitude increases, additional electrical power is needed to remove the required amount of oxygen from the ambient air. At high simulated altitudes the required electrical power exceeds that available from common 120 Volt AC (Alternating Current), 15 amp or 20 amp power outlets. In order to allow for a hypoxia training device to operate with altitude profiles that include high altitudes (30,000 ft and beyond) and high flow rates (50 slpm and beyond) without exceeding the available AC power, a hybrid power management and energy storage system is required. The system stores energy during the lower power portions of the altitude profiles and makes use of the stored energy to supplement the power available for the AC power input during the higher power portions of the altitude profiles.

Figure 17:
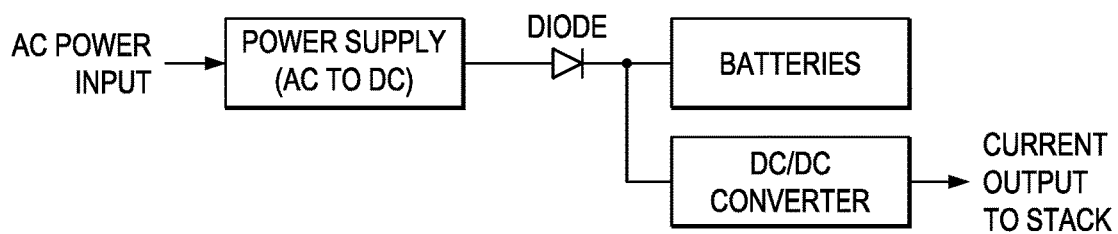
FIG. 17 shows the hybrid power management and energy storage system.

FIG. 17 shows a hybrid power management and energy storage system for use with the present invention. The system operates as follows. A power supply is used to convert the AC input power to DC (Direct Current) power. This power supply incorporates both voltage and current limiting. The voltage limiting is used to limit the voltage to which the battery (or batteries) used for energy storage is (are) charged. The current limiting is used to assure that that power drawn for the AC power input does not exceed that available from the AC power circuit (typically 15 to 20 amps). The diode connected to the output of the power supply is used to protect the power supply from reverse voltage in the event of the power to the supply being turned off or disconnected. The DC/DC converter is used to convert the power supplied form the power supply and the battery (or batteries) into the voltage required to drive the electrochemical stack with the current required to remove the amount of oxygen required to simulate the altitude. The output voltage of the DC/DC converter is adjusted by a control system as required for the output current from the DC/DC converter to follow that required by the simulated altitude profile. The DC/DC converter may be a buck converter, a boost converter or a buck/boost converter depending upon the required stack voltage relative to the battery voltage. If the stack voltage is always higher than the battery voltage, a boost converter is required. If the stack voltage is always lower than the battery voltage, a buck converter is required. If the stack voltage may be higher or lower than the battery voltage, a buck/boost converter is required.

The batteries are charged during periods of the simulated altitude profile that require less power than is available from the AC power input and discharged during periods of the simulated altitude profile that require more power than is available from the AC power input. Current flows into the battery if it is not fully charged and excess power is available. Current flows out of the battery when more power is required to simulate the required altitude than is available from the AC power input. If the required altitude profile to be simulated requires more energy to be provided to the battery than is available during the profile, a battery recharge time is required to allow for adequate energy to be provided the battery prior to running a new profile.

Description of pure oxygen capability. A key advantage of the electrochemical oxygen separation of the present invention is the production of a high purity oxygen stream. As the air stream on the cathode is depleted of oxygen, the anode stream becomes oxygen enriched. In fact, the net effect of the electrochemical reactions is that for every oxygen molecule removed from the cathode, one oxygen molecule is produced at the anode. In this way, only oxygen and water are produced on the anode. After the water is removed through phase separation, only saturated oxygen remains.

The present invention maximizes the usefulness of this secondary oxygen production by temporarily storing it in a storage container at atmospheric pressure. This temporary storage enables the device to deliver up to 5 minutes of pure oxygen to the pilot for rapid recovery from the hypoxic conditions.

During hypoxia simulation, if the pilots SpO$_2$ falls below a given threshold, or if the test administrator observes that the pilot has achieved the hypoxic conditions, the simulation is aborted. SV-101 is closed, and PDP-105 is enable, which quickly delivers pure oxygen to the pilot. This allows the pilot to recover quickly, avoiding any long terms effects for the temporally induced hypoxia.

If the storage container is not connected to the device (optional), or once the oxygen bag is depleted, the pilot will be delivered ~40% oxygen directly from the electrochemical stack anode. As an alternative, regular air may also be delivered to the pilot if desired. Based on the stack control algorithms, any user selectable oxygen percentage may also be delivered to the pilot by diluting the delivered oxygen with additional air.

Implementation of water recovery features to reduce logistics. An important concern in operating the O$_2$ Trainer was maintaining water balance. Air pumped into the electrochemical stacks carry water vapor into the system based on atmospheric conditions. As the air moves through the electrochemical stacks, it leaves at almost 100% relative humidity. Water for air humidification becomes available due to the formation of water from the reaction of hydrogen (from the anode) and oxygen (in the cathode), electro-osmotic drag (due to movement of hydrogen protons to the cathode) and diffusion of water from anode to cathode. In an ideal situation, there would be no electro-osmotic drag or diffusion, hence, maintaining perfect water balance in the coolant loop. Since such a situation isn't realistic, condensers and phase separators must be used to recover water lost from the coolant loop (or anode side).

An appropriately sized condenser is required to cool down the humidified air and, therefore, condense the water vapor. This condensed water vapor can then be recovered into the coolant loop. There are, however, limitations to how much water can be condensed. In condensers, the medium undergoing a phase change, such as boiling or condensation, has an infinite capacitance rate (Capacitance Rate Equation). This is because mediums undergoing phase change do not undergo a change in temperature and, therefore, have an infinite specific heat capacity. In such conditions, heat transfer is limited by the fluid with the much lower capacitance rate that experiences a larger change in temperature than the condensing medium. As the non-condensing fluid (in this case ambient air pushed by a fan) approaches the temperature of the condensing medium (reduced-oxygen air & pure oxygen gas stream) heat transfer rate drops substantially. Hence, it's never possible for the exiting condensing fluid to reach ambient temperature unless an infinitely large heat exchanger or a very large cold fluid flow rate is employed.

$$\dot{C} = \dot{m} \cdot c_p$$

$\dot{m}$=Mass flow rate; $c_p$=Specific heat capacity. Capacitance rate Equation.

Phase separators are also necessary to separate the condensed water from the air. This also prevents liquid water from entering fluid loops that deliver gas to the end user and damage to electronics downstream.

Temperature and pressure are two important factors that affect the amount of water vapor in the air. Increasing temperature at constant pressure increases the amount of water vapor dry air can carry. This, however, decreases the relative humidity of the air. Relative humidity is an indicator of the percentage of the maximum humidity the air is carrying. At 100% relative humidity, air is carrying the maximum amount of water vapor and a slight drop in temperature will cause the water vapor to condense to liquid water. Increasing the pressure of air-water vapor mixture increases the partial pressure of dry air and water vapor. This causes the relative humidity to increase and making water vapor condensation easier. Equation 2 shows relative humidity as a function of pressure and Dalton's law applied to system pressure. The pressure of the reduced-oxygen air to the mask is reduced from ~30 psia to ~15 psia to prevent condensation of water vapor in the mask. By reducing the pressure of saturated air-water vapor mixture by half, Equation 2, shows that the partial pressures are reduced by half also. Therefore, at constant temperature, the relative humidity drops to 50%. This also prevents dryness in the end users air passages.

Equation 2: Relative humidity($\phi$) (left), Partial pressures of air-water vapor mixture (right).

$$\phi = \frac{P_{vapor}}{P_{saturation\,at\,mixture\,temperature}}; \quad P_{System} = P_{vapor} + P_{dry\,air}$$

Figure 18:
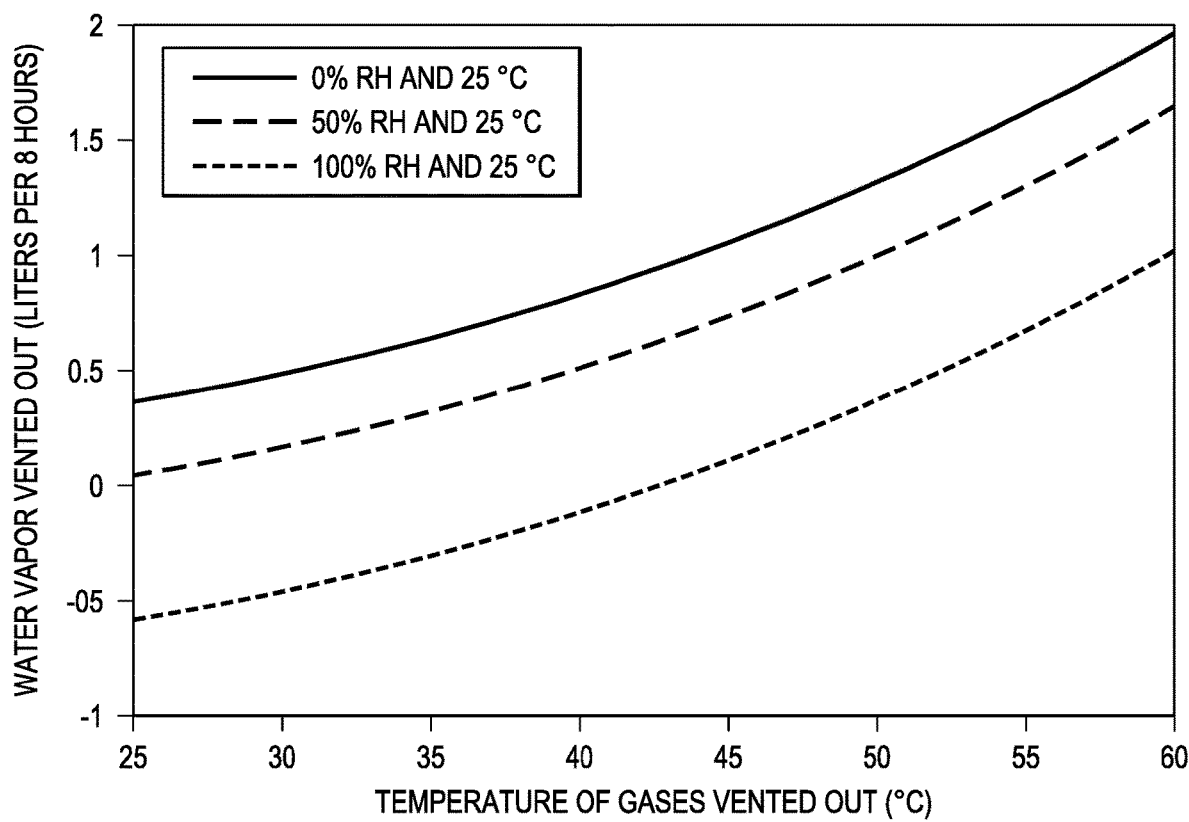
FIG. 18 shows water vapor vented out of the system vs. temperature of vented gases for an incoming air relative humidity of 0, 50 and 100% RH. Water consumption rates without the water recovery condensers are shown at the right (60° C.). Water consumption rates with the water recovery condensers are shown at the left (30° C.).

FIG. 18 shows the sum total of water vapor vented out of the system through the mask supplying reduced oxygen air and the pure oxygen vent. As mentioned above, temperature is one of the major functions that govern water vapor content in dry air; this has been theoretically shown in FIG. 18. FIG. 18 shows the water vapor vented out of the system vs. temperature of vented gases for an incoming air relative humidity of 0, 50 and 100% RH. Water consumption rates without the water recovery condensers are shown at the right (60° C.). Water consumption rates with the water recovery condensers are shown at the left (30° C.).

Also, as the relative humidity of air coming into the system increases the amount of water lost decreases. The highest quantity of water is lost when completely dry air is supplied to the system. On the other hand, by supplying air that is saturated ($\phi$=100%), water is added to the coolant reservoir (depending on outlet temperature & pressure) because the amount of water vapor condensed by the condensers is higher than what is lost in the vented gases.

As the temperature of vented gases increase the amount of water lost increases. For instance, if the gases were vented at 60° C. 2 L to 1 L of water per 8 hours of operation would be lost versus ½ L to 0 L of water. If the incoming air is completely saturated the system would actually gain 0.5 L of water.

Use of an ion exchange resin enables the use of tap water by providing an ion exchange resin for water that comes in contact with the anode. Optionally, an ion exchange resin can also be provided after the anode or the cathode for recycling that water.

The electrochemical oxygen separation device utilizes a Proton Exchange Membrane (PEM), which is selectively conductive to cations. For the purpose of hypoxia simulation, hydrogen protons are transferred through the membrane. However, other charged ions and free radical can also be absorbed into the membrane, reducing the conductivity and thus performance. Many of such ions are present in common tap water. As such, tap water is potentially damaging to the electrochemical stack and must not be used for humidification.

Typically, the present invention uses >10 MOhm*cm De-Ionized (DI) water as a water supply for humidification to replace what water is lost from the system. However, in practical applications, this quality of DI water is not commonly available. Therefore, the present invention incorporates a mixed bed ion exchange resign into the water fill port of the system. This approach allows the user to refill the system with normal tap water without damaging the system.

The present invention also utilizes a DI polishing bed within the system of which the anode water is constantly re-circulated through during operation. This approach added a secondary layer of protection by capturing any contaminating ions, which made it through the initial DI bed during filling. The polishing bed also captures any ions leached out from other metallic components within the anode recirculation loop, thus dramatically extending lifetime.

Other Applications of OER Advanced Catalyst. The first embodiment as it was discussed is the use of the advanced OER electrocatalyst in the electrochemical hypoxia device. In terms of configuration, this device employs liquid water at the anode and air at the cathode. Liquid water is electrochemically dissociated to oxygen, protons, and electrons. While oxygen is stored for emergency or vented out, protons and electrons are transferred to cathode side and reacted with oxygen molecules in the air feed. This later reaction generates oxygen-reduced air stream that is used for hypoxia training of pilots.

The advanced OER electrocatalyst can also be used for one or more of the following applications.

Example 1

Low, medium, and/or high-pressure pure oxygen generators and oxygen compressors (based on electrochemical generation of pure oxygen) can also benefit from the advanced OER electrocatalyst. In terms of configuration, these devices employ liquid water at the anode and utilize the electrolysis reaction in order to produce pure oxygen at different compression pressures. In general such devices are well-known for the oxygen generation and storage at 0 to 400 psi, 400 to 2200 psi, and 2200 to 3600 psi. In terms of electrochemical reactions, at anode liquid water is electrochemically dissociated to oxygen, protons, and electrons. While oxygen is generated and compressed to the desired pressure for the intended applications, protons and electrons are transferred to cathode side, hydrogen gas is produced and usually vented out at atmospheric pressure. Since oxygen compressor devices do not use depolarization mechanism at the cathode, the operating cell voltage for such devices are much higher compared to hypoxia device cells. While it is possible to use cathode depolarization in order to reduce the overall cell voltage, it is not recommended due to the following issues: compressed oxygen gas diffusion to the cathode can create safety issues (creating chemical combustion reaction with hydrogen gas) or contamination of oxygen gas with nitrogen gas.

Example 2

Low, medium, and/or high pressure oxygen concentrators (based on electrochemical generation of oxygen enriched air) can also benefit from the advanced OER electrocatalyst. Such systems are useful for generating 22% to 95% (by volume or weight) oxygen enriched air for numerous industrial and medical applications. In terms of configuration, these devices employ liquid water at the anode and utilize the electrolysis reaction in order to produce pure oxygen at different compression pressures (0 to 3600 psi range). In terms of electrochemical reactions, at the anode liquid water is electrochemically dissociated to oxygen, protons, and electrons. Protons and electrons are transferred to the cathode side and reacted with oxygen in the air feed and a nitrogen enriched air stream is generated. Depending on the desired oxygen enrichment, pure oxygen generated at the anode is mixed with the appropriate ratio of nitrogen enriched stream in a gas mixing chamber and utilized. Since oxygen concentrator devices use depolarization mechanism at the cathode (electrochemical reaction of protons and electrons with oxygen molecules in the air without forming chemical combustion reactions), the operating cell voltage for such devices are comparable to electrochemical hypoxia device cells.

Example 3

Electrochemical inerting systems (that are based on electrochemical generation of nitrogen enriched air) can also benefit from the advanced OER electrocatalyst. Such systems are useful for generating 0% to 95% (by volume or weight) nitrogen enriched air for numerous industrial inerting applications (such as inerting of the fuel tanks for military fuel tankers, inerting of ship and airplane fuel tanks for commercial and military planes, inerting residential fuel tanks, and other inerting applications that require decreased probability of combustion of any flammable materials stored in a confined space). In terms of configuration, an electrochemical inerting device will employ liquid water at the anode and utilize the electrolysis reaction in order to produce pure oxygen (usually at ambient pressure). In terms of electrochemical reactions, at the anode liquid water is electrochemically dissociated to oxygen, protons, and electrons. Protons and electrons are transferred to the cathode side and reacted with oxygen in the air feed and a nitrogen enriched air stream is generated. Depending on the desired nitrogen enrichment, multiple electrochemical inerting systems can be used to achieve much greater nitrogen enrichment levels such as >95%. While oxygen generated at the anode is usually vented out, the nitrogen enriched stream generated at the cathode is used for inerting applications. Since electrochemical inerting devices use depolarization mechanism at the cathode (electrochemical reaction of protons and electrons with oxygen molecules in the air without forming chemical combustion reactions), the operating cell voltage for such devices are comparable to electrochemical hypoxia device cells and lower than pure oxygen compressors.

Example 4

Low-, medium-, and/or high-pressure pure hydrogen generators and hydrogen compressors (based on electrochemical generation of pure hydrogen) can also benefit from the advanced OER electrocatalyst. In terms of configuration, these devices employ liquid water at the anode and utilize the electrolysis reaction in order to generate protons, which are then recombined at the cathode to produce pure hydrogen gas. In general such devices are well-known for the oxygen generation and storage at 0 to 400 psi, 400 to 2200 psi, and 2200 to 5000 psi or possibly greater than 5000 psi for some niche applications. In terms of electrochemical reactions, at the anode liquid water is electrochemically dissociated to protons, electrons, and oxygen. Due to the electrical gradient, protons and electrons are transferred to the cathode. At zero voltage over a hydrogen gas generation electrocatalyst, protons are recombined and hydrogen molecules are formed. Generated hydrogen gas is then compressed and stored at the desired pressure. Oxygen generated at the anode is usually vented out at ambient pressure. Since electrochemical hydrogen generator and hydrogen compressor devices do not use depolarization mechanism at the cathode, the operating cell voltage for such devices are much higher compared to hypoxia device cells.

Example 5

Low, medium, and/or high pressure proton exchange membrane electrolyzers can also benefit from the advanced OER electrocatalyst. In terms of configuration, these devices employ liquid water at the anode and utilize the electrolysis reaction in order to produce pure oxygen or hydrogen at different compression pressures. In general such devices are well-known for the oxygen generation and storage at 0 to 400 psi, 400 to 2200 psi, and 2200 to 3600 psi. Proton exchange membrane based electrolyzer devices can also be used to generate pure hydrogen gas and store it at the desired pressure (0 to 5000+ psi). In terms of electrochemical reactions, at the anode liquid water is electrochemically dissociated to oxygen, protons, and electrons. For generation of pure oxygen, no cathode depolarization approaches are used. For generation of pure hydrogen, oxygen is vented out at ambient pressures.

Example 6

Electrochemical gas and liquid sensor devices can also benefit from the advanced OER electrocatalyst. In terms of configuration, these devices generally take samples of gases from different environments and measure the concentration of target gas by oxidizing or reducing the target gas at an electrode and measuring the resulting current. The OER electrocatalyst material can detect the following gases (but this patent is not limited to these target gases): nitrous oxides, ammonia, carbon monoxide, carbon dioxide, etc. In terms of electrochemical liquid sensors, the OER electrocatalyst material of the present invention was found to detect pH changes.

Figure 19:
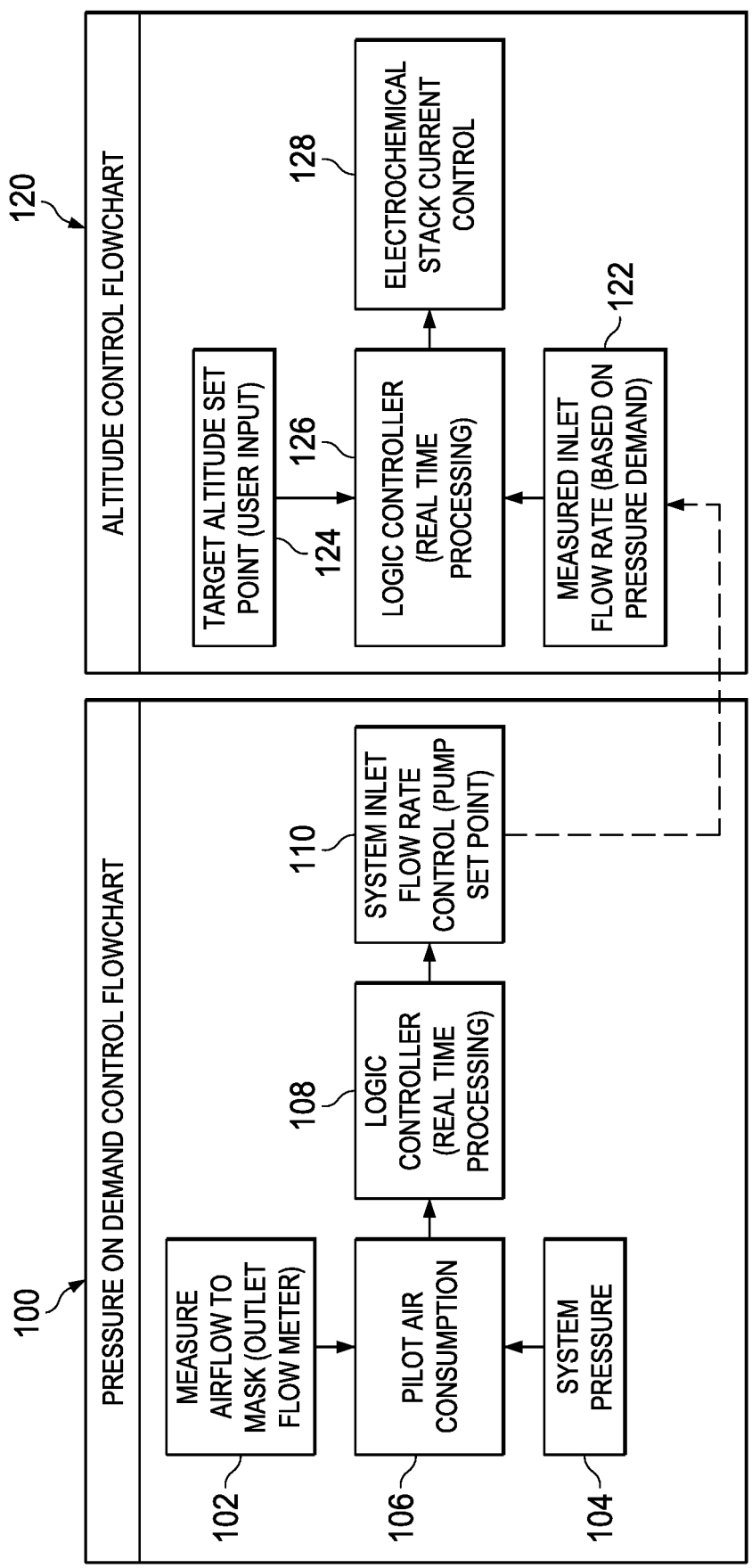
FIG. 19 shows a Pressure on Demand Control Flowchart.

FIG. 19 shows a Pressure on Demand Control Flowchart 100, in which two inputs are provided, measuring the airflow to a mask at an outlet flow meter 102 and a system pressure 104. These two inputs (102, 104) provide a pilot air consumption 106, which data is then provided to a logic controller 108 (which can process in real time), which then controls the system inlet flow rate control pump 110 (at a predetermined pump set point). The data from the system inlet flow rate control pump 110 is then input into the altitude control flowchart 120, which, in conjunction with the measured inlet inflow rate 122 (based on pressure demand) and the target altitude set point 124 (user input), is provided to the logic controller 126 (which can process in real time) and then provides an input into the electrochemical stack current control 128, which varies the current at the stack, which correlates directly to the amount of oxygen generated at the anode, and the amount of oxygen combined with hydrogen to form water at the cathode, thereby varying the final amount of oxygen available at the oxygen air mask.

In FIG. 19, the outlet flow meter 102 is for example FM-102. System pressure 104 can be determined from PT-101 and/or PT or equivalent pressure transducers located between the EOS system and the accumulator ACUM-101. By way of example, control pump 110 can be represented by PDP-101 and/or PDP-102. Measured inlet flow rate 122 can be determined from FM-101 and/or FM-103.

Figure 20A:
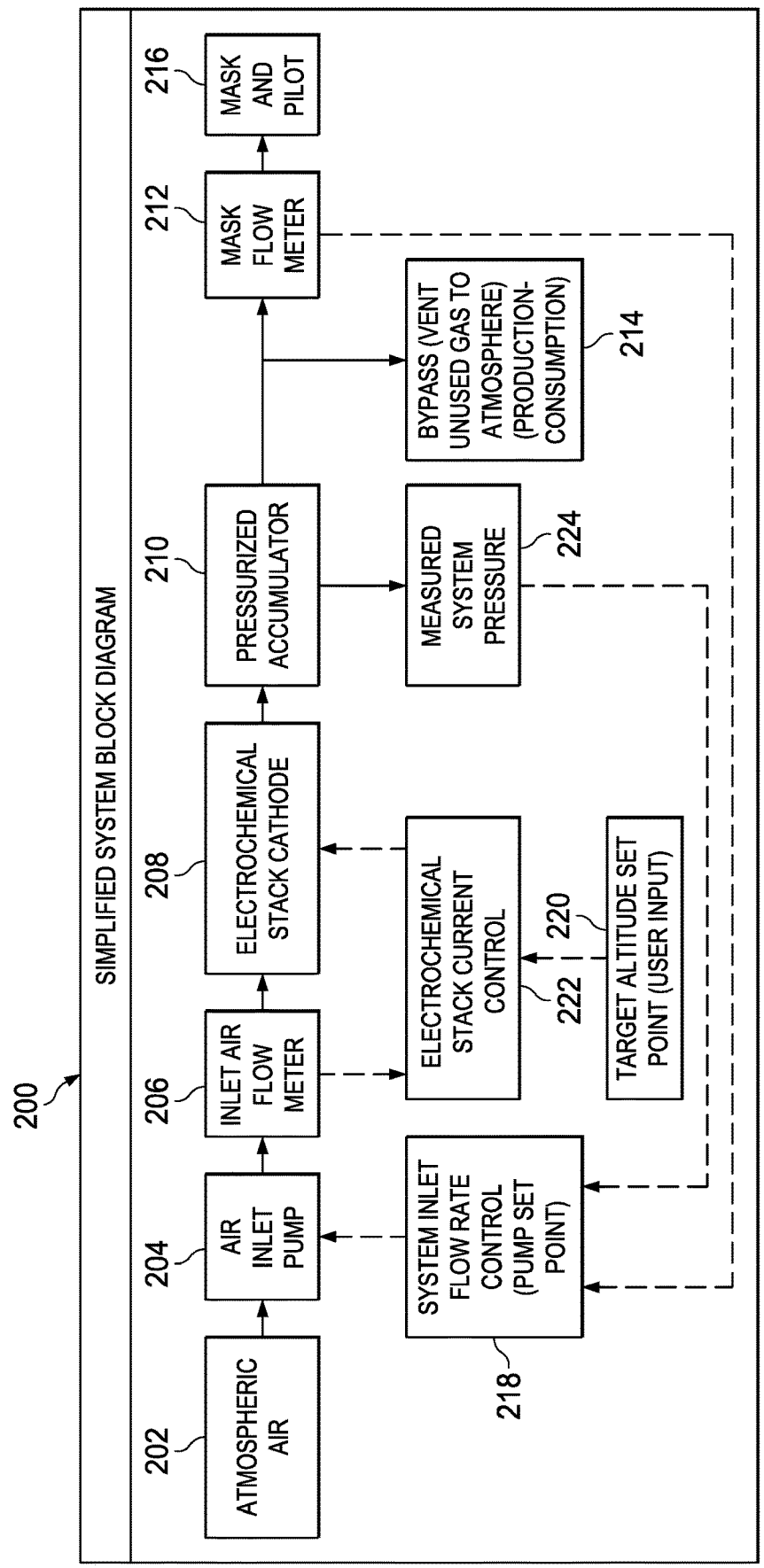
FIGS. 20A to 20B show a simplified system block diagram flowchart.
Figure 20B:
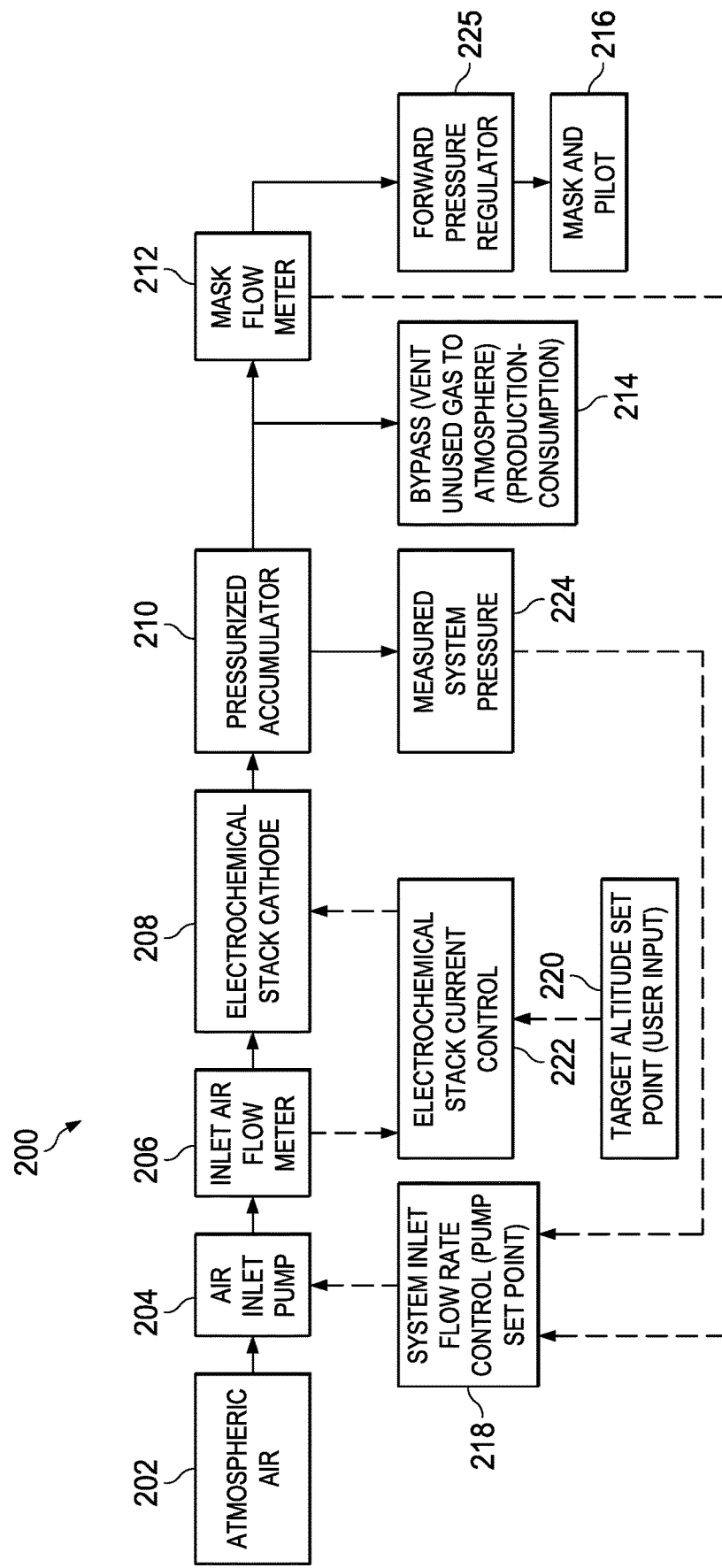

FIG. 20A shows a simplified system block diagram flowchart 200. Atmospheric air 202 enters air inlet pump 204 and the air that exits the air inlet pump 204 is detected at input air flow meter 206. The atmospheric air then contacts one or more electrochemical stacks 2-8 at the cathode, which then enters a pressurized accumulator 210. The air from the pressurized accumulator 210 can be diverted by a valve to a mask flow meter 212, or a bypass 214, which vents unused gas to the atmosphere or production-consumption. The air that traverses the mask flow meter 212 reaches the mask and a pilot at 216. Several inputs are used to modify the flow through the system. First, the mask flow meter 212 is connected to and provides data to the system inlet flow rate control 218 (which controls the pump set-point) and which modifies the output of air inlet pump 204. Second, a user-defined target altitude set point 220 (an altitude setting) is provided to the electrochemical stack current control 222, which in conjunction with information about the amount of air flow at air flow meter 206, controls the amount of current that reaches the electrochemical stack 208, which then controls the amount of oxygen in the atmospheric air that is pulled from the atmospheric air at the electrochemical stack 208. The system inlet flow rate control 218 also received input from the measured system pressure 224, which is measuring the amount of pressure in the pressurized accumulator. In FIG. 20B, a forward pressure regulator 225, is configured to respond to pressure differentials in the conduit connecting the accumulator 210 and the mask.

In FIG. 20A, the air inlet pump 204 can be PDP-101 and/or PDP-102. Input air flow meter 206 is equivalent in function and placement to FM-101 and/or FM-103. Accumulator 210 is equivalent to ACUM-101 and ACUM-102. Mask flow meter 212 is equivalent to FM-102. Bypass 214 is equivalent to BPR-101. Electrochemical stack 208 is equivalent to EOS-101 and EOS-102. System pressure 224 is equivalent to PT-101 and/or PT-103 or equivalent pressure transducers located between the EOS system and the accumulator ACUM-101. In FIG. 20B, the forward pressure regulator 225 is equivalent to FPR-101.

Figure 21A:
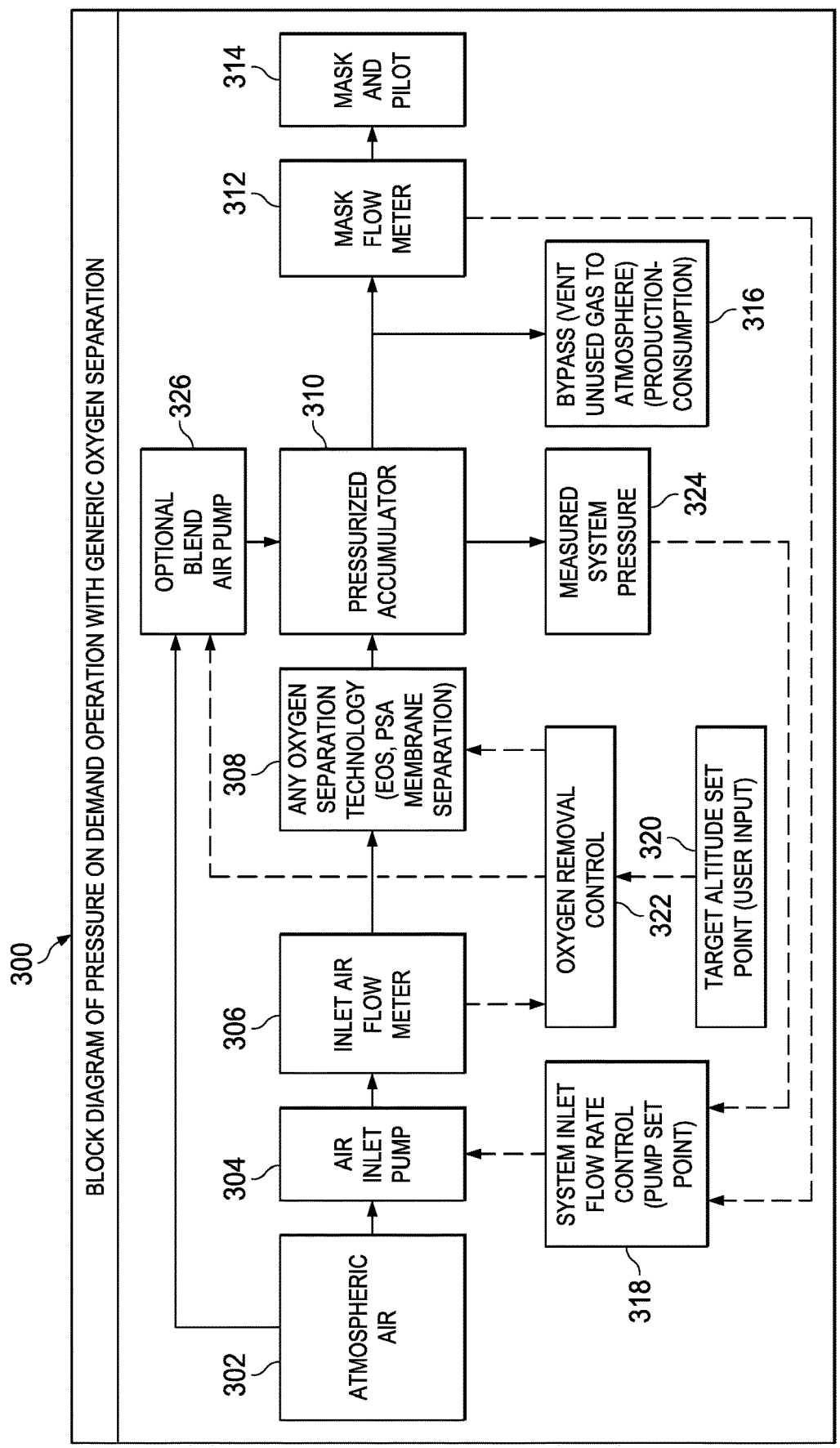
FIGS. 21A to 21B shows a block diagram of pressure-on-demand operation with a generic oxygen separation flowchart.
Figure 22A:
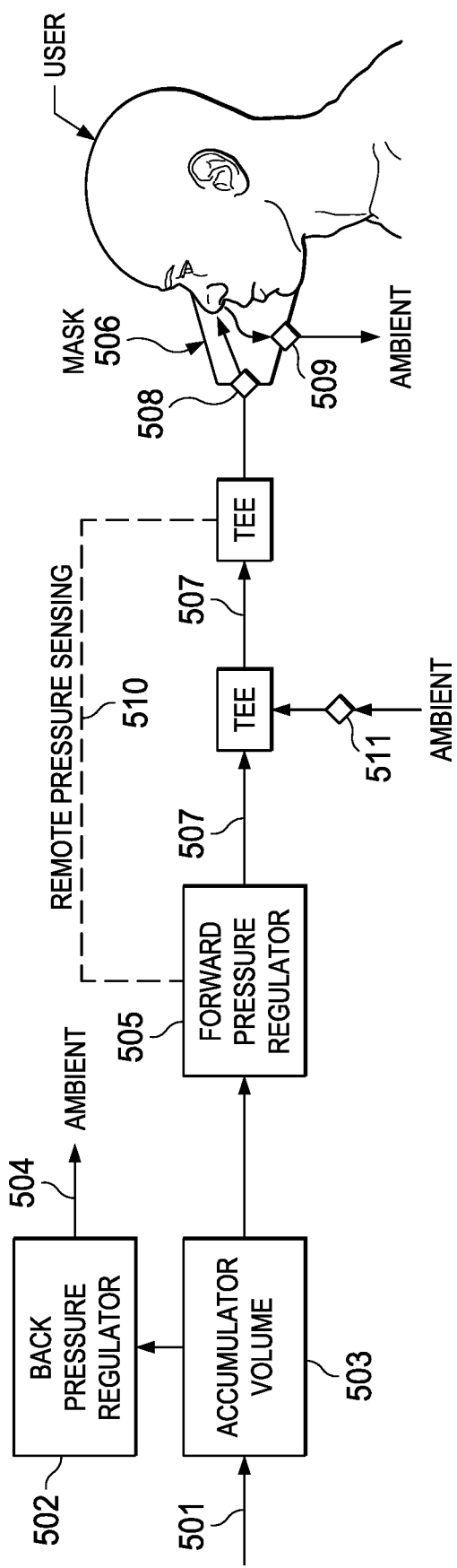
FIGS. 22A to 22B show a diagram of pressure-on-demand operation with a generic oxygen separation.
Figure 22B:
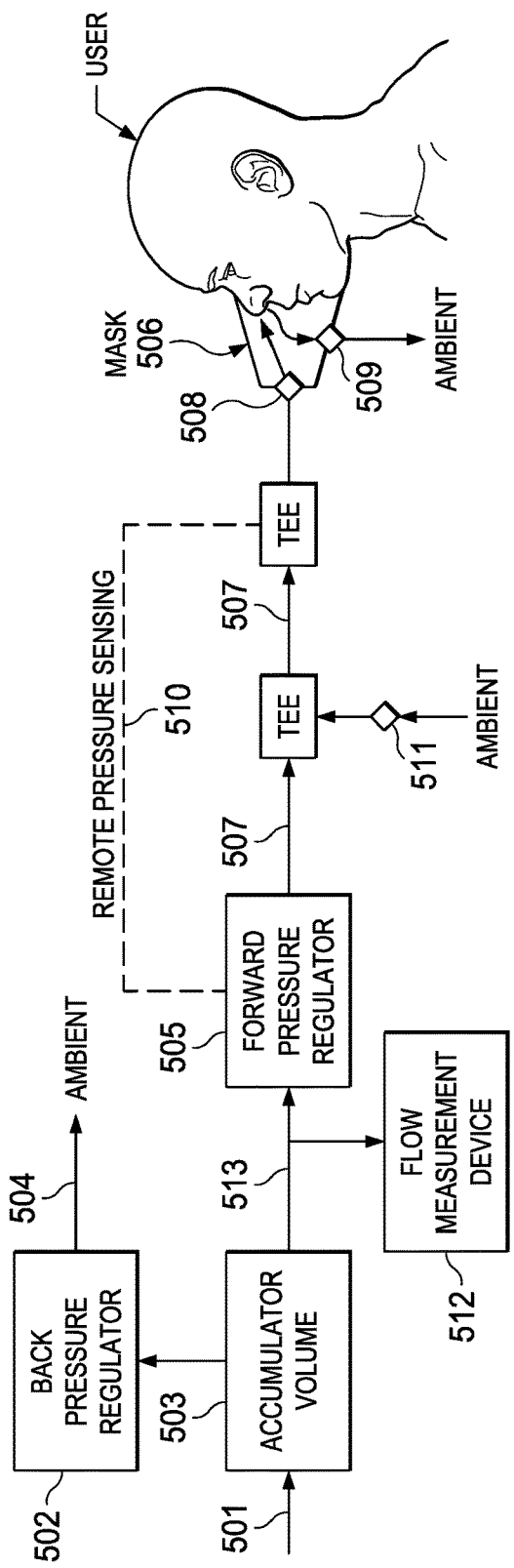

FIG. 21A shows a block diagram of pressure-on-demand operation with a generic oxygen separation flowchart 300. Again, atmospheric air 302 enters an air inlet pump 304, which air flow contact inlet air flow meter 306. The air that flows past the inlet air flow meter 306 then contact an oxygen separator 308 (which can be any oxygen separation technology such as EOS, a PSA membrane, or the like). The output from the oxygen separator 308 enters, e.g., a pressurized accumulator 310 (or can be directly fed to the next step), which is connected via a valve to a mask flow meter 312 and a mask 314, or can be fully or partially bypassed into a bypass 316. As with the system shown in FIG. 20A or 20B, mask flow meter 312 is connected to and provides data to the system inlet flow rate control 318 (which controls the pump set-point) and which modifies the output of air inlet pump 304. Second, a user-defined target altitude set point 320 (an altitude setting) is provided to the oxygen removal control 322, which in conjunction with information about the amount of air flow at air flow meter 306, controls the amount of current that reaches the electrochemical stack 308, which then controls the amount of oxygen in the atmospheric air that is pulled from the atmospheric air at the electrochemical stack 308. The system inlet flow rate control 318 also received input from the measured system pressure 324, which is measuring the amount of pressure in the pressurized accumulator. This embodiment can also include a valve that provides atmospheric air 302 to an optional blend air pump 326 that provides air into the pressurized accumulator 310, under the control of oxygen removal control 322. In FIG. 22B, a forward pressure regulator 325, is configured to respond to pressure differentials in the conduit connecting the accumulator 310 and the mask.

Figure 21B:
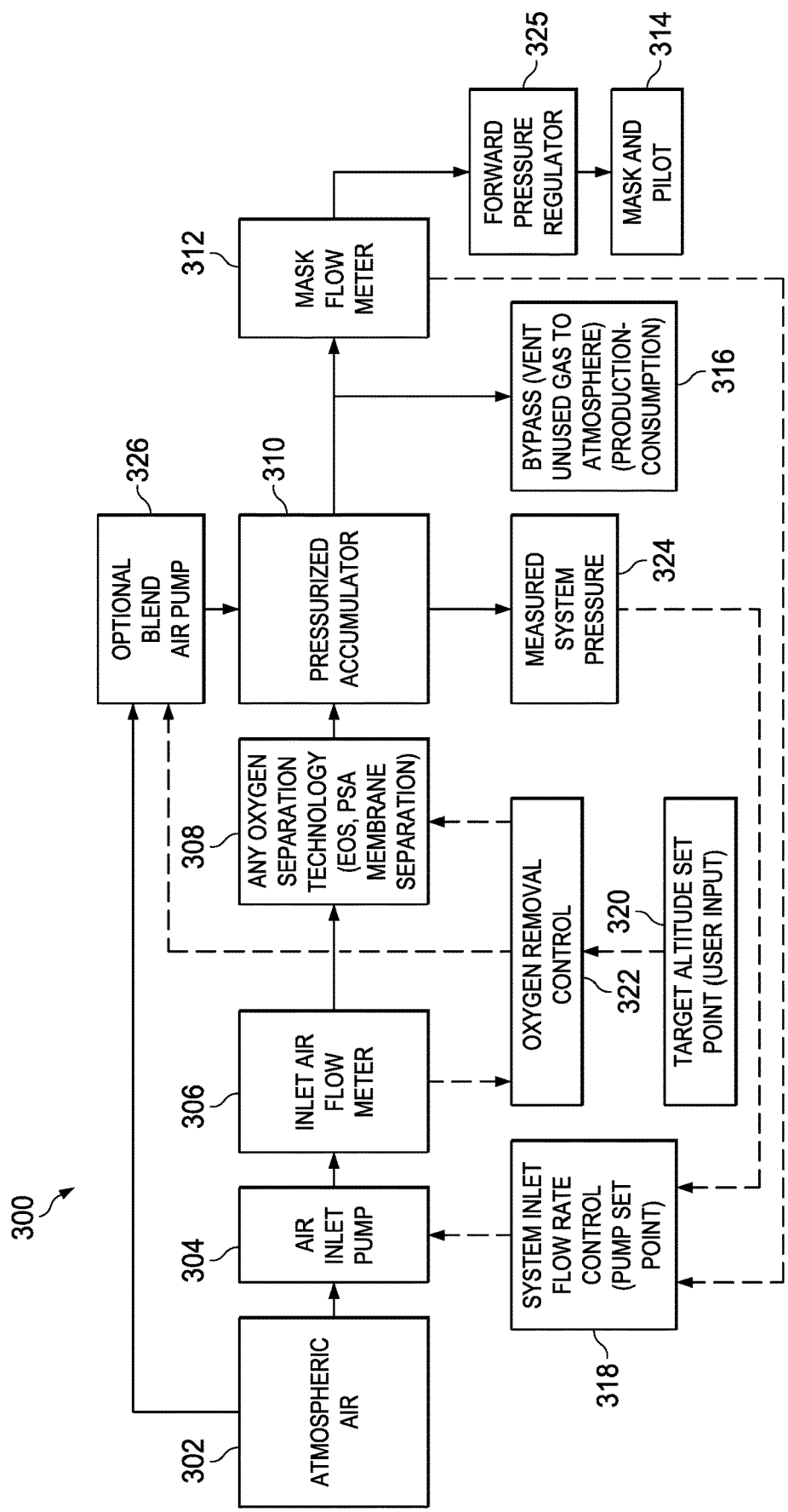

In FIGS. 21A and 21B, air pump 304 can be PDP-101 and/or PDP-102. Inlet air flow meter 306 is equivalent in function and placement to FM-101 and/or FM-103. Pressurized accumulator 310 flow meter 312 is equivalent ACUM-101. Flow meter 312 is equivalent to FM-102. Bypass 316 is equivalent to BPR-101. Electrochemical stack 308 is equivalent to EOS-101 and EOS-102. System pressure 324 is equivalent to PT-101 and/or PT-103 or equivalent pressure transducers located between the EOS system and the accumulator ACUM-101. Forward pressure regulator 325 is equivalent to FPR-101.

Pressure on-demand. FIGS. 22A and 22B show the components of a hypoxia training system 500 that accomplished delivery oxygen depleted gas to a person, providing a pressure on demand capability. Oxygen depleted air enters the system 501. An electrochemical oxygen pump may be used as the source of oxygen depleted air. In one non-limiting alternative, a pressure swing absorption device may be used as a source of oxygen depleted air. In another alternatively, a membrane separation gas processing device may be used. Alternatively, oxygen depleted air may be sourced from compressed gas cylinders, that includes a mechanism for mixing and dilution, typically an oxygen supply or ambient air can be diluted with nitrogen. For example, U.S. Pat. No. 6,871,645, relevant portions incorporated herein by reference, teaches a method of producing nitrogen/oxygen mixtures suitable for use with the current invention.

Each of the above-mentioned methods of preparing oxygen-depleted gas can be used in conjunction with the present invention. Additionally, the above methods can produce gas mixtures that simulate the oxygen concentration of air at various altitudes, such as below:

| Height | Oxygen content (%) |
|---|---|
| Sea level | 21.00% |
| 5000 ft | 17.28% |
| 10,000 ft | 14.08% |
| 15,000 ft | 11.38% |
| 20,000 ft | 9.09% |
| 25,000 ft | 7.11% |
| 30,000 ft | 5.43% |
| 34,000 ft | 4.38% |

In FIG. 22A, the hypoxia training system 500 begins with the concentration of oxygen in the gas 501 entering the system, which is adjustable to simulate an altitude between sea level and 35,000 ft following the table above. Moreover, the oxygen content of the gas entering 501 can be adjusted up or down in "real time" to simulate changes in atmospheric oxygen content experienced when transitioning to a higher altitude or transitioning to a lower altitude. Although other pressures may be used, a suitable gas pressure for oxygen depleted gas entering at 501 is 30 psi. A gas pressure range for use with the present invention is from about 10-40 psi. Gas 501 is directed into an accumulator/gas container 503. The system pressure is maintained at the appropriate upper level by a back-pressure regulator (BPR) 502 in fluid communication with an gas accumulator/container 503. Once the desired pressure is reached, the BPR 502 has the capacity to vent excess gas to the ambient surrounding atmosphere 504 external to the accumulator 503. The BPR 502 setting determines the upper limit of the system pressure.

The accumulator 503 with an exact volume is used to store the gas at a pre-determined pressure. The accumulator 503 can be constructed from a number of polymer(s), e.g., polypropylene, metals, ceramics, composites, fiberglass, plastics, etc. Materials for construction of the accumulator 503 can include other polymers, composites or metals such as stainless steel or aluminum.

The larger the internal gas volume of the accumulator 503 the smaller the pressure fluctuation. In one non-limiting example, the size the volume of accumulator 503 and associated system conduits are sized to maintain the gas pressure in the accumulator 503, to minimize the flow requirement for oxygen depleted gas 501 flow entering the system at accumulator 503, but also provide the needed gas flow to the mask 506 according to a breathing pattern of the person or user wearing the mask 506. Maintaining a flow according to the breathing pattern is achieved in conjunction with operation of a forward pressure regulator 505. The forward pressure regulator 505 is operated by an appropriately adjusted PID controller.

The internal gas volume of the accumulator 503 is determined based on the allowable fluctuation of system pressure, a pressure drop through balance of components, and the inlet pressure required by the forward pressure regulator 505.

A forward pressure regulator 505 is required to control delivery of the oxygen depleted gas to the mask 506. The mask 506 used can be the kind typically used in aviation by aircraft pilots and crew. Typically the mask 506 will be a "demand type" also known as a "pressure demand mask". The preferred mask 506 is full face (covers nose and mouth). The mask 506 is typically of plastic, rubber and/or silicone. The mask 506 incorporates a face seal. Typical masks 506 are available commercially from, e.g., GENTEX®, however, other equivalent mask types are available from other manufacturers.

Gas is delivered to the mask 506 through a hose conduit 507. A forward pressure regulator 505 always tries to maintain downstream pressure in conduit 507 at a set point or set points by regulating and making adjusting to allow more or less flow in response to the breathing inhalation/exhalation patterns of the person using the mask 506. The gas pressure in the conduit 507 between the forward pressure regulator 505 and the mask 506 is usually only slightly above (or below) the pressure of the surrounding atmosphere outside the mask 506. The mask 506 also prevents the delivered gas from leaking to the ambient environment by sealing against the users face.

The hypoxia training system in FIG. 22B may be used in conjunction with a flow meter or flow measuring device 512, which is mounted in the conduit 513 between accumulator 503 and FPR 505. The training system may also employ an oxygen sensor mounted in the conduit between accumulator 503 and FPR 505.

The system prevents delivering more flow to the mask 506 via conduit 507 than actually necessary according to—and coordinated with—the inhale and exhale actions of the user at the mask 506. The present invention prevents pressure in the accumulator 503 from dropping below the predetermined threshold during operation of the mask 506 by the user, especially during rapid breathing/high breath flow.

The mask 506 uses a unidirectional valve 508 at the inlet of the mask 506 to prevent exhaled air from going back through the inlet tube to conduit 507. The unidirectional valve 508 is sometimes called the inlet valve or demand valve. The unidirectional valve 508 is generally built into the mask 506 (i.e., is built in to the mask). A pressure-on-demand mask can also has a pressure-biased unidirectional exhale valve 509. This unidirectional exhale valve 509 allows the user to exhale to the environment external to the mask 506 at a pressure only slightly higher than the inlet pressure. The unidirectional exhale valve 509 can also be built into the mask. The unidirectional valves 508, 509 may have an altitude compensation feature, whereby their action is mechanically or electronically coupled to compensate for changing altitudes during flight (e.g., changes ambient atmospheric pressure).

In the Hypoxia Training System, the forward regulator valve 505 is preferably an electronic forward pressure regulator (eFPR) type. For example, the forward regulator valve 505 may be an Alicat Electronic Forward Pressure Regulator. Alternatively, the forward regulator valve 505 may be a mechanical type regulator such as a CRU-103. The forward pressure regulator 505 is used in conjunction with a pressure sensing port 510.

The eFPR pressure sensing port 510 measures the pressure in the mask conduit 507; this is particularly important if a long conduit 507 is used to deliver the product gas due to a pressure drop through along the length of the conduit 507. The sensing port 510 may be made from a plastic tube (internal diameter 3-5 millimeters). The sensing port 510 is connected to hose 507 by a T-junction 512.

The position of the T-junction 511 is important and is, preferably, placed as close to unidirectional valve 508 as possible. Preferably, the distance between the T-junction 511 and the unidirectional valve 508 at the inlet of the mask 506 is 0.1-0.5 inch. Alternatively, the distance can be 0.5-6.0 inches. The pressure sensing port 510 connects to the forward pressure regulator 505. This sensing arrangement provides rapid, continuous and accurate readings of the pressure near or at the inlet valve.

Figure 23:
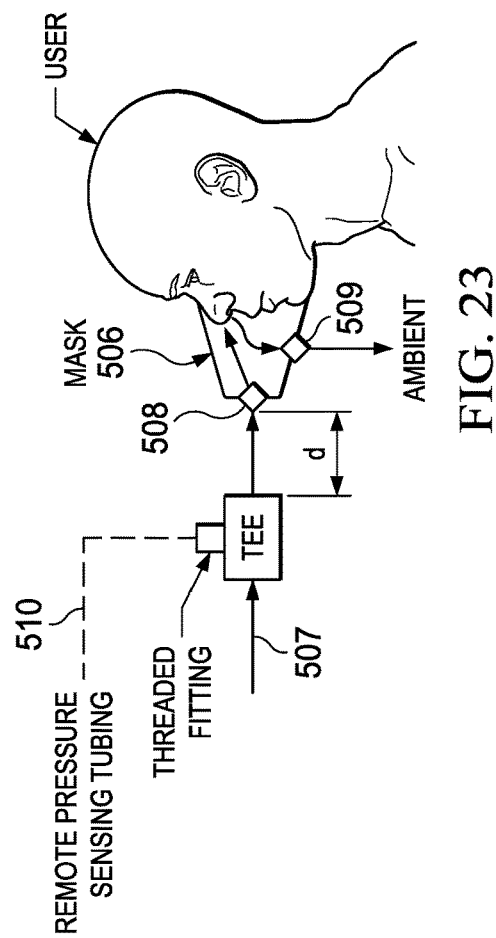
FIG. 23 shows an arrangement of the pressure sensing port.

FIG. 23 shows the arrangement of the pressure sensing port. The feedback from the pressure sensing port 510 allows the forward regulator valve 505 (e.g., an eFPR 505) to open or close to adjust the pressure by increasing or decreasing the flow to the mask 506 based on the pressure at the mask 506 (vs. the pressure at the FPR output which could be considerably higher).

Specifically the eFPR 505, in conjunction with the sensing port, senses an increase in pressure in the conduit 507 when the unidirectional valve 508 at the inlet of the mask 506 closes, during exhalation by the person wearing the mask 506. When this pressure increase is sensed, the eFPR 505 closes to maintain the gas pressure in the accumulator 503 and associated conduits 507. Note that when the accumulator 503 is at its set point upper pressure and the eFPR 505 is closed, oxygen depleted gas 502 entering accumulator 503 can vent through back pressure regulator 502 to the ambient 504. The eFPR 505 in conjunction with the pressure sensing port 510 also detects when a pressure decrease in conduit 507 occurs, that is, when the unidirectional valve 508 at the inlet of the mask 506 opens during inhalation by the person wearing the mask 506. The eFPR is activated to open, to allow reduced oxygen air to exit the accumulator via the hose 507 and enter the mask 506. Thus, the on-demand feature allows gas to leave the accumulator 503 only when it is needed by and according to the users breathing pattern. This has the advantage of allowing pressure in the accumulator 503 and associated conduits 506 to be maintained without depletion over time. The forward regulator valve 505 is useful in another sense. If it were not in a position between the accumulator 503 and the mask 506, the pressure in the accumulator 503 and associated conduits 507 may be at a level where unidirectional valve 508 at the inlet of the mask 506 could open for extended periods. The wearer of the mask 506 would experience excess gas entering the mask 506, could suffer discomfort, and experience difficulty breathing.

Conduit 507 incorporates a unidirectional check valve 511. If the user of the mask 506 breathes at an average flow rate that is much higher than what the system is designed for, the system can depressurize to below a desirable limit. This lower limit is decided based on any minimum pressure limits posed by downstream balance-of-plant components such as the forward pressure regulator 505. In the event the system depressurizes and shuts down, the user may not receive gas sufficient to breathe adequately. In order to prevent breathing discomfort or shortage, the check valve 511 will open. The check valve 511 is in fluid communication with the ambient atmosphere. The check valve 511 is designed to open when the gas pressure in conduit 507 reaches a low value versus the atmospheric gas pressure external to conduit 507. When check valve 511 opens, ambient air from the external atmosphere will be immediately enter conduit 507 and be available to support breathing by the user of the mask 506.

Example 7

Table 3 depicts key parameters of a hypoxia training device to be used in conjunction with a depleted oxygen source and a pressure on demand pilot's mask.

TABLE 3

Hypoxia trainer: accumulator size as a function of average breath rate, breaths per minute and system pressure fluctuation at a constant inlet flow rate.

| Average Breathing Flowrate (SLPM) | Peak Flow Rate (SLPM) | Breaths per Minute | Upper Limit of System Pressure (psig) | Lower Limit of System Pressure (psig) | Accumulator Volume (L) |
|---|---|---|---|---|---|
| 6.7+ | 21 | 11.2 | 14.7 | 10 | Not needed* |
| 16.4 | 51 | 14.6 | 14.7 | 10 | 0.5 |
| 25 | 78 | 18.5 | 14.7 | 10 | 1.75 |
| 30 | 94 | 19.1 | 14.7 | 10 | 2.5 |
| 35 | 110 | 21.4 | 14.7 | 10 | 2.75 |

+Hypoxia familiarization training by the reduced oxygen breathing method

The Table gives average breathing flow rates, as determined from multiple human studies. The highest ventilation rates observed in human tests is approximately 30±6 LPM. The Hypoxia Training System in Example 7 was sized for this to be the maximum consumption rate (time averaged). Specifically the inlet flow rate of 37.5 SLPM of oxygen depleted gas was used, allowing a margin. The Hypoxia Training Device in this example also accommodates a peak flow rate, calculated based on a sinusoidal breathing waveform (with clipped exhalation) that is a function of tidal volume and breaths per minute; the higher the average breathing flow rate, the higher the peak flow. These values are also from previous human studies. The peak flow rates given in the Table represent the required peak gas flow between the eFPR and the mask via the hose via 507. The Table also shows the number of breaths per minute the device would accommodate.

An electrochemical (EOS) described earlier can provide oxygen depleted air at the desired volume of 37.5 SLPM. Alternatively, a pressure swing absorption device may be used as a source of oxygen depleted air and sized to meet the 37.5 SLPM flow rate. Alternatively, oxygen depleted air may be sourced from one or more compressed gas cylinders, where there is a mechanism for dilution, of oxygen or air with an inert gas such as nitrogen. A compressed gas cylinder source can be sized sufficient to produce 37.5 SLPM of oxygen depleted gas. In this example, the oxygen concentration of oxygen in the gas entering the system at 501 can be adjusted to simulate the concentration of oxygen at altitudes between sea level and 35,000 ft. Moreover, the oxygen content can be adjusted up or down in "real time" to simulate changes in atmospheric oxygen content experienced when ascending and descending.

In this example, oxygen depleted air is added to the accumulator. The gas is supplied under pressure from a pump mechanism connection to inlet 501. The backpressure regulator is set at 14.7 psig, which sets the upper limit of the system pressure. The forward pressure regulator requires a minimum of 10 psig of inlet pressure to allow maximum flow through the regulators. This determines the low limit system pressure. The forward pressure regulator has been selected to allow a peak flow rate of 100 (SLPM) between the accumulator and mask at pressures of 10 psig or greater. An Alicat Electronic Forward Pressure Regulator is used.

Example 7 gives consideration to accumulator gas volume requirement, which is important. In the Table, accumulator size has been assessed according to parameters of average breathing flow rate and breaths per minute of the person using the mask. The assessment shows that the volume requirement of the accumulator needs to be scaled to match the highest values of flow rate and breaths per minute. The assessment indicates an accumulator gas volume of 2.75 L is needed. If a smaller accumulator is used, e.g., 1.75 L, and if the user has an average breathing flow rate of greater than 25 SLPM (as is often the case), the average pressure of in the accumulator and associated conduits could not be maintained close to an average and there would be a fluctuation in pressure wide excursions in pressure. Because of the fluctuations, the pressure for periods of time, will drop to low enough levels that delivery of oxygen depleted gas to the mask would cease to occur. In other words, the pressure would periodically reach the lower limit system pressure of 10 psig. At this point the eFPR would be unable to accommodate the required peak gas flow of 110 SLPM to the mask. The mask's user would experience discomfort when attempting to inhale, due to insufficient volume of gas flowing to the mask. To summarize, Example 1 of a Hypoxia Training System uses approximately 2.75 L (3.0 L with margin) of accumulated volume to store oxygen depleted air at 14.7 psig since this allows the system to undergo a pressure fluctuation of only 4.7 psi with an inlet flow rate of approximately 37.5 SLPM.

Example 8

Table 4 depicts key parameters of an hypoxia training device to be used in conjunction with a source of oxygen depleted air and a pressure-on-demand pilot's mask. Table 4 gives average breathing flow rates, as determined from multiple human studies as in Table 3. In this example, the Hypoxia Training System is scaled for the maximum consumption rate (time averaged) by the person wearing the mask, allowing for maximum breathing flow rates, which again is 37.5 SLPM of oxygen depleted gas, allowing a margin. In this example, the training system also accommodates a peak flow rate, calculated based on a sinusoidal breathing waveform (with clipped exhalation) that is a function of tidal volume and breaths per minute; the higher the average breathing flow rate, the higher the peak flow. The values given are from previous human studies. The peak flow rates given in the Table represent the required peak gas flow between the eFPR 505 and the mask 506 via the conduit 507. The Table also shows the number of breaths per minute the device would have to accommodate.

TABLE 4

Hypoxia trainer: accumulator size as a function of average breath rate, breaths per minute and system pressure fluctuation at a constant inlet flow rate.

| Average Breathing Flowrate (SLPM) | Peak Flow Rate (SLPM) | Breaths per Minute | Upper Limit of System Pressure (psig) | Lower Limit of System Pressure (psig) | Accumulator Volume (L) |
|---|---|---|---|---|---|
| 6.7 | 21 | 11.2 | 11.7 | 10 | Not needed* |
| 16.4 | 51 | 14.6 | 11.7 | 10 | 1.5 |
| 25 | 78 | 18.5 | 11.7 | 10 | 4.5 |
| 30 | 94 | 19.1 | 11.7 | 10 | 6.5 |
| 35 | 110 | 21.4 | 11.7 | 10 | 7 |

A electrochemical (EOS) described hereinabove can provide oxygen depleted air at the desired volume of 37.5 SLPM. Alternatively, a pressure swing absorption device may be used as a source of oxygen depleted air and sized to meet the 37.5 SLPM flow rate. Alternatively, oxygen depleted air may be sourced from one or more compressed gas cylinders, where there is a mechanism for dilution, of oxygen or air with an inert gas such as nitrogen. A compressed gas cylinder source can be sized sufficient to produce 37.5 SLPM of oxygen-depleted gas. In this example, the oxygen concentration of oxygen in the gas 501 entering the system at can be adjusted to simulate the concentration of oxygen at altitudes between sea level and 35,000 ft. Moreover, the oxygen content can be adjusted up or down in "real time" to simulate changes in atmospheric oxygen content experienced when ascending and descending. Oxygen depleted air is added to the accumulator 503, supplied under pressure from a pump mechanism in fluid connection with the inlet of accumulator 503 to deliver gas 501.

The backpressure regulator 502 is set at 11.7 psig, which sets the upper limit of the system pressure. The forward pressure regulator 505 requires a minimum of 10 psig of inlet pressure to allow maximum flow through the regulators. This determines the low limit system pressure. The forward pressure regulator 505 is generally selected to allow a peak flow rate of 100 (SLPM) between the accumulator 503 and mask 506 at pressures of 10 psig or greater. An Alicat Electronic Forward Pressure Regulator may be used.

Example 8 gives consideration to accumulator gas volume requirement. In the Table, accumulator size has been assessed according to parameters of average breathing flow rate and breaths per minute of the person using the mask. The volume requirement of the accumulator needs to be scaled to match the highest values of flow rate and breaths per minute. This example uses an accumulator gas volume of 7.0 L.

Note that, when the breathing consumption is very small (6.7 SLPM), there is no need for an accumulator since the inlet flow rate is large enough (37.5 SLPM) to provide the peak flow consumed and maintain constant system pressure. This pattern of breathing is not representative however of a person's respiratory physiology. An accumulator is required for higher average breathing flow rates. Accumulator size is a consideration. As the user consumes the gas within the system, the pressure will fluctuate and experience wide excursions in pressure. Because of the fluctuations, the pressure, for periods of time, will drop to low enough levels that delivery of oxygen depleted gas to the mask would cease to occur. In other words, the pressure would periodically reach the lower limit system pressure of 10 psig. At this point the eFPR would be unable to accommodate the required peak gas flow of 110 SLPM to the mask. The person wearing the mask would experience difficulty and discomfort when attempting to inhale, due to insufficient volume of gas flowing to the mask. The average system pressure drop over time, for a given flow rate, is also a function of accumulator volume; a small accumulated volume in the system will cause the pressure to drop rapidly whereas an infinitely large accumulated volume will be able to maintain system pressure. An accumulator of 7 L allows the system to operate at the highest breath flow rates while maintaining system pressure within a desired range.

To summarize, Example 8 of a Hypoxia Training System uses approximately 7.0 L of accumulator volume to store oxygen depleted air at 11.7 psig since this allows the system to undergo a pressure fluctuation of only 4.7 psi with an inlet flow rate of approximately 37.5 SLPM. The data in the table in Table 4 (below) differs from Table 3 (below) that system pressure is lower, therefore pumping equipment for delivering oxygen depleted gas to the accumulator can be scaled back, reducing pump size and or power requirements. This comes at the expense of needing a larger space envelope in the training system to accommodate a larger accumulator.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Rainford D J, Gradwell D P, eds. Ernsting's aviation medicine, 4th ed. New York: Oxford University Press; 2006.
D. S. Files, James T. Webb, and A. A. Pilmanis, Depressurization in Military Aircrafts: Rates, Rapidity, and Health Effects for 1055 incidents, Aviation, Space, and Environmetal Medicine, 76(6), 2005, 523-529.
Sausen K P, Bower E A, Stiney M E, et al. A closed-loop reduced oxygen breathing device for inducing hypoxia in humans. Aviation Space and Environmental Medicine 2003; 74:1190-7.
Artino A R, Folga R V, Swan B D. Mask-on hypoxia training for tactical jet aviators: evaluation of an alternate instructional paradigm. Aviation Space and Environmental Medicine 2006; 77: 857-63.
Artino A R, Folga R V. Normobaric Hypoxia Training: The Effects of Breathing-Gas Flow Rate on Symptoms. Aviation Space and Environmental Medicine 2009; 80: 547-552.
Westerman, Roderick A. Hypoxia familiarisation training by the reduced oxygen breathing method. ADF Health April 2004; 5:11-15.
Voorhees, V.; Adams, R., The use of the oxides of platinum for the catalytic reduction of organic compounds I. Journal of the American Chemical Society 1922, 44, 1397-1405.
Adams, R.; Shriner, R. L., Platinum oxide as a catalyst in the reduction of organic compounds III Preparation and properties of the oxide of platinum obtained by the fusion of ceiloroplatinic acid with sodium nitrate. Journal of the American Chemical Society 1923, 45, 2171-2179.
Carothers, W. H.; Adams, R., Platinum oxide as a catalyst in the reduction of organic compounds II Reduction of aldehydes activation of the catalyst by the salts of certain metals. Journal of the American Chemical Society 1923, 45, 1071-1086.

What is claimed is:

1. A device for controlling oxygen to a mask comprising:
an air inlet pump in fluid communication with atmospheric air;
an inlet air flow meter connected to the air inlet pump, wherein the inlet air flow meter measures an air flow from the air inlet pump;
one or more oxygen separators comprising
an input connected to the inlet air flow meter;
an output;
one or more electrochemical cells each comprising a cathode and an anode separated by a proton exchange membrane, each of the anode and cathode in communication with an input and an output, wherein the input of the cathode is in fluid communication with the atmospheric air, and wherein the input of the anode is in fluid communication with a source of liquid water; and
a power supply connected to the one or more electrochemical cells, wherein the mask is in fluid communication with the output from the cathode of the one or more electrochemical cells, wherein oxygen is removed from the atmospheric air during contact with the cathode when hydrogen ions separated from liquid water by a catalyst on the anode convert oxygen in the atmospheric air into water;
a pressurized accumulator connected to the output from the one or more oxygen separators and having a pressure sensor, wherein the pressure sensor measures a pressure of a fluid within the pressurized accumulator while the mask is being used;
an outlet flow meter connected to the pressurized accumulator, wherein the outlet flow meter measures an oxygen flow rate to the mask while the mask is being used;
a system inlet flow rate control connected to the pressure sensor of the pressurized accumulator, to the outlet flow meter, and to the air inlet pump,
wherein the system inlet flow rate control automatically controls a flow rate of the air inlet pump, and
wherein the system inlet flow rate control comprises an inlet flow rate control processor comprising programmed instructions to calculate a user air consumption from input from the pressure sensor of the pressurized accumulator and input from the outlet flow meter, to calculate a pump set point from the calculated user air consumption, and to automatically control the flow rate of the air inlet pump using the calculated pump set point; and
an oxygen removal control connected to the inlet flow meter and directly connected to the one or more oxygen separators,
wherein the oxygen removal control controls the amount of oxygen that is removed from the atmospheric air at the one or more electrochemical cells, and
wherein the oxygen removal control comprises an oxygen removal control processor comprising programmed instructions to accept input for a target altitude set point, to calculate an electrical current to the one or more oxygen separators required to remove an amount of oxygen from the atmospheric air to simulate a target altitude from at least the target altitude set point and input from the inlet flow meter, and to automatically control the amount of oxygen removed from the atmospheric air at the one or more electrochemical cells using the calculated electrical current.

2. The device of claim 1, wherein the anode catalyst is an electrocatalyst and wherein water molecules that contact the electrocatalyst are dissociated into hydrogen protons and oxygen by electrolysis, wherein the protons traverse the proton exchange membrane to the cathode, and oxygen in the atmospheric air is reacted with protons at the cathode into water.

3. The device of claim 1, further comprising an oxygen sensor in fluid communication with the output from each cathode and connected to a processor that determines the amount of oxygen in the outputs of the cathodes, wherein the processor controls the power to the electrochemical cell based on the amount of oxygen detected and one or more settings for hypoxia training.

4. The device of claim 1, further comprising one or more pumps and valves in fluid communication with each anode and each cathode, wherein the one or more pumps and valves control air flow to and from each cathode, and water flow into each anode, wherein the one or more pumps and valves regulate the reduction in oxygen from the atmospheric air and the air flow to the mask and the conversion of water into oxygen.

5. The device of claim 1, further comprising a forward pressure regulator before the mask.

6. The device of claim 1, further comprising a temperature regulator for the one or more electrochemical cells, wherein the temperature is reduced by contacting the electrochemical cell with a coolant.

7. The device of claim 1, wherein the device is defined further as a pressure-on-demand device, wherein a reduction in the amount of oxygen removed from the atmospheric air by the one or more electrochemical cells is controlled based on air intake at the mask, wherein air intake is determined by one or more sensors that monitor breath rate, wherein the one or more sensors are connected to a control logic that adjusts a current to the one or more electrochemical cells in real time.

8. The device of claim 7, wherein the logic determines an average air flow rate at the mask and adjusts a flow rate of the air inlet pump.

9. The device of claim 1, wherein the one or more electrochemical cells comprise a stack of the anodes and the cathodes.

10. The device of claim 1, wherein the power supply is defined further as a hybrid power distribution system that limits current draw from an external power source.

11. The device of claim 1, further comprising a water recovery system in fluid communication with each cathode, wherein the water in the water recovery system can be at least one of: delivered to each anode, stored, or disposed.

12. The device of claim 1, wherein the anode catalyst is an Ir—Ru-Ox catalyst with at least one of Au or Pt nanoparticles.

13. The device of claim 1, wherein the anode catalyst is an Ir—Ru-Ox catalyst with a 5 to 95 mol % Ir to Ru ratio.

14. The device of claim 1, wherein the anode catalyst is an Ir—Ru-Ox catalyst that further comprises at least one of an Au loading range of 0, 1, 5, 10, 15, 20, 25, 30, 35, or 40 wt %, or a Pt loading range of 0, 5, 10, 15, or 20 wt %.

15. The device of claim 1, wherein each cathode further comprises a cathode electrochemical catalyst that reduces oxygen in the atmospheric air.

16. The device of claim 1, wherein in each electrochemical cell, the cathode has a first and a second side, and the first side is in contact with the proton exchange membrane and the second side is in contact with an air diffusion layer, wherein the air diffusion layer is in contact with the cathode input and output.

17. The device of claim 1, wherein in each electrochemical cell, the anode has a first and a second side, and the first side is in contact with the proton exchange membrane and the second side is in contact with a water flow layer, wherein the water flow layer is in contact with the anode input and output.

18. The device of claim 1, wherein the anode catalyst is an electrocatalyst and the electrocatalyst demonstrates a greater than 65%, 70%, 75%, 80%, or 85% water electrolysis efficiency.

19. The device of claim 1, wherein an ion exchange resin is positioned at least one of between the source of water and the anode and/or after the anode.

20. A device for hypoxia training comprising:
an accumulator in fluid communication with a gas inlet and a back pressure regulator at a first output and a forward pressure regulator at a second output, wherein the accumulator receives hypoxic air from the one or more oxygen separators, wherein the one or more oxygen separators are defined further as comprising one or more electrochemical cells each comprising: a cathode and an anode separated by a proton exchange membrane, each anode and cathode in communication with an input and an output, wherein the input of each cathode is in fluid communication with atmospheric air, and wherein the input of each anode is in fluid communication with a source of liquid water; wherein a power supply is connected to the one or more electrochemical cells, wherein a mask is in fluid communication with the output from each cathode of the one or more electrochemical cells, wherein oxygen is removed from the atmospheric air during contact with each cathode when hydrogen ions separated from liquid water by a catalyst on each anode converts oxygen in the atmospheric air into water;
a conduit connected to an output of the forward pressure regulator that connects to an inlet of a unidirectional valve at the mask, the mask being further connected to a unidirectional output valve;
a conduit pressure sensor in communication with an interior of the conduit, wherein the conduit pressure sensor is connected to and controls the forward pressure regulator to control the flow of a gas from the accumulator to the mask; and
an air inlet pump in fluid communication with atmospheric air;
an inlet air flow meter connected to the air inlet pump wherein the inlet air flow meter measures an air flow from the air inlet pump;
an outlet flow meter connected to the accumulator, wherein the outlet flow meter measures an oxygen flow rate to the mask while the mask is being used;
a system inlet flow rate control connected to a pressure sensor of the accumulator, to the outlet flow meter, and to the air inlet pump,
wherein the system inlet flow rate control automatically controls a flow rate of the air inlet pump, and
wherein the system inlet flow rate control comprises an inlet flow rate control processor comprising programmed instructions to calculate a user air consumption from input from the pressure sensor of the pressurized accumulator and input from the outlet flow meter, to calculate a pump set point from the calculated user air consumption, and to automatically control the flow rate of the air inlet pump using the calculated pump set point; and an oxygen removal control connected to the inlet flow meter and directly connected to the one or more oxygen separators, wherein the oxygen removal control controls the amount of oxygen that is removed from the atmospheric air at the one or more electrochemical cells, and wherein the oxygen removal control comprises an oxygen removal control processor comprising programmed instructions to accept input for a target altitude set point, to calculate an electrical current to the one or more oxygen separators required to remove an amount of oxygen from the atmospheric air to simulate a target altitude from at least the target altitude set point and input from the inlet flow meter, and to automatically control the amount of oxygen removed from the atmospheric air at the one or more electrochemical cells using the calculated electrical current.

21. The device of claim 20, wherein in each electrochemical cell, the anode catalyst is an electrocatalyst and wherein water molecules that contact the electrocatalyst are dissociated into hydrogen protons and oxygen by electrolysis, wherein the protons traverse the proton exchange membrane to the cathode, and oxygen in the atmospheric air is reacted with protons at the cathode into water.

22. The device of claim 20, further comprising an oxygen sensor in fluid communication with the output from each cathode and connected to a processor that determines the amount of oxygen in the outputs, wherein the processor controls the power to the one or more electrochemical cells based on the amount of oxygen detected and one or more settings for hypoxia training.

23. The device of claim 20, further comprising one or more pumps and valves in fluid communication with each anode and each cathode, wherein the one or more pumps and valves control air flow to and from each cathode, and water flow into each anode, wherein the one or more pumps and valves regulate the reduction in oxygen from the atmospheric air and the air flow to the mask and the conversion of water into oxygen.

24. The device of claim 20, further comprising a forward pressure regulator before the mask.

25. The device of claim 20, further comprising a temperature regulator for the one or more electrochemical cells, wherein the temperature is reduced by contacting the one or more electrochemical cells with a coolant.

26. The device of claim 20, wherein the device is defined further as a pressure-on-demand device, wherein a reduction in the amount of oxygen removed from the atmospheric air by the one or more electrochemical cells is controlled based on air intake at the mask, wherein air intake is determined by one or more sensors that monitor breath rate, wherein the one or more sensors are connected to a control logic that adjusts the current to the one or more electrochemical cells in real time.

27. The device of claim 26, wherein the logic determines an average air flow rate at the mask and adjusts a flow rate of the pump.

28. The device of claim 20, wherein the one or more electrochemical cells comprise a stack of the anodes and the cathodes.

29. The device of claim 20, wherein the power supply is defined further as a hybrid power distribution system that limits current draw from an external power source.

30. The device of claim 20, further comprising a water recovery system in fluid communication with each cathode, wherein the water in the water recovery system can be at least one of: delivered to each anode, stored, or disposed.

31. The device of claim 20, wherein the anode catalyst is an Ir—Ru-Ox catalyst with at least one of Au or Pt nanoparticles.

32. The device of claim 20, wherein the anode catalyst is an Ir—Ru-Ox catalyst with a 5 to 95 mol % Ir to Ru ratio.

33. The device of claim 20, wherein the anode catalyst is an Ir—Ru-Ox catalyst that further comprises at least one of an Au loading range of 0, 1, 5, 10, 15, 20, 25, 30, 35, or 40 wt %, or a Pt loading range of 0, 5, 10, 15, or 20 wt %.

34. The device of claim 20, wherein each cathode further comprises a cathode electrochemical catalyst that reduces oxygen in the atmospheric air.

35. The device of claim 20, wherein in each electrochemical cell, the cathode has a first and a second side, and the first side is in contact with the proton exchange membrane and the second side is in contact with an air diffusion layer, wherein the air diffusion layer is in contact with the cathode input and output.

36. The device of claim 20, wherein the anode has a first and a second side, and the first side is in contact with the proton exchange membrane and the second side is in contact with a water flow layer, wherein the water flow layer is in contact with the anode input and output.

37. The device of claim 20, wherein the anode catalyst is an electrocatalyst and the electrocatalyst demonstrates a greater than 65%, 70%, 75%, 80%, or 85% water electrolysis efficiency.

38. The device of claim 20, wherein an ion exchange resin is positioned at least one of between the source of water and the anode and/or after the anode.

* * * * *